(12) United States Patent
Eddaoudi et al.

(10) Patent No.: US 8,034,952 B2
(45) Date of Patent: Oct. 11, 2011

(54) SUPRAMOLECULAR ASSEMBLIES AND BUILDING BLOCKS

(75) Inventors: Mohamed Eddaoudi, Tampa, FL (US); Farid Nouar, Tampa, FL (US); Jarrod F. Eubank, Tampa, FL (US); Lukasz Wojtas, Tampa, FL (US); Till Bousquet, Tampa, FL (US); Michael Zaworotko, Tampa, FL (US)

(73) Assignee: University of South Florida, Tampa, FL (US)

(*) Notice: Subject to any disclaimer, the term of this patent is extended or adjusted under 35 U.S.C. 154(b) by 227 days.

(21) Appl. No.: 12/272,764

(22) Filed: Nov. 17, 2008

(65) Prior Publication Data
US 2009/0143596 A1    Jun. 4, 2009

Related U.S. Application Data

(60) Provisional application No. 60/988,195, filed on Nov. 15, 2007.

(51) Int. Cl.
*C07F 15/00* (2006.01)
*C07F 1/00* (2006.01)
(52) U.S. Cl. ......................... 548/103; 556/110
(58) Field of Classification Search ............. 548/103; 556/110
See application file for complete search history.

(56) References Cited

U.S. PATENT DOCUMENTS

| | | | |
|---|---|---|---|
| 5,648,508 A | 7/1997 | Yaghi | |
| 6,624,318 B1 | 9/2003 | Mueller et al. | |
| 6,893,564 B2 | 5/2005 | Mueller et al. | |
| 6,929,679 B2 | 8/2005 | Muller et al. | |
| 6,930,193 B2 | 8/2005 | Yaghi et al. | |
| 6,965,026 B2 | 11/2005 | Zaworotko et al. | |
| 7,169,957 B2 | 1/2007 | Atwood et al. | |
| 7,196,210 B2 | 3/2007 | Yaghi et al. | |
| 7,279,517 B2 | 10/2007 | Mueller et al. | |
| 2003/0222023 A1 | 12/2003 | Mueller et al. | |
| 2006/0287190 A1 | 12/2006 | Eddaoudi et al. | |
| 2008/0040984 A1 | 2/2008 | Lanahan | |

OTHER PUBLICATIONS

Liu et al., Chem. Eur. J., vol. 13, pp. 8953-8959 (2007).*
Nouar et al., "Supermolecular Building Blocks (SBBs) for the Design and Synthesis of Highly Porous Metal-Organic Frameworks," J. Am. Chem. Soc. 2008, 130, 1833-1835.
Yang Zou et al., "A Designed Metal-Organic Framework Based on a Metal-Organic Polyhedron," Chem. Commun. 2008, 2340-2342.
Brandt J. et al., "Single-Metal-Ion-Based Molecular Building Blocks (MBBs) Approach to the Design and Synthesis of Metal-Organic Assemblies," J. Mol. Struct. 2006, 796, 160-164.
Cairns, A. et al., "Supermolecular Building Blocks (SBBs) and Crystal Design: 12-Connected Open Frameworks Based on a Molecular Cubohemioctahedron," J. Am. Chem. Soc. 2008, 1560-1561, 130.
Caulder, D. et al., "Supermolecules by Design," Acc. Chem. Res. 1999, 32, 975-982.
Cheetham A. et al., "Open-Framework Inorganic Materials," Agnew Chem., Int. Ed. 1999, 38, 3268-3292.

(Continued)

*Primary Examiner* — Porfirio Nazario Gonzalez
(74) *Attorney, Agent, or Firm* — Bryan Cave LLP

(57) ABSTRACT

The present invention generally relates to supramolecular assemblies and their modes of synthesis. The supramolecular assemblies include a 1:8 ratio of a supermolecular polyhedral building block and a triangular molecular building block, the supermolecular polyhedral building block having points of extension corresponding to the vertices of a rhombicuboctahedron for linking the supermolecular polyhedral building block to the triangular building block.

31 Claims, 16 Drawing Sheets

OTHER PUBLICATIONS

Chui S. et al., "A Chemically Functionalizable Nanoporous Material [Cu3(TMA)2(H2O)3]n," Science 1999, 283, 1148-1150.

Delgado-Friedrichs, O. et al., "Three-Periodic Nets and Tilings: Edge-Transitive Binodal Structures," Acta Cryst. 2006, A62, 350-355.

Delgado-Friedrichs, O. et al., "Three-Periodic Tilings and Nets: Face-Transitive Tilings and Edge-Transitive Nets Revisited," Acta Cryst. 2007, A63, 344-347.

Demko, Z., et al., "Preparation of 5-Substituted 1H-Tetrazoles From Nitriles in Water," J. Org. Chem. 2001, 66, 7945-7950.

Desiraju, G. et al., "Chemistry Beyond the Molecule," Nature 2001, 412, 397-400.

Dinca, M. et al., "Observation of Cu2+-H2 Interactions in a Fully Desolvated Sodalite-Type Metal-Organic Framework," Agnew. Chem. Int. Ed. 2007, 46, 1419-1422.

Dinca, M. et al., "High-Enthalpy Hydrogen Adsorption in Cation-Exchanged Variants of the Microporous Metal-Organic Framework Mn[(MnCl)(BTT)(CHOH)]," J. Am. Chem. Soc. 2007, 129, 11172-11176.

Eddaoudi, M. et al., "Modular Chemistry: Secondary Building Units as a Basis for the Design of Highly Porous and Robust Metal-Organic Carboxylate Frameworks," Acc. Chem. Res. 2001, 34, 319-330.

Eddaoudi, M. et al., "Porous Metal-Organic Polyhedra: 25 A Cuboctahedron Constructed from 12 Cu(CO) Paddle-Wheel Building Blocks," J. Am. Chem. Soc. 2001, 123, 4368-4369.

Eddaoudi, M. et al., "Systematic Design of Pore Size and Functionality in Isoreticular MOFs and Their Application in Methane Storage," Science 2002, 295, 469-472.

Ferey, G. J. et al., "Building Units Design and Scale Chemistry," J. Solid State Chem. 2000, 152, 37-48.

Hayashi, H. et al., "Zeolite A Imidazolate Frameworks," Nat. Mater. 2007, 6, 501-506.

Hoskins, B. et al., "Design and Construction of a New Class of Scaffolding-Like Materials Comprising Infinite Polymeric Frameworks of 3D-linked Molecular Rods. A Reappraisal of the Zinc Cyanide and Cadmium Cyanide Structures and the Synthesis and Structure of the Diamond-Related Frameworks [N(CH3)4][CuIZnII(CN)4] and CuI [4,4',4'',4'''-Tetracyanotetraphenylmethane]BF4.xC6H5NO2," J. Am. Chem. Soc., 1990, 112, 1546-1554.

Kitagawa, S. et al., "Functional Porous Coordination Polymers," Agnew. Chem. Int. Ed. 2004, 43, 2334-2375.

Li, H. et al., "Design and Synthesis of an Exceptionally Stable and Highly Porous Metal-Organic Framework," Nature 1999, 402,276-279.

Liu, Y. et al., "Assembly of Metal-Organic Frameworks (MOFs) Based on Indium-Trimer Building Blocks: A Porous MOF with Soc Topology and High Hydrogen Storage," Agnew. Chem. Int. Ed. 2007, 46, 3278-3283.

Liu, Y. et al., "Molecular Building Blocks Approach to the Assembly of Zeolite-Like Metal-Organic Frameworks (ZMOFs) with Extra-Large Cavities," Chem. Commun. 2006, 14, 1488-1490.

Liu, Y. et al., "4-Connected Metal-Organic Assemblies Mediated via Heterochelation and Bridging of Single Metal Ions: Kagome Lattice and the ML Octahedron," J. Am. Chem. Soc. 2005, 127, 7266-7267.

Mezei, G. et al., "First Structural Characterization of a Delocalized, Mixed-Valent, Triangular Cu Species: Chemical and Electrochemical Oxidation of a Cu Pyrazolate and Electronic Structure of the Oxidation Product," Inorg. Chem. 2005, 44, 7271-7273.

Moulton, B. et al., "Nanoballs: Nanoscale Faceted Polyhedra With Large Windows and Cavities," Chem. Commun. 2001, 863-864.

Moulton, B. et al., "From Molecules to Crystal Engineering: Supermolecular Isomerism and Polymorphism in Network Solids," Chem. Rev. 2001, 101,1629-1658.

Mulfort, K. et al., "Chemical Reduction of Metal-Organic Framework Materials as a Method to Enhance Gas Uptake and Binding," J. Am. Chem. Soc. 2007, 129, 9604-9605.

Nouar, F. et al., "Supermolecular Building Blocks (SBBs) for the Design and Synthesis of Highly Porous Metal-Organic Frameworks," J. Am. Chem. Soc. 2008, 130, 1833-1835.

Ockwig, N. et al., "Reticular Chemistry: Occurrence and Taxonomy of Nets and Grammar for the Design of Frameworks," Acc. Chem. Res. 2005, 38, 176-182.

Perry,V. et al., "Bottom Up Synthesis That Does Not Start At the Bottom: Quadruple Covalent Cross-Linking of Nanoscale Faceted Polyhedra," J. Am. Chem. Soc. 2007, 129, 10076-10077.

Ritzen, A. et al., "Chiral, Polyionic Dendrimers With Complementary Charges—Synthesis and Chiroptical Properties," Eur. J. Org. Chem. 2000, 3771-3782.

Roswell, J. et al., "Effects of Functionalization, Catenation, and Variation of the Metal Oxide and Organic Linking Units on the Low-Pressure Hydrogen Adsorption Properties of Metal-Organic Frameworks," J. Am. Chem, Soc. 2006, 128, 1304-1315.

Seidel, S. et al., "High-Symmetry Coordination Cages via Self-Assembly," Acc. Chem. Res., 35, 972-983.

Seo, J. et al., "A Homochiral Metal-Organic Porous Material for Enantioselective Separation and Catalysis," Nature 2000, 404, 982-986.

Takeda, N., "A Nanometre-Sized Hexahedral Coordination Capsule Assembled From 24 Components," Nature 1999, 398, 794-796.

Spek, A., "Platon, An Integrated Tool for the Analysis of the Results of a Single Crystal Structure Determination," Acta Cryst. 1990, A46, c34.

Sudik, A., "A Metal-Organic Framework with a Hierarchical System of Pores and Tetrahedral Building Blocks," Agnew. Chem. Int. Ed. 2006, 45, 2528-2533.

Tominaga, M. et al., "Finite, Spherical Coordination Networks that Self-Organize from 36 Small Components," Agnew. Chem. Int. Ed. 2004, 43, 5621-5625.

Wang, Z. et al., "Ternary Nets Formed by Self-Assembly of Triangles, Squares, and Tetrahedra," Agnew. Chem. Int. Ed. 2005, 44, 2877-2880.

Yaghi, O. et al., "Design of Solids from Molecular Building Blocks: Golden Opportunities for Solid State Chemistry," J. Solid State Chem. 2000, 152, 1-2.

Yaghi, O. et al., "Reticular Synthesis and the Design of New Materials," Nature 2003, 423, 705-714.

Zou, Y. et al., "A Designed Metal-Organic Framework Based on a Metal-Organic Polyhedron," Chem. Commun. 2008, 2340-2342.

Zhai, Q. et al., "Design of Novel Three-Dimensional Coordination Polymers Based on Triangular Trinuclear cooper 1, 2, 4-Triazolate Units," Cryst. Growth Des. 2006, 6, 1393-1398.

Stein, A. et al., "Turning Down the Heat: Design and Mechanism in Solid-State Synthesis," Science 1993, 259, 1558-1564.

Holden, A. et al., "Shapes, Space and Symmetry," 1971, 94.

* cited by examiner

SUPRAMOLECULAR ASSEMBLIES AND BUILDING BLOCKS

CROSS-REFERENCE TO RELATED APPLICATIONS

This application claims the benefit of U.S. Provisional Application Ser. No. 60/988,195, filed Nov. 15, 2008, which is hereby incorporated by reference in its entirety, including any figures, tables, and drawings.

BACKGROUND

The present invention generally relates to supramolecular assemblies, and their modes of synthesis.

Design principles that are based upon the concepts of crystal engineering and self-assembly have recently afforded new classes of crystalline solids that possess important physical properties such as bulk magnetism or porosity. Large-scale molecular networks have been developed to encapsulate other materials and these are playing an ever-increasing role in the pharmaceutical industry and as materials for sensors, and liquid crystals. In addition, with the inclusion of metals within the structures, the large polymers formed by these crystals can possess, among other properties, catalytic, fluorescent, and magnetic attributes.

The molecular/supermolecular building block (MBB/SBB) approach has recently emerged as a powerful strategy for the design and construction of solid-state materials. This is evidenced by the burgeoning academic and industrial interest in the class of materials known as metal-organic frameworks (MOFs), for which desired functionality can be introduced at the molecular level prior to the assembly process. See, e.g., Stein et al., Science 1993, 259, 1558-1564; Férey, G., J. Solid State Chem. 2000, 152, 37-48; Eddaoudi et al., Science 2002, 295, 469-472; Kitagawa et al., Angew. Chem. Int. Ed. 2004, 43, 2334-2375; Moulton et al., Chem. Rev. 2001, 101, 1629-1658; Eddaoudi et al., Acc. Chem. Res. 2001, 34, 319-330; and U.S. Pat. No. 6,624,318 (hereby incorporated by reference herein in its entirety).

Assembly of finite supramolecular polyhedra and periodic extended networks from MBBs and SBBs offers great potential for the rational design and synthesis of functional materials and nanostructures. Cheetham et al., Angew. Chem., Int. Ed. 1999, 38, 3268-3292; Yaghi et al., Nature 2003, 423, 705-714; Seo et al., Nature 2000, 404, 982-986; and Desiraju et al., Nature 2001, 412, 397-400. This approach has been explored and, to some extent, has proven to be successful in metal-ligand directed assembly. See, e.g., Moulton et al., supra; Hoskins et al., J. Am. Chem. Soc. 1990, 112, 1546-1554; Seidel et al., Acc. Chem. Res. 2002, 35, 972-983; Takeda et al., Nature 1999, 398, 794-796; Kitagawa et al., supra; Eddaoudi et al., supra; Caulder et al., Acc. Chem. Res. 1999, 32, 975-982; Yaghi et al., supra. Metal-carboxylate based clusters, where metals are locked into their positions, have been synthesized in situ and successfully used as rigid directional secondary building units (SBUs) to design and construct stable open metal organic assemblies that maintain their structural integrity even upon complete removal of their guest molecules. See Li et al., Nature 1999, 402, 276-279; Chui et al., Science 1999, 283, 1148-1150, Yaghi et al., supra; and Yaghi et al., J. Solid State Chem. 2000, 152, 1-2.

Conventional MBBs and SBBs (coordination clusters or organic ligands) with varied connectivity and specific geometry and directionality are readily accessible, and can be employed to access structures where the MBBs and SBBs augment the vertices of a given net. See Ockwig et al., Acc. Chem. Res. 2005, 38, 176-182; Liu et al., J. Am. Chem. Soc. 2005, 127, 7266-7267; Brant et al., J. Mol. Struct. 2006, 796, 160-164; and Liu et al., Chem. Commun. 2006, 14, 1488-1490. Nevertheless, it is an ongoing challenge to absolutely predict the network topology of the constructed MOF. Accordingly, the ability to target nets that are exclusive for a combination of building blocks presents greater potential towards prediction, design, and synthesis of the resultant framework in crystal chemistry, and with a high degree of control over structure and functionality.

SUMMARY OF THE INVENTION

Among the various aspects of the present invention is the provision of supramolecular assemblies, and building blocks for the preparation of such assemblies. Advantageously, the building blocks may be used to form a (3,24)-connected rht net that may be used, for example, in the practice of isoreticular chemistry, where higher surface areas and larger free pore volumes can be readily achieved.

Briefly, therefore, the present invention is directed to a supramolecular assembly comprising a 1:8 ratio of a supermolecular polyhedral building block and a triangular molecular building block. The supermolecular polyhedral building block has points of extension corresponding to the vertices of a rhombicuboctahedron (and other regular polyhedra that have 24 vertices and the edge skeleton shared by small rhombihexahedron, small cubicuboctahedron, and rhombicuboctahedron) for linking the supermolecular polyhedral building block to the triangular building blocks. In the assembly, an individual supermolecular polyhedral building block is linked to twenty-four different triangular building blocks and an individual triangular building block is linked to three different supermolecular polyhedral building blocks with the linkages comprising covalent bonds, coordinate covalent bonds, noncovalent bonds, or a combination thereof.

Another aspect of the invention is a ligand for forming a supramolecular assembly corresponding to Formula (2):

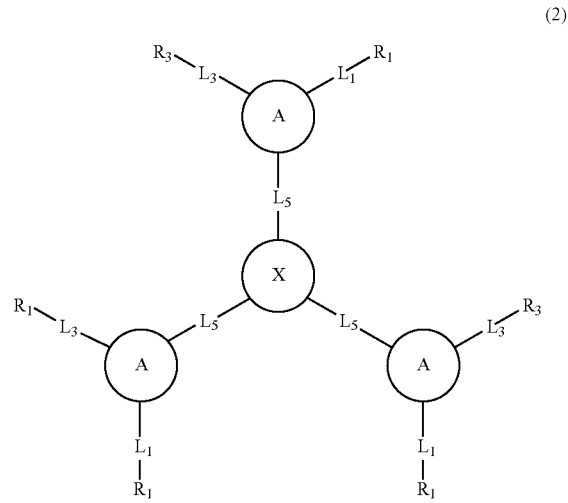

(2)

wherein the X ring comprises a monocyclic ring or polycyclic fused ring system, or has the formula:

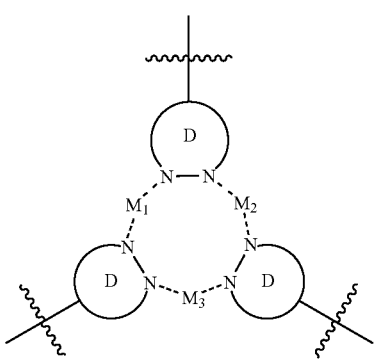

each A ring is a monocyclic ring or polycyclic fused ring system;

each $L_1$ and $L_3$ is a linker moiety;

each $L_5$ is a linker moiety;

each $R_1$ and $R_3$ is a functional group capable of coordinately bonding to at least one metal;

each D ring is a monocyclic ring or a polycyclic fused ring system;

$M_1$, $M_2$, and $M_3$ are independently metal ions; and the dashed lines represent coordination between the nitrogen atom of a D ring and a metal.

Another aspect of the invention is a process for the preparation of a supramolecular assembly. The process comprises combining a metal source and a ligand to generate a composition comprising a 1:8 ratio of a supermolecular polyhedral building block and a triangular molecular building block, the supermolecular polyhedral building block having points of extension corresponding to the vertices of a rhombicuboctahedron for linking the supermolecular polyhedral building block to the triangular building blocks wherein an individual supermolecular polyhedral building block is linked to twenty-four different triangular building blocks and an individual triangular building block is linked to three different supermolecular polyhedral building blocks, the linkages comprising covalent bonds, coordinate covalent bonds, noncovalent bonds, or a combination thereof.

Other objects and features will be in part apparent and in part pointed out hereinafter.

DETAILED DESCRIPTION

Figures 1A, 1B, 1C:
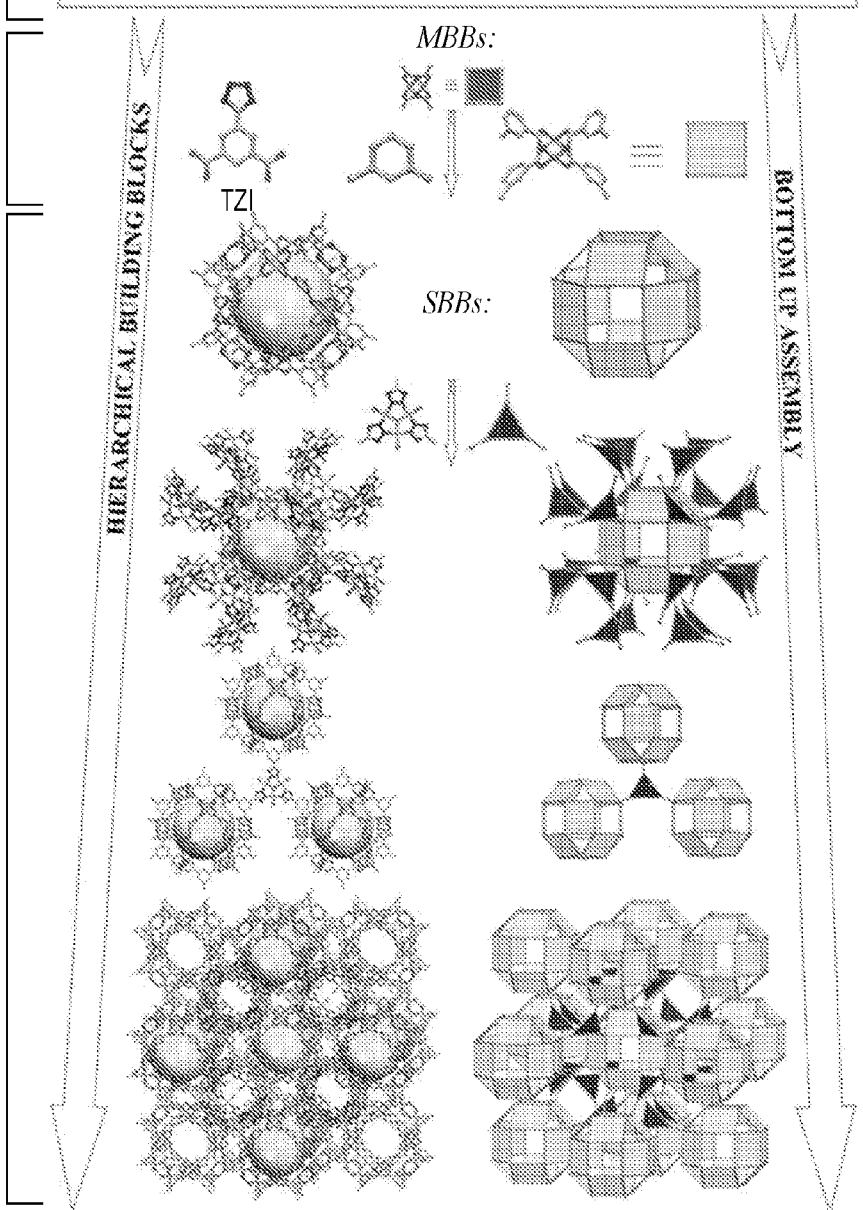
FIG. 1A illustrates the (3,24)-connected rht net and the two vertices and corresponding vertex figures when augmented.
FIG. 1B illustrates select fragments from the crystal structure of [1]. C=gray, N=blue, O=red, Cu=green; the 5-position of the 1,3-BDC ligand is highlighted in orange; the yellow spheres indicate the cavity of the truncated cuboctahedra; some spheres, all solvent molecules, and all hydrogen atoms have been omitted for clarity.
FIG. 1C is a schematic showing the corresponding strategy from MBBs to SBBs (generated all together in situ) to MOF.

In accordance with one aspect of the present invention, supramolecular assemblies are provided in the form a (3,24)-connected rht net. These nets comprise a supermolecular building block and a triangular building block.

In general, the supramolecular assembly comprises a 1:8 ratio of the supermolecular polyhedral building blocks and the triangular molecular building blocks. The supermolecular polyhedral building blocks have points of extension corresponding to the vertices of a rhombicuboctahedron (and other regular polyhedra that have 24 vertices and the edge skeleton shared by small rhombihexahedron, small cubicuboctahedron, and rhombicuboctahedron) for linking the supermolecular polyhedral building blocks to the triangular building blocks. In the assembly, an individual supermolecular polyhedral building block is linked to twenty-four different triangular building blocks and an individual triangular building block is linked to three different supermolecular polyhedral building blocks with the linkages comprising covalent bonds, coordinate covalent bonds, noncovalent bonds, or a combination thereof.

In a preferred embodiment, the supermolecular building block comprises molecular building blocks (MBB), that is, a molecular or ionic chemical species that has the ability to extend through covalent or noncovalent linking. The points of extension of the MBB define a geometric building unit that is equivalent to augmenting a node in an infinite 1D, 2D or 3D network or polyhedron and thereby becomes a means of designing and generating an inorganic, organic or metal-organic material. Being constructed from molecular building blocks, supermolecular building block (SBB) represents the next highest level of hierarchy. Some or all of the points of extension of the SBB define a geometric building unit that becomes a means of designing and generating an inorganic, organic or metal-organic material with a larger relative scale and a higher degree of connectivity than that which can be obtained from an MBB.

In general, the supermolecular building block may be derived from any molecular building block that assembles to form a polyhedron that has twenty-four vertices and the edge skeleton of the rhombicuboctahedron. As described in greater detail below, in one embodiment, the assembly is a metal organic framework comprising copper or other metal and a ligand.

The triangular building blocks are used to link the supermolecular building blocks, with each triangular building block being linked to three different supermolecular building blocks. The triangular building blocks thus contain three arms, or points of attachment, for the three supermolecular building blocks with the arms, or points of attachment, being substantially in one plane. Like the supermolecular building blocks, the triangular building blocks may be assembled, in situ, by the assembly of a ligand and a metal. Alternatively, the triangular building blocks may be pre-assembled as a component of a tritopic or trimer-type ligand.

In accordance with one aspect of the present invention, the supermolecular building blocks and the triangular building blocks of the assembly may be derived from one or more monomer ligands, one or more trimer ligands, or a combination thereof. In general, the supermolecular building blocks and the triangular building blocks may be derived from different ends of the same ligand(s). For example, when the metal is copper and the ligand is 5-tetrazolylisophthalic acid, the carboxylate end of the ligand coordinates with metal to form the supermolecular building block and the tetrazolyl end of the ligand coordinates with copper to form the triangular building block. More specifically, two copper metal ions coordinate to eight oxygen atoms of four carboxylates to form a square building block with the 5-position of the isophthalate ligand sitting directly on the twenty-four vertices of a rhombicuboctahedron. In addition, each tetrazolyl moiety coordinates in a bis-monodentate fashion to two copper atoms, with each of the copper atoms, in turn, coordinated to two nitrogen atoms (one from each of two tetrazolates) to form a $Cu_3O$ $(N_4CR)_3$ trimer.

In an alternative embodiment, the ligand is a tritopic or trimer-type ligand and the supermolecular building blocks are derived from the three ends of the ligand and the triangular building block is derived from the central core of the ligand. For example, when the ligand is 5,5',5''-[1,3,5-phenyltri(methoxy)]tri-methylisophthalate, i.e., a compound having three isophthalate nodes positioned at the 1, 3, and 5 positions at 120° bond angles around a trimethoxylene-substituted phenyl core (see Example 7), the isophthalate node, and particularly the dicarboxylate ends, coordinate with two metals to form the supermolecular building block and the trimethoxylene-substituted phenyl core of the ligand forms the triangular building block. As in the previous embodiment, two copper metal ions coordinate to eight oxygen atoms of four carboxylates in a square pyramidal geometry to form a truncated cuboctahedron with the 5-position of each isophthalate ligand sitting directly on the twenty-four vertices of a rhombicuboctahedron. In addition, the triangular building block comprising the trimethoxylene-substituted phenyl core acts as an organic bridging moiety, connecting three supermolecular building blocks derived from the three isophthalate nodes of the ligand. According to this embodiment, therefore, the triangular molecular building block is pre-formed as a component of the trimer ligand. By way of another example, the triangular molecular building block can be an organic moiety such a trimesic acid (i.e., benzene-1,3,5-tricarboxylic acid) which forms hydrogen bonds with the ligands that form the supermolecular building blocks.

The present invention is directed to supramolecular assemblies that include particular combinations of building blocks. Advantageously, the building blocks described herein provide a greater potential for the prediction, design, and synthesis of the resultant network topology of a constructed metal-organic, or organic (i.e., non-metal), framework. The nets, frameworks, and assemblies described herein utilize metal-organic or organic polyhedra, i.e., supermolecular building blocks constructed from metal-organic or organic polygons, in combination with other molecular building blocks, which can be externally functionalized, as building blocks for edge transitive nets that are unique, specifically nets where the vertex figures indicate the need for high connectivity. As simple molecular building blocks with connectivity greater than or equal to 8 are often too intricate to systematically obtain by means of organic ligands or multinuclear clusters, such structures can only be designed by utilizing molecular and supermolecular building blocks with a high degree of symmetry and connectivity, i.e., with enhanced directional and structural information is already built in. In principle, there is a degree of predictability in the building blocks described herein that is not present with basic molecular building blocks.

The present invention provides, for example, supermolecular polyhedral building blocks, generated in situ, as building units. As described herein, these supermolecular building blocks are assemblies, preferably metal-organic assemblies, that can be used in combination with triangular molecular building blocks to construct (24-connected)-based supramolecular assemblies. In certain embodiments, the supermolecular building block includes twelve metal (e.g., copper) paddlewheels joined by twenty four ligand moieties designed to contain three functional groups or substituent arms positioned at 120° bond angles. Preferably, the 5-position of the bent bridging ligand (120° angle) lies on the vertices of a rhombicuboctahedron, the 24-connected vertex figure for the (3,24)-connected rht net. Thus, functionalization at this 5-position with an organic moiety that permits the formation of a rigid triangular building block, leads to the formation of an assembly having an rht-like network topology, since this (3,24)-connected net is the only edge transitive net known for the assembly of 24- and 3-connected vertices.

In addition to the connected assemblies, the present invention provides triangular building blocks for use in constructing the supramolecular assemblies, with the triangular molecular building block structures being formed from ligands (monomer and trimers). The ligands can be further employed in the formation of the supermolecular polyhedral building blocks, in the form of metal-organic and organic (i.e., non-metal) polyhedra. The present disclosure also relates to the utilization of certain ligand compounds and their use in the preparation of triangular molecular building blocks and supermolecular building blocks via metal coordination and/or bridging. The molecular and supermolecular building block structures described herein are employed in design and synthesis of metal-organic assemblies and other polyhedric assemblies, both discrete and extended.

The building blocks described herein are well-suited for the formation of supramolecular building blocks having unique, edge-transitive nets, and specifically nets where the vertex figures indicate the need for high connectivity. Since relatively simple molecular building blocks with connectivity of greater than or equal to about 8 are highly intricate and difficult to systematically obtain by means of organic ligands or multinuclear clusters, such structures typically can only be designed by utilizing supermolecular building blocks with a high degree of symmetry and connectivity; that is, enhanced directional and structural information is already built in.

Advantageously, the subject disclosure also provides strategies and pathways for the design and synthesis of rigid triangular molecular building blocks and supermolecular building blocks, formed from monomer ligands or from trimer ligands comprising three ligand monomers, which may be combined to form porous materials with large and tunable cavities. Specifically, materials having rht topologies and containing organic and metal constituents in their framework are provided. In certain preferred embodiments, a metal-ligand directed assembly approach is used to assemble rigid building blocks with the commensurate geometry into expanded porous and non-porous metal-organic frameworks.

One of multiple complementary key steps suitable for the logical synthesis of metal-organic and organic (i.e., non-metal) based assemblies is the ability to control the coordination number and thus geometry of inorganic and organic building units. Inorganic and organic building blocks formed using the components described herein can be judiciously predesigned to contain the required geometrical information and directional binding functionalities to facilitate the attainment of a predetermined structure. The approach of the present invention to the design and synthesis of robust metal-organic and organic (i.e., non-metal) assemblies is based on a particular combination of supermolecular polyhedral building blocks and triangular molecular building blocks, to form a supramolecular assembly comprising a 1:8 ratio of the former to the latter.

Construction of extended Archimedean and Platonic solids from supermolecular polyhedral building blocks and triangular molecular building blocks under relatively mild conditions offers the ability to impart the desired functions and/or properties in the as-synthesized compound.

The disclosed class of metal/non-metal organic-containing monomer and trimer ligand subunits is unique due to their ability to form supermolecular and molecular building blocks, which themselves can be regarded as a subunit of metal-organic and organic frameworks and assemblies. The dual composition (periodic distribution of the organic and inorganic components) of the disclosed materials and their extra-large cavities, among other properties, offer great potential for their use in areas such as separation, controlled release and/or sequestration of gases (e.g., carbon dioxide, nitrogen, hydrogen, rare gases, and the like), separation controlled release and/or sequestration of small, medium and large molecules or ions (e.g., toxins, pollutants, pesticides, active pharmaceutical ingredients, biomolecules/enzymes, metal cations or clusters, and the like), catalysis, magnetic materials, semi-conducting materials, chemosensors, biosensors, purification of chiral molecules or ions, among other applications.

Ligand Compounds

Among other things, the present disclosure provides ligand compounds. The ligand compounds of the invention can be used as monomers in the preparation of supermolecular building blocks, and optionally, the supermolecular and the triangular molecular building blocks. In general, the compounds include at least one monocyclic or polycyclic fused ring moiety substituted in such a way that each of three substituent arms is oriented about 120° from each other. Remaining positions on the monocyclic or polycyclic fused ring moiety may also be substituted, provided that these groups do not affect the ~120° bond angles of the three substituent arms.

The ligand compounds may be used, per se, to coordinate with metals (including metal ions and metal oxides). The ligand compounds can be assembled to form the supermolecular building blocks. In certain embodiments, however, three ligand compounds are assembled to form a trimer ligand, which may be used in the preparation of both supermolecular building blocks and triangular molecular building blocks; that is, one portion of the trimer forms, in part, the supermolecular building block, while another portion of the trimer forms, in part, the triangular molecular building blocks. The supermolecular building blocks and triangular molecular building blocks formed from such monomers and/or trimers, in combination, form metal organic frameworks, as discussed in further detail herein. In particular, the ligand compounds and ligand trimers described herein are useful in the preparation of supramolecular assemblies having rht topologies or nets.

Monomer Ligands

In one embodiment, the ligand compound corresponds to Formula (1):

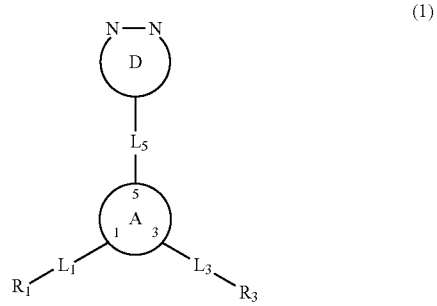

wherein
A is a monocyclic ring or polycyclic fused ring system;
each $L_1$ and $L_3$ is a linker moiety;
$L_5$ is a linker moiety;
each $R_1$ and $R_3$ is a functional groups capable of coordinately bonding to at least one metal ion; and
the D ring is a monocyclic ring or polycyclic fused ring system.

As discussed in further detail herein, a plurality of ligand compounds corresponding to Formula (1) may form the supermolecular building block, and/or three monomer ligand compounds corresponding to Formula (1) above may together form a trimer, portions of which may be used in the formation of supermolecular polyhedral building blocks and other portions of which may be used in the formation of a triangular molecular building block, and the combination of supermolecular and molecular building blocks may further assemble to form supramolecular building blocks, and metal organic frameworks.

The A Ring

Among a variety of substituents and moieties, the ligand compounds of Formula (1) above include the A ring, a monocyclic or polycyclic fused ring system capable of being substituted such that each at least three substituents of the monocyclic or polycyclic ring system are positioned about 120 degrees from each other:

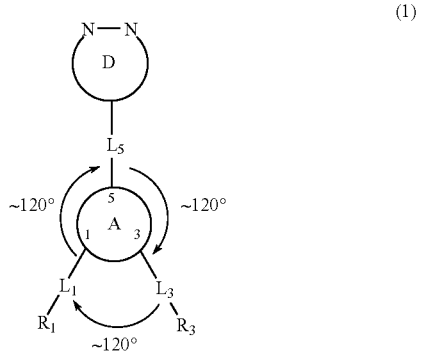

Preferably, the substituent at the 5-position of the A ring lies on the vertices of a regular convex polyhedron having 24 vertices and an edge skeleton shared by (1) a small rhombicuboctahedron; (2) a rhombicuboctahedron; or (3) a small cubicuboctahedron, the 24-connected vertex figure for a (3,24)-connected rht net.

In general, the A ring may be any saturated or unsaturated carbocyclic or heterocyclic ring structure. The A ring may be monocyclic, or may be a bicyclic, tricyclic, hexacyclic, or otherwise polycyclic ring system, provided that the polycyclic ring system is capable of being substituted in the manner described and illustrated above (i.e., with at least three substituent arms positioned about 120° from each other). In one embodiment in which the A ring is a polycyclic ring system, the A ring has the structure:

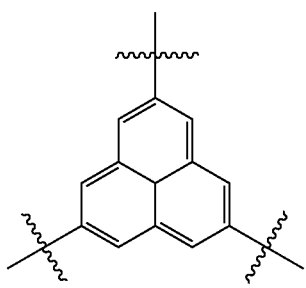

wherein the wavy lines represent the attachment point of the A ring to the remainder of the ligand compound (i.e., at $L_1$, $L_3$, or $L_5$ of each substituent arm)

In certain embodiments, the A ring is a six-membered ring moiety. In general, the six-membered A ring may be any saturated or unsaturated six-membered carbocyclic or heterocyclic ring structure capable of being substituted at the 1, 3, and 5 positions, such that each substituent is ~120° from each other (as illustrated in the diagram above). Cationic forms of the carbocyclic or heterocyclic A ring are also contemplated; that is, a free electron pair of a carbon or heteroatom may be involved in the skeletal bonding of the ring system, e.g., in the formation of the ring or in the double bond system of the ring.

In one preferred embodiment, the A ring is a six-membered carbocyclic or heterocyclic ring having the structure:

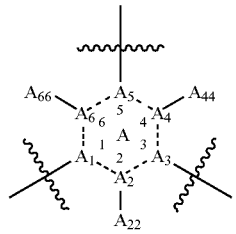

wherein the atoms defining the ring, $A_1$, $A_2$, $A_3$, $A_4$, $A_5$, and $A_6$, are independently selected from carbon, nitrogen, oxygen, boron, and sulfur atoms (including cations thereof);

the $A_1$, $A_3$, and $A_5$ ring atoms are substituted with the $-L_1-R_1$, $-L_3-R_3$, and $-L_5-D$ ring moieties, respectively, which are positioned about 120° from each other (as described in connection with Formula (1));

$A_{22}$, $A_{44}$, and $A_{66}$ are any atom or group of atoms that do not otherwise affect the ~120° bond angles of the $A_1$, $A_3$, and $A_5$ substituent arms;

the dashed lines represent single or double bonds, or collectively form a conjugated bond system that is unsaturated to a degree of aromaticity;

and the wavy lines represent the attachment point of the A ring to the remainder of the ligand compound (i.e., at $L_1$, $L_3$, or $L_5$ of each substituent arm).

In general, the $A_{22}$, $A_{44}$, and $A_{66}$ substituents are selected such that they will not adversely affect other substituents on the ligand compound and/or will not affect assembly of the desired monomer and trimer ligands and further assembly of the supermolecular building blocks and/or portions of the triangular molecular building blocks; in particular, the $A_{22}$, $A_{44}$, and $A_{66}$ substituents are preferably selected such that they do not affect the 120° bond angles of the $A_1$, $A_3$, and $A_5$ substituent arms as described above. Suitable substituents for $A_{22}$, $A_{44}$, and $A_{66}$ include, for example, one or more of the following chemical moieties: —H, —OH, —OR, —COOH, —COOR, —CONH$_2$, —NH$_2$, —NHR, —NRR, —SH, —SR, —SO$_2$R, —SO$_2$H, —SOR, and halo (including F, Cl, Br, and I), wherein each occurrence of R may be hydrocarbyl or substituted hydrocarbyl (e.g., substituted or unsubstituted alkyl, substituted or unsubstituted aryl, or substituted or unsubstituted araklyl).

The A ring may be, for example, a six-membered aromatic ring. Alternatively, the A ring may be a six-membered non-aromatic ring. In one embodiment, for example, the six-membered A ring is selected from benzene, pyridine, pryridinium, pyrimidine, pyrimidinium, triazine, triazinium, pyrylium, boroxine, diborabenzene, and triborabenzene rings. Thus, for example, the A ring may correspond to one of the following exemplary six-membered rings:

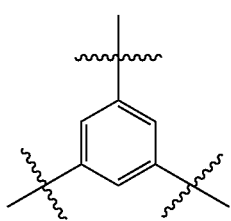 (A₁)
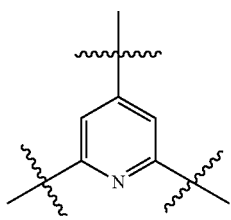 (A₂)
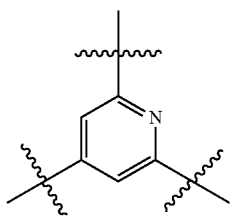 (A₃)
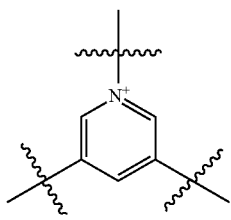 (A₄)
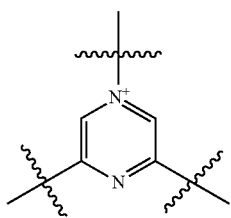 (A₅)
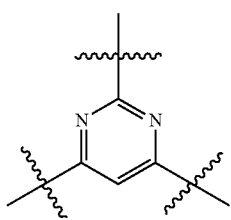 (A₆)
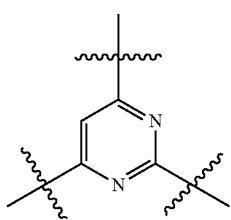 (A₇)
-continued
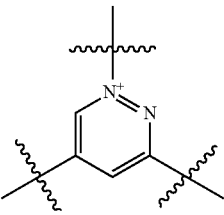 (A₈)
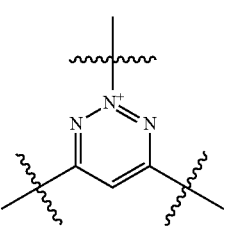 (A₉)
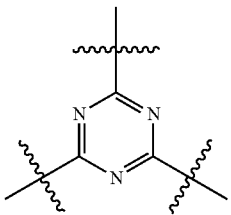 (A₁₀)
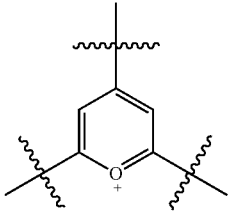 (A₁₁)
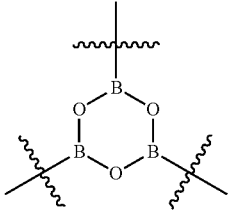 (A₁₂)
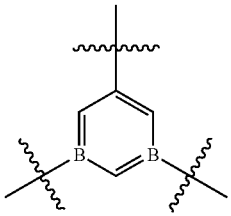 (A₁₃)
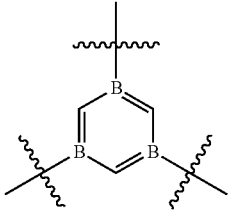 (A₁₄)

wherein the wavy lines represent the attachment point of the A ring to the remainder of the ligand compound corresponding to Formula (1) (i.e., at $L_1$, $L_3$, or $L_5$ of each substituent arm).

In one embodiment, the A ring is a benzene, boroxine, or triazine ring. According to this embodiment, therefore, the A ring is selected from:

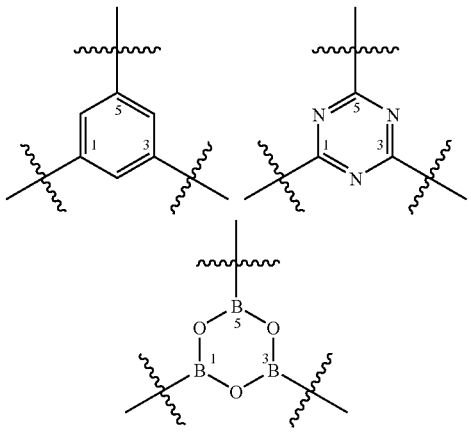

wherein the wavy lines represent the attachment point of the A ring to the remainder of the ligand compound corresponding to Formula (1) (i.e., at $L_1$, $L_3$, or $L_5$ of each substituent arm). In one preferred embodiment, the A ring is a benzene ring. According to this embodiment, therefore, the A ring has the formula:

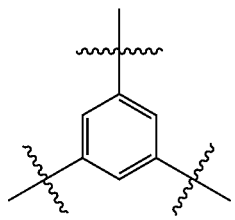

wherein the wavy lines represent the attachment point of the benzene ring to the remainder of the ligand compound corresponding to Formula (1) (i.e., at $L_1$, $L_3$, or $L_5$ of each substituent arm).

The D Ring

In addition to the A ring, the ligand compounds corresponding to Formula (1) also include the D ring. The D ring portion of the ligand compounds may be used, for example, in the construction of the supermolecular building block and/or in the construction of the triangular molecular building block. The D ring portion of the ligand compound may be used, for example, in the construction of the triangular molecular building block, where, for example, three D-ring portions of a trimer combine to form the triangular molecular building block, with the remainder of each node of the trimer forming a portion of the supermolecular building block.

In general, the D ring is a monocyclic or bicyclic fused ring system configured such that the two nitrogen atoms of the ring structure are oriented in positions shown in connection with the structure of Formula (1). This configuration enables the two nitrogen atoms to coordinate in a bis-monodentate fashion to two metal atoms to form the triangular molecular building blocks as described elsewhere herein.

Typically, the D ring has one of the two following structures:

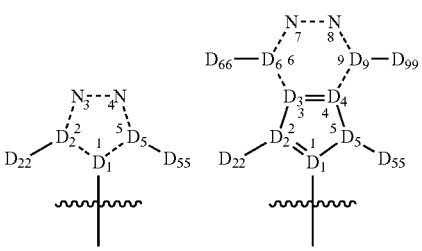

wherein the atoms defining the ring (with the nitrogen atoms), $D_1$, $D_2$, and $D_5$, or $D_1$, $D_2$, $D_3$, $D_4$, $D_5$, $D_6$, and $D_9$, are independently selected from carbon, nitrogen, oxygen, boron, and sulfur atoms (including cations thereof);

$D_{22}$, $D_{55}$, $D_{66}$, and $D_{99}$ are generally any atom or group of atoms that do not otherwise affect the coordination of the ring nitrogen atoms to one or more metal ions;

the dashed lines represent single or double bonds, or collectively form a conjugated bond system that is unsaturated to a degree of aromaticity; and the wavy lines represent the attachment point of the D ring to the remainder of the ligand compound (i.e., at $L_5$).

In general, the $D_{22}$, $D_{55}$, $D_{66}$, and $D_{99}$ substituents are selected such that they will not adversely affect other substituents on the ligand compound and/or will not affect assembly of the desired trimer ligand and further assembly of the supermolecular building blocks and/or portions of the triangular molecular building blocks; in particular, the $D_{22}$, $D_{55}$, $D_{66}$, and $D_{99}$ substituents are preferably selected such that they do not affect the coordination of the ring nitrogen atoms of the D ring to one or more metal ions. Suitable substituents for $D_{22}$, $D_{55}$, $D_{66}$, and $D_{99}$ include, for example, one or more of the following chemical moieties: —H, —OH, —OR, —COOH, —COOR, —CONH$_2$, —NH$_2$, —NHR, —NRR, —SH, —SR, —SO$_2$R, —SO$_2$H, —SOR, and halo (including F, Cl, Br, and I), wherein each occurrence of R may be hydrocarbyl or substituted hydrocarbyl (e.g., substituted or unsubstituted alkyl, substituted or unsubstituted aryl, or substituted or unsubstituted araklyl).

In one embodiment, the D ring defines a substituted or unsubstituted pyrazolyl, triazolyl, or tetrazolyl ring. In these embodiments, therefore, the ligand compound corresponds to Formula (1A):

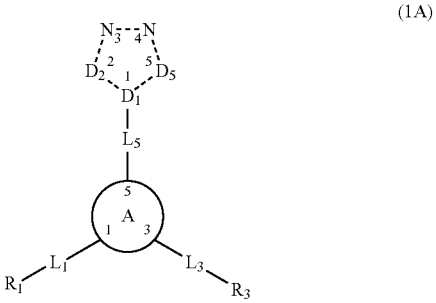

wherein the $D_1$, $D_2$, and $D_5$ moieties are (optionally substituted) carbon atoms or nitrogen atoms which, with the other two nitrogen atoms at the 3 and 4 positions, define a pyrazolyl, triazolyl, or tetrazolyl ring, provided that at least one of $D_1$, $D_2$, and $D_5$ is a carbon atom;

the dashed lines represent single or double bonds, or collectively form a conjugated bond system that is unsaturated to a degree of aromaticity; and the A ring, $L_1$, $L_3$, $L_5$, $R_1$, and $R_3$ are as defined in connection with Formula (1) above.

In certain preferred embodiments, for example, the D ring corresponds to one of the following five-membered rings:

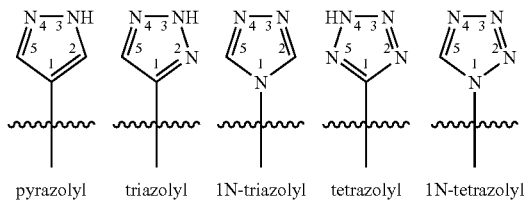

pyrazolyl   triazolyl   1N-triazolyl   tetrazolyl   1N-tetrazolyl wherein the wavy lines represent the attachment point of the D ring to the remainder of the ligand compound (i.e., at $L_5$).

In a particularly preferred embodiment, the D ring is forms a tetrazolyl ring. According to this embodiment, therefore, the ligand compound corresponds to Formula (1B):

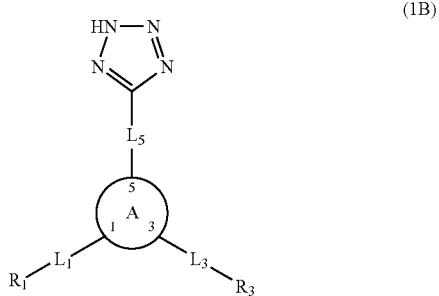

(1B)

wherein the A ring, $L_1$, $L_3$, $L_5$, $R_1$, and $R_3$ are as defined in connection with Formula (1) above.

The $L_1$, $L_3$, and $L_5$ Linking Moieties

In addition to the A and D rings, the ligand compounds of Formula (1) possess the $L_1$ and $L_3$ linking moieties, which join the $R_1$ and $R_3$ substituents to the A ring at the 1 and 3 positions, respectively, and the $L_5$ linking moiety, which joins the D ring to the A ring at the 5 position. In each of the ligand compounds described herein, including monomer and trimer ligands, and the supermolecular building blocks, molecular building blocks, and supramolecular assemblies containing such ligands, the $L_1$, $L_3$, and $L_5$ linking moieties may comprise covalent bonds, coordinate covalent bonds, noncovalent bonds, or a combination thereof. In certain embodiments, $L_1$, $L_3$, and/or $L_5$ comprise direct chemical bonds. In certain other embodiments, $L_1$, $L_3$, and $L_5$ comprise organic linking moieties. In still other embodiments, $L_1$, $L_3$, and $L_5$ comprise coordinating bonds.

In general, the dimension, pore size, free volume, and other properties of the molecular building blocks, supermolecular building blocks, and metal-organic frameworks including the ligands and/or trimers described herein can be correlated to the linker moieties, $L_1$, $L_3$, and $L_5$, of the ligand compound monomer. For example, expanded structures can result from expanding the series of linkers (e.g., as a series of phenylene moieties), and the pore size can be reduced by the selection of functional groups on the linkers that point towards the inner cavities of the building blocks. In addition, other functional properties of the resulting building blocks can be selected by the appropriate selection of substituents (e.g., fluorescent or catalytic moieties) on the linking subunits.

The $L_1$ and, $L_3$ linking moieties are generally the same and link the $R_1$ and $R_3$ substituents to the A ring at the 1 and 3 positions, respectively. The $L_5$ linking moiety may be the same as the $L_1$ and $L_3$ linking moieties, or may be a different linking moiety.

Typically, $L_1$ is a bond or $-(L_{11})_m-$, wherein $L_{11}$ is heterocyclene, hydrocarbylene, or substituted hydrocarbylene and m is a positive integer, $L_3$ is a bond or $-(L_{33})_m-$, wherein $L_{33}$ is hydrocarbylene or substituted hydrocarbylene and n is a positive integer, with $L_1$ and $L_3$ being the same, and $L_5$ is a bond or $-(L_{55})_m-$, wherein $L_{55}$ is heterocyclene, hydrocarbylene, or substituted hydrocarbylene and m is a positive integer. In one particular embodiment, $L_1$ and $L_3$ are each bonds. In another particular embodiment, $L_1$, $L_3$, and $L_5$ are each bonds.

Where $L_1$, $L_3$, and/or $L_5$ are $-(L_{11})_m-$, $-(L_{33})_m-$, and $-(L_{55})_m-$, respectively, although $L_{11}$, $L_{33}$, and $L_{55}$ may be heterocyclene, hydrocarbylene, or substituted hydrocarbylene, in certain embodiments $L_{11}$, $L_{33}$, and $L_{55}$ are substituted or unsubstituted alkylene, alkenylene, alkynylene, arylene, or heterocyclene. Where $L_{11}$, $L_{33}$, and $L_{55}$ are alkylene or alkenylene, for example, they may be straight, branched, or cyclic, preferably straight or cyclic. The $L_{11}$, $L_{33}$, and $L_{55}$ moieties may also be alkynyl, such as ethynyl. In one preferred embodiment, $L_1$ and $L_3$ are $-(L_{11})_m-$ and $-(L_{33})_m-$, respectively, wherein $L_{11}$ and $L_{33}$ are substituted or unsubstituted alkylene, alkynyl, substituted or unsubstituted arylene, or heterocyclene. In another preferred embodiment, $L_1$, $L_3$, and $L_5$ are $-(L_{11})_m-$, $-(L_{33})_m-$, and $-(L_{55})_m-$, respectively, wherein $L_{11}$, $L_{33}$, and $L_{55}$ are substituted or unsubstituted alkylene, alkynyl, substituted or unsubstituted arylene, or heterocyclene.

In a particularly preferred embodiment, $L_1$ and $L_3$ are each bonds or are $-(L_{11})_m-$ and $-(L_{33})_m-$, respectively, wherein $L_{11}$ and $L_{33}$ correspond to one of the following structures:

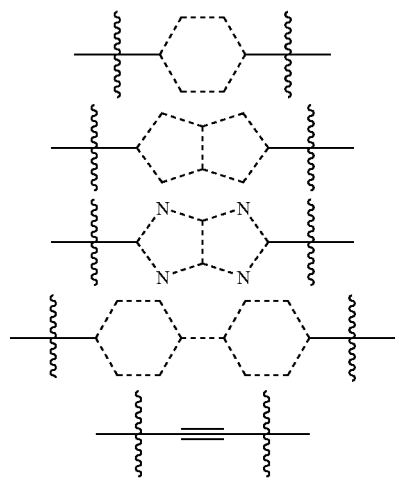

wherein the dashed lines represent single or double bonds, or collectively form a conjugated bond system that is unsaturated to a degree of aromaticity;

the wavy lines represent the attachment point of the $L_{11}$ or $L_{33}$ moiety to the A ring and another $L_{11}$ or $L_{33}$ moiety (i.e., when m is 2 or more) or to the A ring and $R_1$ or $R_3$; and each m is a positive integer.

According to this embodiment, $L_5$ is a bond or is -$(L_{55})_m$- wherein $L_{55}$ corresponds to one of the above structures and m is a positive integer.

In another preferred embodiment, $L_1$ and $L_3$ are each bonds or are -$(L_{11})_m$- and -$(L_{33})_m$-, respectively, wherein $L_{11}$ and $L_{33}$ are substituted or unsubstituted arylene; more preferably in this embodiment, $L_{11}$ and $L_{33}$ are substituted or unsubstituted phenylene. According to this embodiment, $L_5$ is a bond or is -$(L_{55})_m$- wherein $L_{55}$ is substituted or unsubstituted arylene; more preferably $L_{55}$ is substituted or unsubstituted phenylene.

Where $L_{11}$, $L_{33}$, and/or $L_{55}$ are substituted hydrocarbylene (e.g., substituted alkylene or substituted arylene, more preferably substituted phenylene), the substituents may be any of a variety of substituents to impart a desired effect or property to the ligand compound, the triangular molecular building block, the supermolecular polyhedral building block, or the resulting supramolecular building block or metal-organic framework comprising such ligands, trimers, and building blocks. As noted above, the substituent(s) for the linker moieties may be selected to impart various desired properties, such as magnetic activity, luminescent activity, phosphorescent activity, fluorescent activity, and catalytic and redox activity to the building blocks and assembled structures comprising these components. Exemplary substituents which may be found on the substituted alkylene or substituted arylene (e.g., substituted phenylene) moieties of $L_{11}$, $L_{33}$, and $L_{55}$ include, but are not limited to, one or more of the following chemical moieties: —OH, —OR, —COOH, —COOR, —CONH$_2$, —NH$_2$, —NHR, —NRR, —SH, —SR, —SO$_2$R, —SO$_2$H, —SOR, and halo (including F, Cl, Br, and I), wherein each occurrence of R may be hydrocarbyl or substituted hydrocarbyl (e.g., substituted or unsubstituted alkyl, substituted or unsubstituted aryl, or substituted or unsubstituted araklyl).

Although $L_{11}$ and $L_{33}$ are generally the same, when these moieties are substituted hydrocarbylene they may not necessarily carry the same substituents on each hydrocarbylene moiety. For instance, $L_{11}$ may be substituted phenylene carrying a particular halo substituent (e.g., F, Cl, Br, and/or I), or a combination thereof, while $L_{33}$ may be substituted phenylene carrying a different halo substituent (or a different combination of halo substituents), or different substituents altogether (e.g., —OH or NH$_2$). Thus, in various embodiments $L_{11}$ and $L_{33}$ are independently:

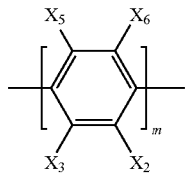

wherein m is a positive integer and each $X_2$, $X_3$, $X_5$, and $X_6$ is independently —H, —OH, —OR, —COOH, —COOR, —CONH$_2$, —NH$_2$, —NHR, —NRR, —SH, —SR, —SO$_2$R, —SO$_2$H, —SOR, or halo. In these and other embodiments, $L_{55}$ may be:

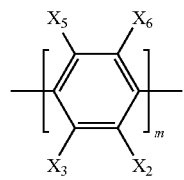

wherein m is a positive integer and each $X_2$, $X_3$, $X_5$, and $X_6$ is independently —H, —OH, —OR, —COOH, —COOR, —CONH$_2$, —NH$_2$, —NHR, —NRR, —SH, —SR, —SO$_2$R, —SO$_2$H, —SOR, or halo. The substituents on a substituted hydrocarbylene $L_{55}$ moiety may be the same or different from those of a substituted or unsubstituted hydrocarbylene $L_{11}$ and/or $L_{33}$ moiety.

Where $L_1$, $L_3$, and $L_5$ are -$(L_{11})_m$-, -$(L_{33})_m$-, -$(L_{55})_m$-, respectively, the number of $L_{11}$, $L_{33}$, and $L_{55}$ repeat units, m, is a positive integer. As noted above, $L_1$ and $L_3$ are generally the same, so the number of repeat units, m, for these moieties will be the same. The number of repeat units for $L_{55}$, however, may be the same or different than the number of repeat units for the $L_{11}$ and $L_{33}$ moieties. Generally speaking, compounds carrying more than ten (10) $L_{11}$, $L_{33}$, and/or $L_{55}$ repeat units tend to be less desired, as the substituent arms can lose rigidity and lack the proper orientation for assembly into larger molecular and supermolecular building blocks and metal-organic frameworks. Typically, where present, each m is 1 to 10 (e.g., 1, 2, 3, 4, 5, 6, 7, 8, 9, or 10). In one embodiment, $L_1$ and $L_3$ are -$(L_{11})_m$- and -$(L_{33})_m$-, respectively, wherein $L_{11}$ and $L_{33}$ are substituted or unsubstituted phenylene and each m is 1, 2, 3, 4, or 5; more preferably, each m is 1, 2, or 3; in this embodiment, $L_5$ is a bond or -$(L_{55})_m$-, wherein $L_{55}$ is substituted or unsubstituted phenylene and m is 1, 2, 3, 4, or 5; more preferably, m is 1, 2, or 3.

While the $L_1$ and $L_3$ substituents are generally the same, the $L_5$ substituent may also be the same as $L_1$ and $L_3$, or may be different from $L_1$ and $L_3$. For instance, $L_1$ and $L_3$ can each be a bond and $L_5$ can be -$(L_{55})_m$-, wherein $L_{55}$ is substituted or unsubstituted alkylene or substituted or unsubstituted arylene (e.g., phenylene) and m is a positive integer (e.g., 1, 2, or 3). Alternatively, $L_1$ and $L_3$ can each be -$(L_{11})_m$- and -$(L_{33})_m$-, respectively, wherein $L_{11}$ and $L_{33}$ are each substituted or unsubstituted alkylene or substituted or unsubstituted arylene (e.g., phenylene) and each m is a positive integer (e.g., 1, 2, or 3), and $L_5$ is a bond. Still further, $L_1$ and $L_3$ can each be -$(L_{11})_m$- and -$(L_{33})_m$-, respectively, wherein $L_{11}$ and $L_{33}$ are each substituted or unsubstituted alkylene or substituted or unsubstituted arylene (e.g., phenylene) and each m is 1, 2, or 3, while $L_5$ is -$(L_{55})_m$-, wherein $L_{55}$ is substituted or unsubstituted alkylene or substituted or unsubstituted arylene (e.g., phenylene) and m is a positive integer (e.g., 1, 2, or 3), with the m of the -$(L_{11})_m$- and -$(L_{33})_m$- moieties being the same or different from the m of the -$(L_{55})_m$- moiety. For instance, $L_{11}$ and $L_{33}$ can each be -$(L_{11})_{m11}$- and -$(L_{33})_{m33}$-, wherein $L_{11}$ and $L_{33}$ are each substituted or unsubstituted alkylene or substituted or unsubstituted arylene (e.g., phenylene) and $m_{11}$ and $m_{33}$ are each 1, while $L_5$ is -$(L_{55})_{m55}$-, wherein $L_{55}$ is substituted or unsubstituted alkylene or substituted or unsubstituted arylene (e.g., phenylene) and $m_{55}$ is 2 or 3, or vice versa.

In certain other embodiments, the heterocyclene, hydrocarbylene, or substituted hydrocarbylene repeat units of $L_{11}$, $L_{33}$, and/or $L_{55}$ may also be further linked to the 1, 3, and/or 5 positions of the A ring and/or to the $R_1$, $R_3$, and/or the D rings by one or more additional linking moieties. In these embodiments, therefore, $L_1$ and $L_3$ are each a bond or -$(L_{11}$-$L_{111})_m$- and -$(L_{33}$-$L_{333})_m$-, respectively, wherein $L_{11}$ and $L_{33}$ are defined above and $L_{111}$ and $L_{333}$ are each an additional linking moiety. Similarly, in these embodiments, $L_5$ is a bond or -$(L_{55}$-$L_{555})_m$-, wherein $L_{55}$ is defined above and $L_{555}$ is an additional linking moiety. Exemplary additional linking moieties for $L_{111}$, $L_{333}$, and/or $L_{555}$ include, for example, amines, amides, esters, ethers, carbamates, sulphonamides, and/or ureas. Thus, for example, the additional linking moiety, $L_{111}$, $L_{333}$, and/or $L_{555}$, may have the formula: —NH—, —C(=O)—NH—, —C(=O)—O—, —$R_y$—O—, —O—C(=O)—NH—, —$SO_2$—NH—, or —NH—C(=O)—NH—, wherein $R_y$ is alkylene (e.g., —$CH_2$—).

In still other embodiments, $L_1$, $L_3$, and $L_5$ are directly linked to the 1, 3, and/or 5 positions of the A ring and/or to the $R_1$, $R_3$, and/or the D rings by the additional linking moieties disclosed above. According to these embodiments, therefore, $L_1$ and $L_3$ are each a bond or -$(L_{111})_m$- and -$(L_{333})_m$-, respectively, wherein $L_{111}$ and $L_{333}$ are amine, amide, ester, ether, carbamate, sulphonamide, and/or urea linking moieties. In these embodiments, for example, $L_{111}$ and $L_{333}$ have the formula: —NH—, —C(=O)—NH—, —C(=O)—O—, —$R_y$—O—, —O—C(=O)—NH—, —$SO_2$—NH—, or —NH—C(=O)—NH—, wherein $R_y$ is alkylene (e.g., —$CH_2$—), and m is a positive integer (e.g., 1, 2, or 3). Similarly, in these embodiments, $L_5$ is a bond or -$(L_{555})_m$-, wherein $L_{555}$ has the formula: —NH—, —C(=O)—NH—, —C(=O)—O—, —$R_y$—O—, —O—C(=O)—NH—, —$SO_2$—NH—, or —NH—C(=O)—NH—, wherein $R_y$ is alkylene (e.g., —$CH_2$—), and m is a positive integer (e.g., 1, 2, or 3).

$R_1$ and $R_3$

In addition to the A and D rings, $L_1$, $L_3$, and $L_5$, the ligand compound corresponding to Formula (1) carries the $R_1$ and $R_3$ substituents. Generally, the $R_1$ and $R_3$ substituents are functional groups capable of coordinately bonding to at least one metal (including metal ions and metal oxides). The functional groups for $R_1$ and $R_3$ are preferably at least bidentate, and may be tridentate, or otherwise polydentate. In one embodiment, $R_1$ and $R_3$ are bidentate functional groups.

In particular, the $R_1$ and $R_3$ groups are capable of coordinately bonding to at least one metal (including metal ions and metal oxides) and typically at least two metals (which may be either the same or different) to form the supermolecular building block. Thus, for example, while the $R_1$ and $R_3$ groups may initially be a functional group, when combined with metal(s) in the formation of the supermolecular building block the $R_1$ and $R_3$ groups become coordinating groups with the metal ions or oxides.

Representative functional groups capable of coordinately binding to at least one metal include, but are not limited to, the following: —$CO_2H$, —$CS_2H$, —$NO_2$, —$SO_3H$, —$Si(OH)_3$, —$Ge(OH)_3$, —$Sn(OH)_3$, —$Si(SH)_4$, —$Ge(SH)_4$, —$Sn(SH)_3$, —$PO_3H$, —$AsO_3H$, —$AsO_4H$, —$P(SH)_3$, —$As(SH)_3$, —$CH(SH)_2$, —$C(SH)_3$, —$CH(NH_2)_2$, —$C(NH_2)_2$, —$CH(OH)_2$, —$C(OH)_3$, —$CH(CN)_2$ and —$C(CN)_3$, —$CH(RSH)_2$, —$C(RSH)_3$, —$CH(RNH_2)_2$, —$C(RNH_2)_3$, —$CH(ROH)_2$, —$C(ROH)_3$, —$CH(RCN)_2$, and —$C(RCN)_3$, wherein each R is independently an alkyl or alkenyl group having from 1 to 5 carbon atoms, or an aryl group consisting of 1 to 2 phenyl rings. Other functional groups capable of coordinately binding to at least one metal include, but are not limited to, nitrogen donors such as, for example, cyano (—CN), amino, pyrazole, imidazole, pyridine, and functional groups containing such moieties. See, e.g., Tominaga et al., Angew. Chem. Int. Ed. 2004, 43, 5621-5625.

In one preferred embodiment, $R_1$ and $R_3$ are carboxylic acid (—$CO_2H$) groups. According to this embodiment, when the monomer (or trimer) is combined with one or more metals during the formation of a supermolecular building block, the carboxylic acid moieties become carboxylate moieties which coordinately bond with two metals in the following (bidentate) manner:

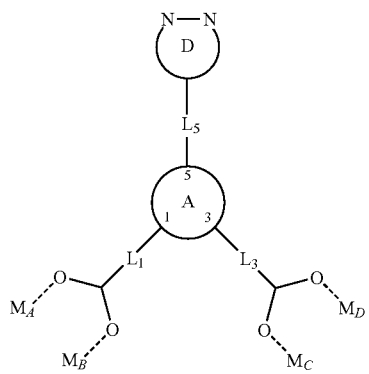

wherein $M_A$, $M_B$, $M_C$, and $M_D$ are metal ions (including metal oxides) and the dashed lines represent coordination bonds, with other coordination being possible with the metals and other moieties not specifically illustrated (e.g., between $M_A$ and $M_B$, between $M_C$ and $M_D$, and/or between $M_A$, $M_B$, $M_C$, and/or $M_D$ an other moieties (for example, additional ligand compounds)), and the A ring, the D ring, $L_1$, $L_3$, and $L_5$ are as defined in connection with Formula (1) above.

In combination, among certain of the preferred embodiments are ligand compounds corresponding to Formula (1) wherein:
the A ring is benzene;
the D ring is a pyrazolyl, triazolyl, or tetrazolyl ring;
$L_1$ and $L_3$ are each a bond or are -$(L_{11})_m$- and -$(L_{33})_m$-, respectively, wherein $L_{11}$ and $L_{33}$ are substituted or unsubstituted arylene;
$L_5$ is a bond or is -$(L_{55})_m$-, wherein $L_{55}$ is substituted or unsubstituted arylene; and
$R_1$ and $R_3$ are carboxylic acid (—$CO_2H$) moieties.

In certain other preferred embodiments, the ligand compounds correspond to Formula (1) wherein:
the A ring is benzene;
the D ring is a pyrazolyl, triazolyl, or tetrazolyl ring;
$L_1$ and $L_3$ are each a bond or are -$(L_{11}$-$L_{111})_m$- and -$(L_{33}$-$L_{333})_m$-, respectively, wherein $L_{11}$ and $L_{33}$ are substituted or unsubstituted arylene and $L_{111}$ and $L_{333}$ are —NH—, —C(=O)—NH—, —C(=O)—O—, —$R_y$—O—, —O—C(=O)—NH—, —$SO_2$—NH—, or —NH—C(=O)—NH—, wherein $R_y$ is alkylene;
$L_5$ is a bond or is -$(L_{55}$-$L_{555})_m$-, wherein $L_{55}$ is substituted or unsubstituted arylene and $L_{555}$ is —NH—, —C(=O)—NH—, —C(=O)—O—, —$R_y$—O—, —O—C(=O)—NH—, —$SO_2$—NH—, or —NH—C(=O)—NH—, wherein $R_y$ is alkylene; and
$R_1$ and $R_3$ are carboxylic acid (—$CO_2H$) moieties.

Certain particularly preferred ligand compounds corresponding to Formula (1) have the following structures:

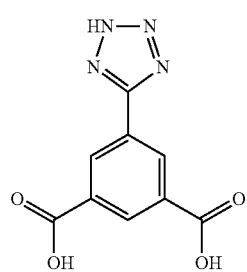

(1C)

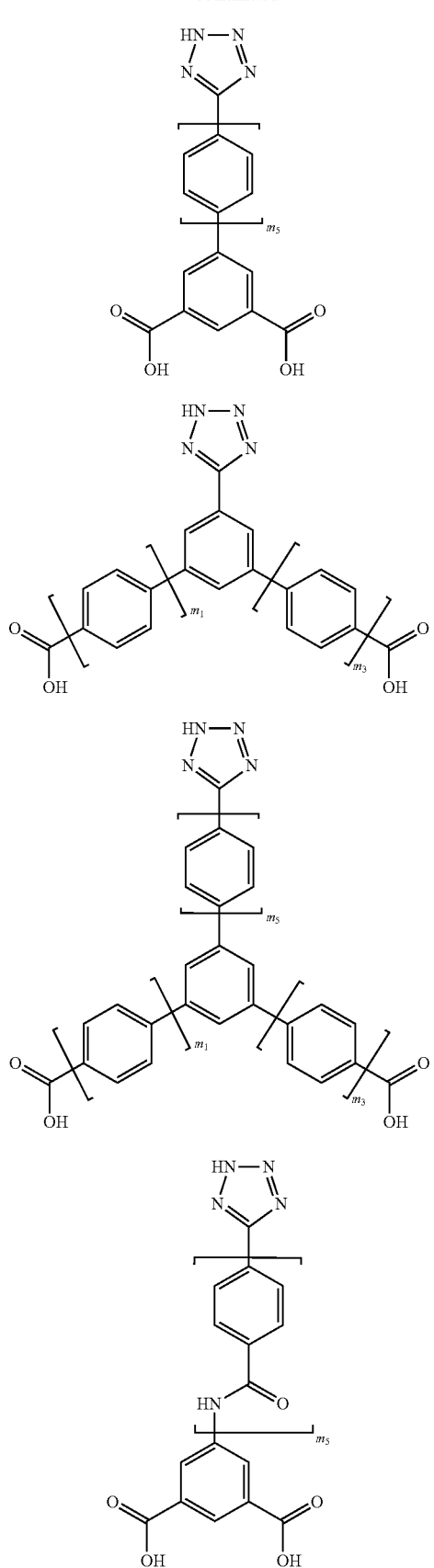

(1D)

(1E)

(1F)

(1G)

wherein $m_1$ and $m_3$, if present, are 1, 2, or 3, and $m_5$, if present, is 1, 2, or 3. In the interest of space, the bracketed repeating phenylene moieties are shown as unsubstituted phenylene. It will be appreciated, however, that these phenylene moieties may be substituted with one or more substituent groups, as discussed in detail above.

Trimer Ligands

Another aspect of the present invention is directed to trimer ligands. The trimer ligands may be used, for example, in the preparation of both the supermolecular building blocks and the triangular molecular building blocks. For example, one portion of the trimer can be used to form a portion of the triangular molecular building block, while another portion(s) of the trimer can be used to form three different supermolecular building blocks. The trimers generally comprise three arms, or points of attachment, centered around a connection network or bridging moiety, with the three arms/points of attachment positioned 120° from each other in a plane:

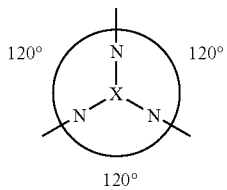

wherein each N represents one of the three arms and X represents the connection network or bridging moiety. In general, the connection network or bridging moiety comprises a metal-organic moiety or comprises an organic moiety. Individual trimers can be used in the formation of three different supermolecular building blocks distributed around the trimer core, which forms the triangular molecular building block. Several trimers, in combination, can thus be used to form multiple supermolecular building block/triangular molecular building block combinations. Stated differently, supermolecular polyhedral building blocks and triangular building blocks each comprising portions of a trimer ligand can further combine with other building blocks to form polyhedron molecules and polymeric structures as described elsewhere herein. The polyhedra may exist as discrete macromolecules or may be fused to engineer open framework solids.

As described above, the ligands may be used to form only the supermolecular building block. Alternatively, the ligands can be used to form both the supermolecular building block and the triangular molecular building block. In one embodiment, the ligand is a trimer having the structure of Formula (2):

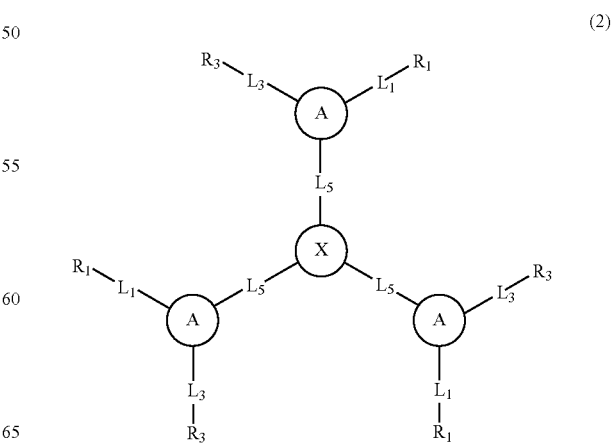

(2)

wherein the X ring comprises a monocyclic or polycyclic fused ring system, or has the formula:

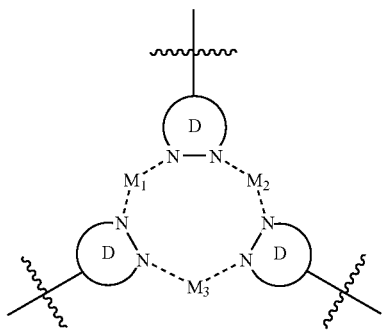

$M_1$, $M_2$, and $M_3$ are independently metal ions;

the dashed lines represent coordination bonds between the nitrogen atoms of the D rings and the metals; and the A ring, the D rings, each $L_1$, $L_3$, and $L_5$, and each $R_1$ and $R_3$ are as defined in connection with Formula (1) above.

In this embodiment, the triangular molecular building block comprises the X ring of the trimer with $L_1$, $L_3$, and $L_5$ being linkers, linking the triangular molecular building block to three supermolecular building blocks. And, each A ring in each of the three arms of the trimer forms a portion of one of the three supermolecular building blocks.

The X Ring

As noted above, the trimer ligand corresponding to Formula (2) includes the X ring. In general, the X ring functions as the triangular molecular building block, a connection network or bridge for the three arms or nodes of the trimer structure, with the remainder of the trimer structure forming three different supermolecular building blocks.

In certain embodiments, the X ring comprises a monocyclic or polycyclic fused ring system; more preferably, the X ring is a six-membered carbocyclic or heterocyclic ring. According to these embodiments, therefore, the connection or bridging network, X, is an organic (i.e., non-metal) moiety. The resulting triangular molecular building block is thus pre-assembled as a component of the trimer ligand. Similar to the A ring discussed above, the X ring may be any six-membered carbocyclic or heterocyclic ring that is capable of being substituted such that each of three arms, or points of attachment, are about 120 degrees from each other. Where the X ring is a six-membered carbocyclic ring it is also generally preferred that the ring be an aromatic ring in order to maintain the trimer in a substantially planar and rigid configuration while supporting three arms spaced ~120° from each other. Cationic forms of the carbocyclic or heterocyclic X ring are also contemplated; that is, a free electron pair of a carbon or heteroatom may be involved in the skeletal bonding of the ring system, e.g., in the formation of the ring or in the double bond system of the ring.

In one preferred embodiment, the X ring is a six-membered carbocyclic or heterocyclic ring having the structure:

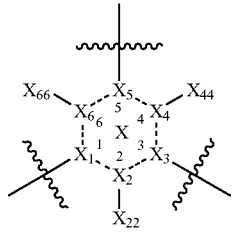

wherein the atoms defining the ring, $X_1$, $X_2$, $X_3$, $X_4$, $X_5$, and $X_6$, are independently selected from carbon, nitrogen, oxygen, boron, and sulfur atoms (including cations thereof);

each of the $X_1$, $X_3$, and $X_5$ ring atoms are substituted with the three -$L_5$-A ring moieties, which are positioned about 120° from each other (as described in connection with Formula (2));

$X_{22}$, $X_{44}$, and $X_{66}$ are any atom or group of atoms that do not otherwise affect the ~120° bond angles of the $X_1$, $X_3$, and $X_5$ nodes;

the dashed lines represent single or double bonds, or collectively form a conjugated bond system that is unsaturated to a degree of aromaticity;

and the wavy lines represent the attachment point of the X ring to the remainder of the compound (i.e., at each of the three -$L_5$-A ring arms).

In general, the $X_{22}$, $X_{44}$, and $X_{66}$ substituents are selected such that they will not adversely affect other substituents on the triangular molecular building block (or the ligand subunits) and/or will not affect assembly of the desired compounds and further assembly of the supermolecular building blocks and/or portions of the triangular molecular or supermolecular building blocks; in particular, the $X_{22}$, $X_{44}$, and $X_{66}$ substituents are preferably selected such that they do not affect the ~120° bond angles of the three arms, or points of attachment, of the triangular molecular building block as described above. Suitable substituents for $X_{22}$, $X_{44}$, and $X_{66}$ include, for example, one or more of the following chemical moieties: —H, —OH, —OR, —COOH, —COOR, —CONH$_2$, —NH$_2$, —NHR, —NRR, —SH, —SR, —SO$_2$R, —SO$_2$H, —SOR, and halo (including F, Cl, Br, and I), wherein each occurrence of R may be hydrocarbyl or substituted hydrocarbyl (e.g., substituted or unsubstituted alkyl, substituted or unsubstituted aryl, or substituted or unsubstituted araklyl).

The X ring may be, for example, a six-membered aromatic ring. Alternatively, the X ring may be a six-membered non-aromatic ring. In one embodiment, for example, the six-membered X ring is selected from benzene, pyridine, pryridinium, pyrimidine, pyrimidinium, triazine, triazinium, pyrylium, boroxine, diborabenzene, and triborabenzene rings. Thus, for example, the X ring may correspond to one of the following exemplary six-membered rings:

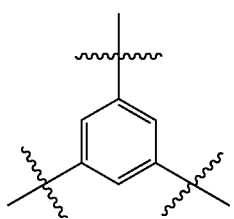

(X$_1$)

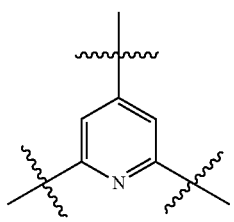

(X$_2$)

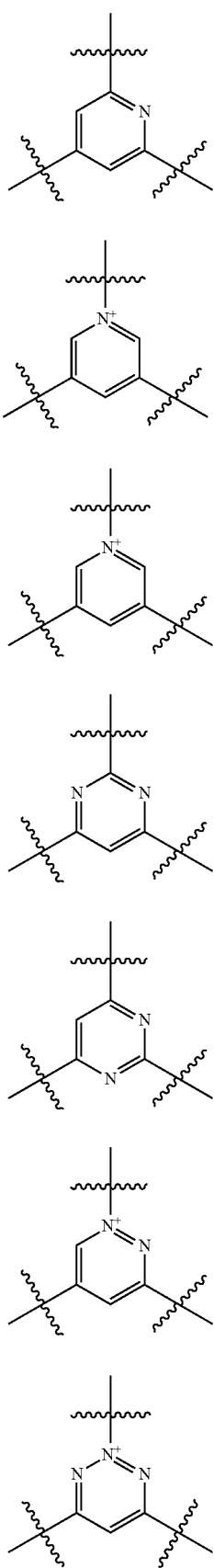
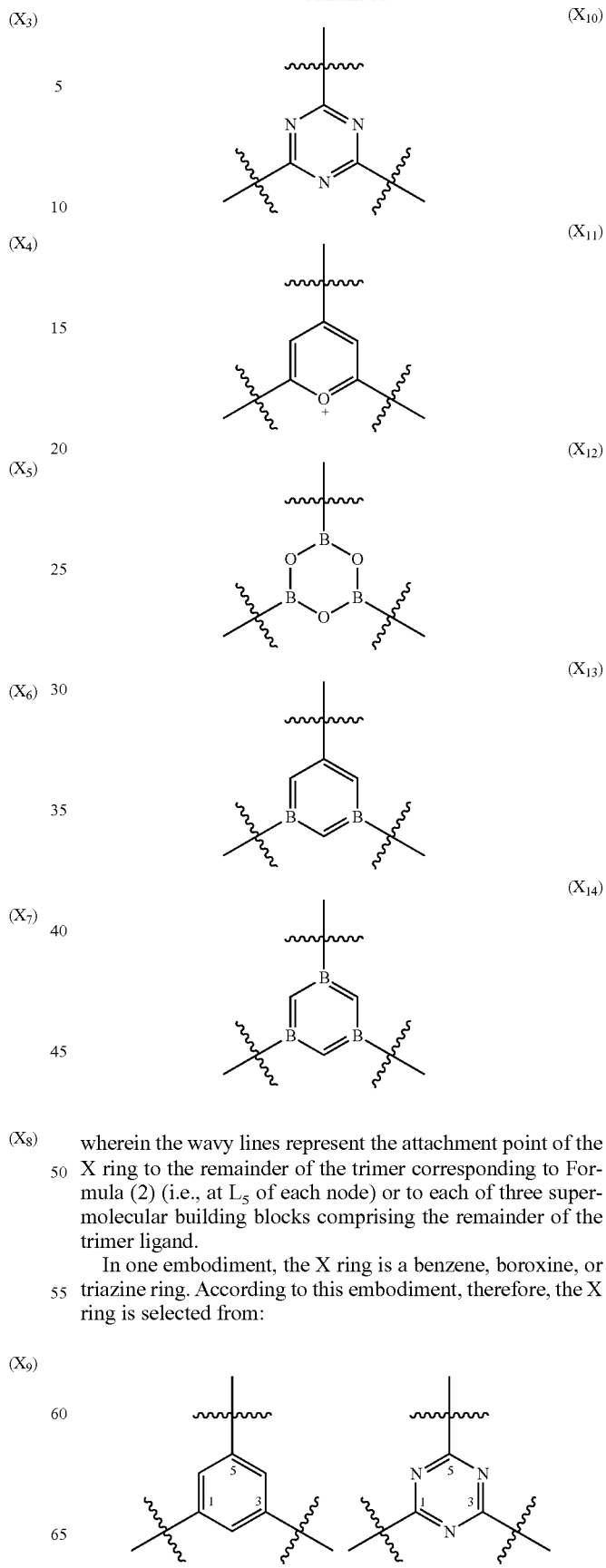

wherein the wavy lines represent the attachment point of the X ring to the remainder of the trimer corresponding to Formula (2) (i.e., at $L_5$ of each node) or to each of three supermolecular building blocks comprising the remainder of the trimer ligand.

In one embodiment, the X ring is a benzene, boroxine, or triazine ring. According to this embodiment, therefore, the X ring is selected from:

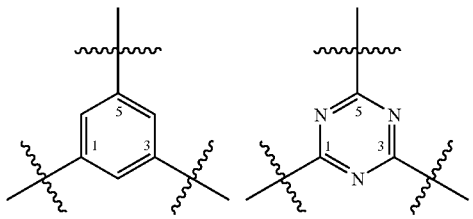

-continued

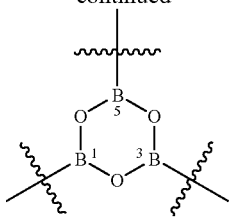

wherein the wavy lines represent the attachment point of the X ring to the remainder of the trimer corresponding to Formula (2) (i.e., at $L_5$ of each node) or the attachment point of the X ring (i.e., triangular molecular building block) to three supermolecular building blocks. In one preferred embodiment, the X ring is a benzene ring. According to this embodiment, therefore, the X ring has the formula:

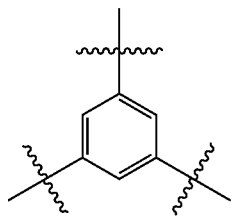

wherein the wavy lines represent the attachment point of the benzene ring to the remainder of the molecule corresponding to Formula (2) (i.e., at $L_5$ of each node). In this embodiment, therefore, the ligand corresponds to Formula (22):

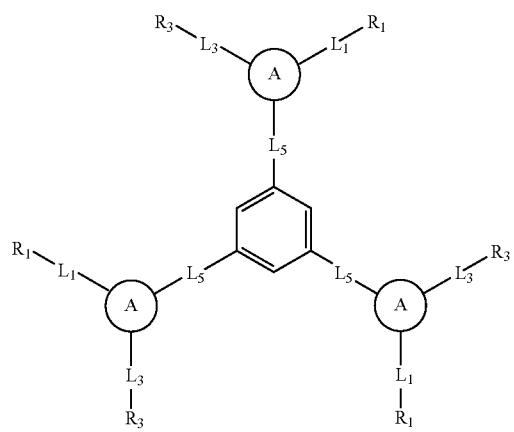

(22)

wherein each A ring and each $L_1$, $L_3$, $L_5$, $R_1$, and $R_3$ are as defined in connection with Formula (1) above.

In certain other embodiments, the triangular molecular building block is a metal-organic moiety. In these embodiments, for example, the X ring portion of the trimer ligand, and thereby the triangular molecular building block comprises the formula:

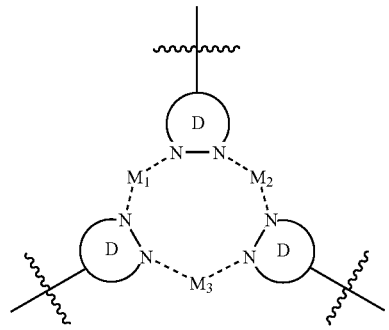

wherein
$M_1$, $M_2$, and $M_3$ are independently metal ions;
the dashed lines represent coordination bonds between a nitrogen atom of a D ring and a metal;
the wavy lines represent the attachment point of the X ring to the remainder of the ligand corresponding to Formula (2) (i.e., at $L_5$ of each node); and
each D ring is as defined in connection with Formula (1) above.

According to these embodiments, the trimer corresponding to Formula (2) comprises three of the ligand compounds corresponding to Formula (1), the two nitrogen atoms of the D ring coordinating with two metal atoms in a bis-monodentate fashion, for a total of three metal ions, M, to form the triangular molecular building block (i.e., the X ring structure). The remainder of the trimer ligand (i.e., each of the A ring nodes) is a part of a supermolecular building block. In certain of these embodiments, the trimer ligand corresponds to Formula (222):

(222)

wherein each A ring, the D rings, and each $L_1$, $L_3$, $L_5$, $R_1$, $R_3$, and $M_1$, $M_2$, and $M_3$ are as defined in connection with Formulae (1) and (2).

In a preferred embodiment, each D ring defines a tetrazolyl ring; thus, the triangular molecular building block has the formula:

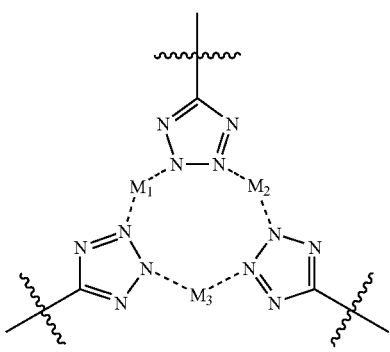

wherein and $M_1$, $M_2$, and $M_3$ are as defined in connection with Formulae (1) and (2). The triangular molecular building block described above may be pre-assembled as a component of the trimer ligand, or may be formed in situ.

The A Ring

As described in connection with Formula (1), the A ring may be a monocyclic or polycyclic fused ring system capable of being substituted such that each at least three substituents of the monocyclic or polycyclic ring system are positioned about 120 degrees from each other.

Where the A ring is a monocyclic or polycyclic fused ring system, the A ring may be, for example, a six-membered aromatic ring. Alternatively, the A ring may be a six-membered non-aromatic ring. In one embodiment, for example, the six-membered A ring is selected from benzene, pyridine, pryridinium, pyrimidine, pyrimidinium, triazine, triazinium, pyrylium, boroxine, diborabenzene, and triborabenzene rings. In one embodiment, the A ring is a benzene, boroxine, or triazine ring. According to this embodiment, therefore, each A ring is selected from:

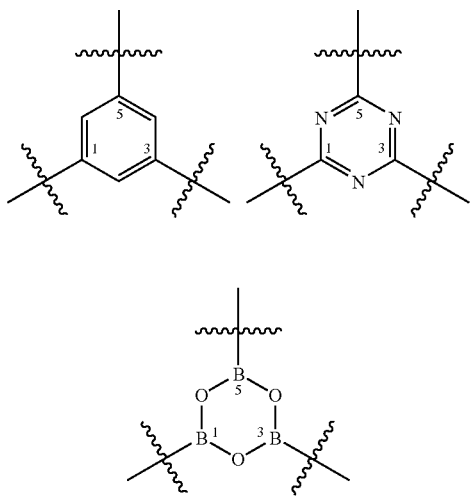

wherein the wavy lines represent the attachment point of the A ring to the remainder of the trimer corresponding to Formula (2) (i.e., at $L_1$, $L_3$, or $L_5$ of each substituent arm). In one preferred embodiment, the A ring is a benzene ring. According to this embodiment, therefore, the A ring has the formula:

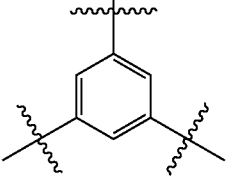

wherein the wavy lines represent the attachment point of the benzene ring to the remainder of the trimer corresponding to Formula (2) (i.e., at $L_1$, $L_3$, or $L_5$ of each substituent arm) or to the supermolecular building blocks.

The $L_1$, $L_3$, and $L_5$ Moieties

In addition to the A and X rings, the compounds of Formula (2) possess the $L_1$, $L_3$ and $L_5$ linking moieties, which join the $R_1$ and $R_3$ substituents to each A ring at the 1 and 3 positions, respectively, and the $L_5$ linking moiety, which joins the X ring to the A ring at the 5 position.

The $L_1$, $L_3$, and $L_5$ linking moieties are generally defined in connection with the ligand monomer of Formula (1). Thus, for example, $L_1$ is a bond or $-(L_{11})_m-$, wherein $L_{11}$ is hydrocarbylene or substituted hydrocarbylene and m is a positive integer, $L_3$ is a bond or $-(L_{33})_m-$, wherein $L_{33}$ is hydrocarbylene or substituted hydrocarbylene and n is a positive integer, with $L_1$ and $L_3$ being the same, and $L_5$ is a bond or $-(L_{55})_m-$, wherein $L_{55}$ is hydrocarbylene or substituted hydrocarbylene and m is a positive integer. In one particular embodiment, $L_1$ and $L_3$ are each bonds. In another particular embodiment, $L_1$, $L_3$, and $L_5$ are each bonds.

In one embodiment, each $L_1$ and $L_3$ are bonds or are $-(L_{11})_m-$ and $-(L_{33})_m-$, respectively, wherein $L_{11}$ and $L_{33}$ are substituted or unsubstituted phenylene. According to this embodiment, $L_5$ is a bond or is $-(L_{55})_m-$ wherein $L_{55}$ is substituted or unsubstituted phenylene. Exemplary substituents which may be found on the substituted hydrocarbyl (e.g., phenylene) moieties of $L_{11}$, $L_{33}$, and/or $L_{55}$ are discussed in detail above, and include, but are not limited to: —OH, —OR, —COOH, —COOR, —CONH$_2$, —NH$_2$, —NHR, —NRR, —SH, —SR, —SO$_2$R, —SO$_2$H, —SOR, and halo (including F, Cl, Br, and I), wherein each occurrence of R may be hydrocarbyl or substituted hydrocarbyl (e.g., substituted or unsubstituted alkyl, substituted or unsubstituted aryl, or substituted or unsubstituted araklyl).

In another embodiment, each $L_1$ and $L_3$ is a bond or $-(L_{11}-L_{111})_m-$ and $-(L_{33}-L_{333})_m-$, respectively, wherein $L_{11}$ and $L_{33}$ are defined above and $L_{111}$ and $L_{333}$ are each an additional linking moiety. Similarly, in these embodiments, each $L_5$ is a bond or $-(L_{55}-L_{555})_m-$, wherein $L_{55}$ is defined above and $L_{555}$ is an additional linking moiety. Exemplary additional linking moieties for $L_{111}$, $L_{333}$, and/or $L_{555}$ include, for example, amines, amides, esters, ethers, carbamates, sulphonamides, and/or ureas. For example, the additional linking moiety, $L_{11}$, $L_{333}$, and/or $L_{555}$, may be have the formula: —NH—, —C(=O)—NH—, —C(=O)—O—, —R$_y$—O—, —O—C(=O)—NH—, —SO$_2$—NH—, or —NH—C(=O)—NH—, wherein R$_y$ is alkylene (e.g., —CH$_2$—).

In another embodiment, $L_1$ and $L_3$ are each a bond or $-(L_{111})_m-$ and $-(L_{333})_m-$, respectively, wherein $L_{111}$ and $L_{333}$ have the formula: —NH—, —C(=O)—NH—, —C(=O)—O—, —R$_y$—O—, —O—C(=O)—NH—, —SO$_2$—NH—, or —NH—C(=O)—NH—, wherein R$_y$ is alkylene (e.g., —CH$_2$—), and m is a positive integer (e.g., 1, 2, or 3). Similarly, in these embodiments, $L_5$ is a bond or $-(L_{555})_m-$, wherein $L_{555}$ has the formula: —NH—, —C(=O)—NH—, —C(=O)—O—, —R$_y$—O—, —O—C(=O)—NH—, —SO$_2$—NH—, or —NH—C(=O)—NH—, wherein R$_y$ is alkylene (e.g., —CH$_2$—), and m is a positive integer (e.g., 1, 2, or 3).

In one particular embodiment in which the X ring is a benzene ring, each $L_5$ is a bond. In another particular embodiment in which the X ring is a benzene ring, each $L_5$ is $-(L_{555})_m-$, wherein $L_{555}$ has the formula: $-NH-$, $-C(=O)-NH-$, $-C(=O)-O-$, $-R_y-O-$, $-O-C(=O)-NH-$, $-SO_2-NH-$, or $-NH-C(=O)-NH-$, wherein $R_y$ is alkylene (e.g., $-CH_2-$), and m is a positive integer (e.g., 1, 2, or 3). Thus, for example, the trimer ligand may correspond to one or more of Formulae (22A), (22B), and (22C):

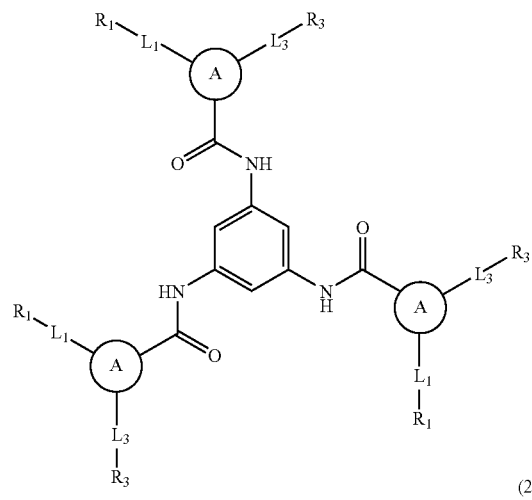

(22A)

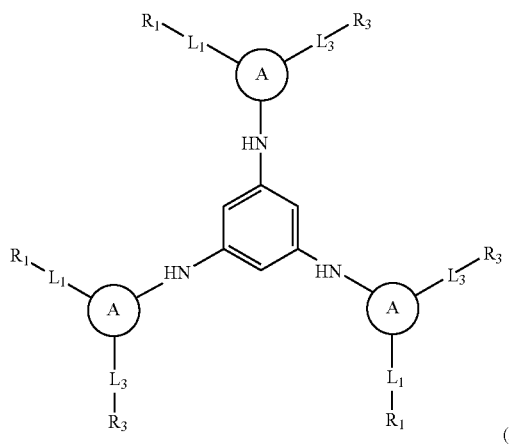

(22B)

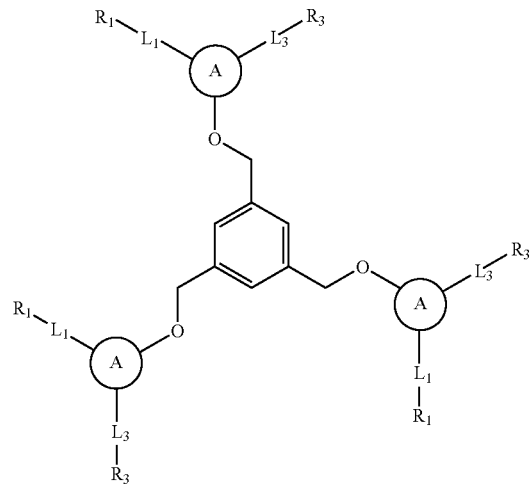

(22C)

wherein each A ring, and each $L_1$, $L_3$, $L_5$, $R_1$, and $R_3$ are as defined in connection with Formulae (1), (2), and (22).

$R_1$ and $R_3$

As noted above in connection with Formula (1), the $R_1$ and $R_3$ substituents are functional groups capable of coordinately binding to at least one metal (including metal ions and metal oxides). The functional groups for $R_1$ and $R_3$ are preferably at least bidentate, and may be tridentate, or otherwise multi- and/or polydentate. In one embodiment in which the triangular molecular building block compound corresponds to Formula (2), $R_1$ and $R_3$ are bidentate functional groups; more preferably in this embodiment, each $R_1$ and $R_3$ is a carboxylic acid ($-CO_2H$) moiety. As discussed above in connection with $R_1$ and $R_3$ of the monomer ligands corresponding to Formula (1), however, when the trimer is combined with one or more metals during the formation of a supermolecular building block, the carboxylic acid moieties become carboxylate moieties coordinately bond with two metals.

In combination, among certain of the preferred embodiments are organic (i.e., non-metal) trimer ligands corresponding to Formula (2) wherein:

each A ring is a benzene ring;
the X ring is a benzene ring;
each $L_1$ and $L_3$ is a bond or is $-(L_{11})_m-$ and $-(L_{33})_m-$, respectively, wherein $L_{11}$ and $L_{33}$ are substituted or unsubstituted arylene;
each $L_5$ is a bond or is $-(L_{55})_m-$, wherein $L_{55}$ is substituted or unsubstituted arylene; and
each $R_1$ and $R_3$ is a carboxylic acid moiety.

In certain other preferred embodiments, the trimer ligands correspond to Formula (2) wherein:

each A ring is a benzene ring;
the X ring is a benzene ring;
each $L_1$ and $L_3$ is a bond or is $-(L_{11}-L_{111})_m-$ and $-(L_{33}-L_{333})_m-$, respectively, wherein $L_{11}$ and $L_{33}$ are substituted or unsubstituted arylene and $L_{111}$ and $L_{333}$ are $-NH-$, $-C(=O)-NH-$, $-C(=O)-O-$, $-R_y-O-$, $-O-C(=O)-NH-$, $-SO_2-NH-$, or $-NH-C(=O)-NH-$, wherein $R_y$ is alkylene;
each $L_5$ is a bond or is $-(L_{55}-L_{555})_m-$, wherein $L_{55}$ is substituted or unsubstituted arylene and $L_{555}$ is $-NH-$, $-C(=O)-NH-$, $-C(=O)-O-$, $-O-C(=O)-NH-$, $-R_y-O-$, $-SO_2-NH-$, or $-NH-C(=O)-NH-$, where $R_y$ is alkylene; and
each $R_1$ and $R_3$ is a carboxylic acid moiety.

Certain particularly preferred organic (i.e., non-metal) trimers have the following structures:

(2A)

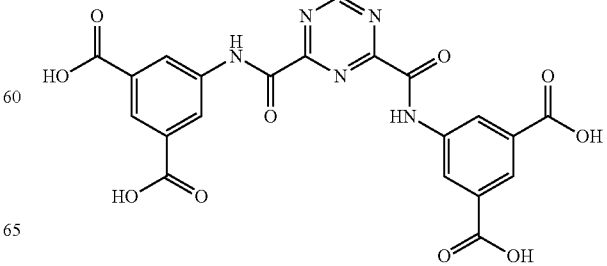

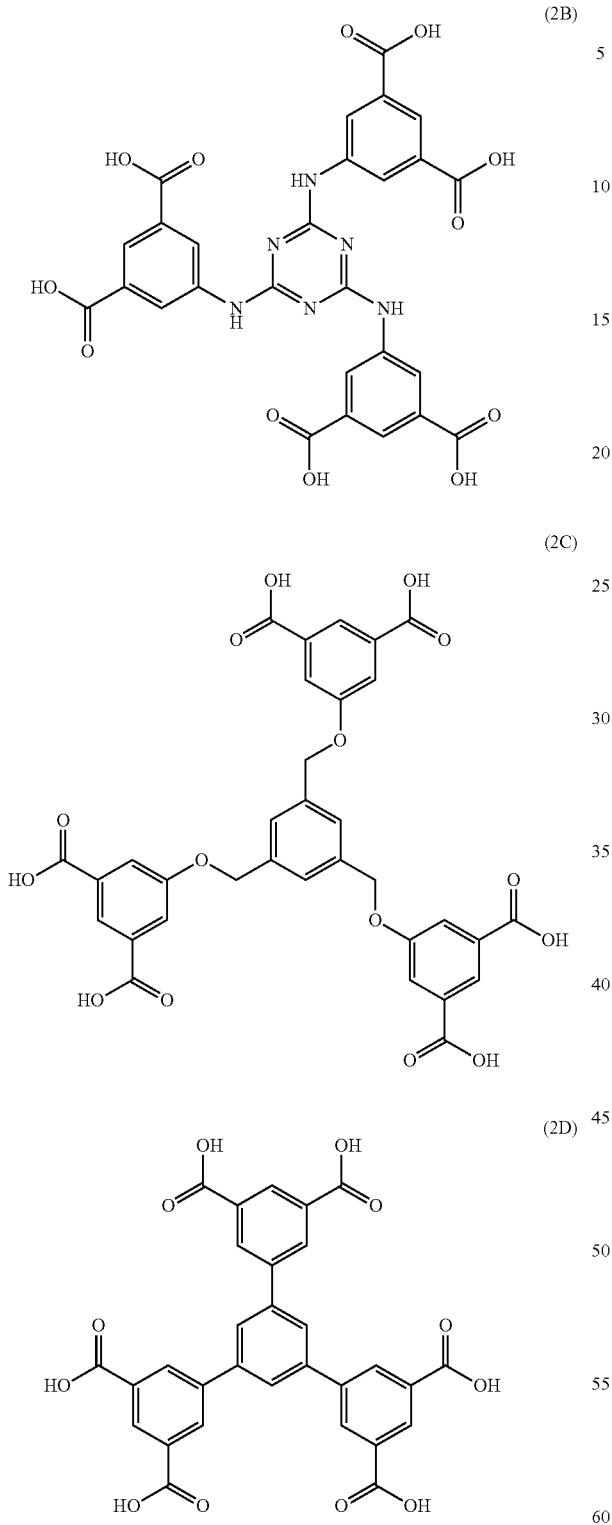

(2B)

(2C)

(2D)

Accordingly, the triangular molecular building block in these embodiments correspond to Formula $(22A_L)$, $(22B_L)$, or $(22C_L)$:

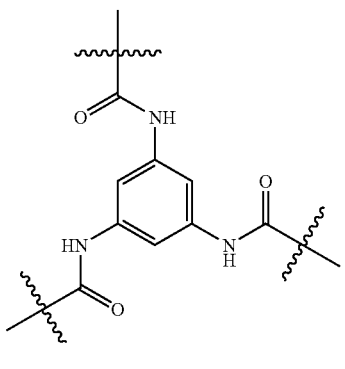

$(22A_L)$

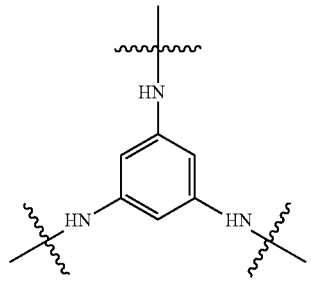

$(22B_L)$

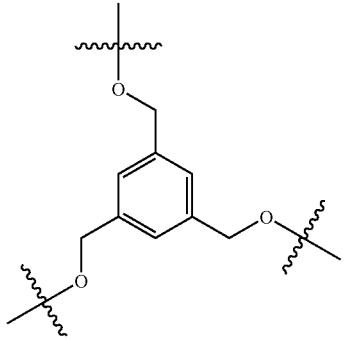

$(22C_L)$ wherein the wavy lines represent the attachment point of the benzene ring to the remainder of the trimer ligand corresponding to Formula (2) (i.e., at $L_1$, $L_3$, or $L_5$ of each substituent arm) or to the supermolecular building blocks.

In combination, among certain of the preferred embodiments are metal-organic trimers corresponding to Formula (2) wherein:

each A ring is a benzene ring;

the X ring is:

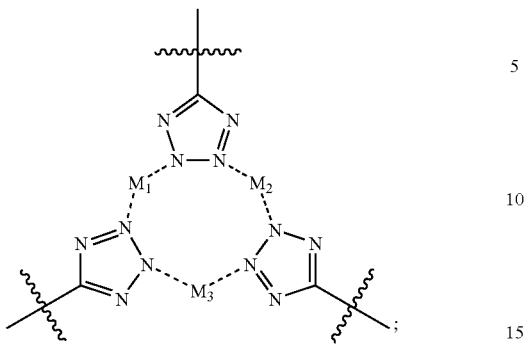

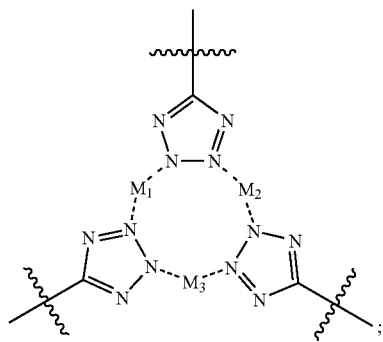

each $L_1$ and $L_3$ is a bond or is $-(L_{11})_m-$ and $-(L_{33})_m-$, respectively, wherein $L_{11}$ and $L_{33}$ are substituted or unsubstituted arylene;

each $L_5$ is a bond or is $-(L_{55})_m-$, wherein $L_{55}$ is substituted or unsubstituted arylene;

each $R_1$ and $R_3$ is a carboxylic acid moiety;

each D ring defines a pyrazolyl, triazolyl, or tetrazolyl ring; and $M_1$, $M_2$, and $M_3$ are metal ions (preferably, copper ions).

In certain other preferred embodiments, the trimer corresponds to Formula (2) wherein:

each A ring is a benzene ring;

the X ring is:

each $L_1$ and $L_3$ is a bond or is $-(L_{11}-L_{111})_m-$ and $-(L_{33}-L_{333})_m-$, respectively, wherein $L_{11}$ and $L_{33}$ are substituted or unsubstituted arylene and $L_{111}$ and $L_{333}$ are —NH—, —C(=O)—NH—, —C(=O)—O—, —$R_y$—O—, —O—C(=O)—NH—, —SO$_2$—NH—, or —NH—C(=O)—NH—, wherein $R_y$ is alkylene;

each $L_5$ is a bond or is $-(L_{55}-L_{555})_m-$, wherein $L_{55}$ is substituted or unsubstituted arylene and $L_{555}$ is —NH—, —C(=O)—NH—, —C(=O)—O—, —O—C(=O)—NH—, —$R_y$—O—, —SO$_2$—NH—, or —NH—C(=O)—NH—, where $R_y$ is alkylene;

each $R_1$ and $R_3$ is a carboxylic acid moiety;

each D ring defines a pyrazolyl, triazolyl, or tetrazolyl ring;

$M_1$, $M_2$, and $M_3$ are metal ions (preferably, copper ions).

Certain particularly preferred metal-organic trimers have the following structures:

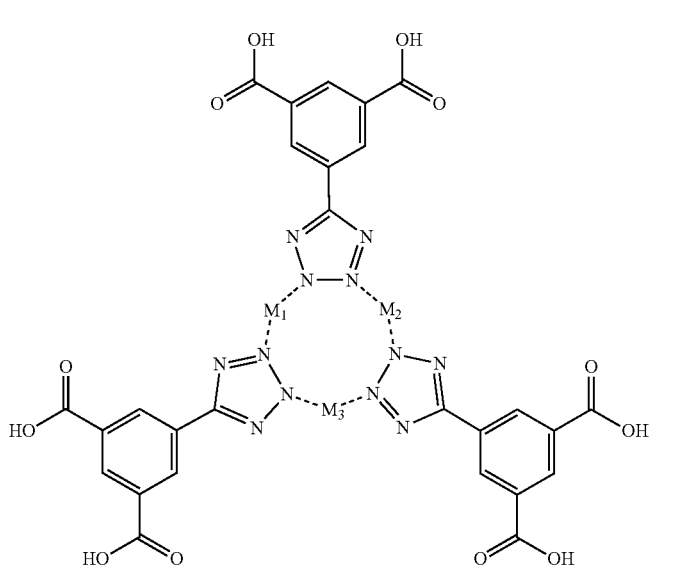

(22C)

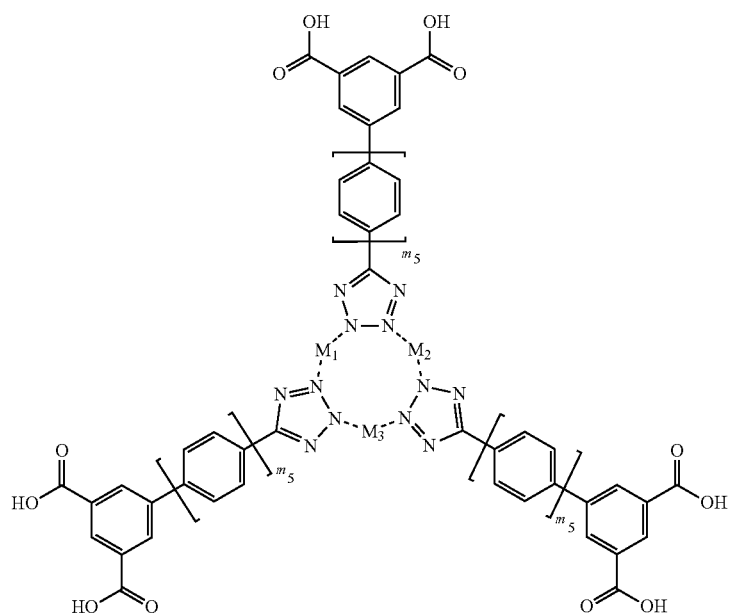
(22D)
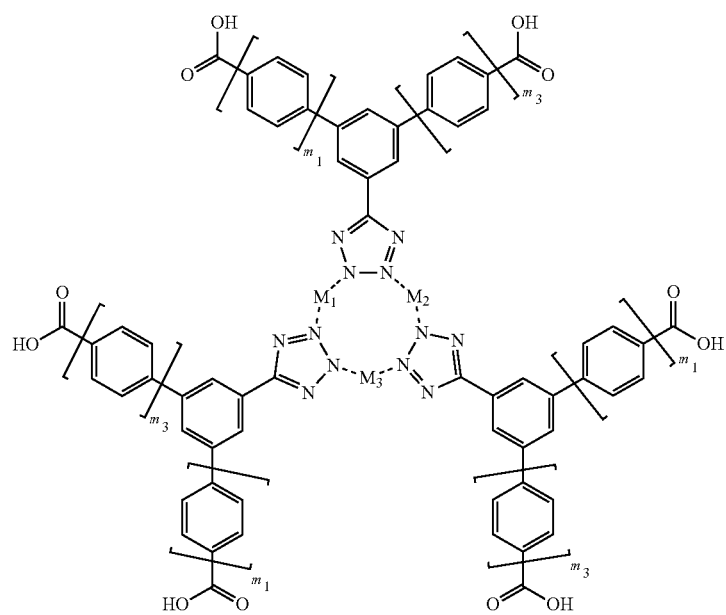
(22E)

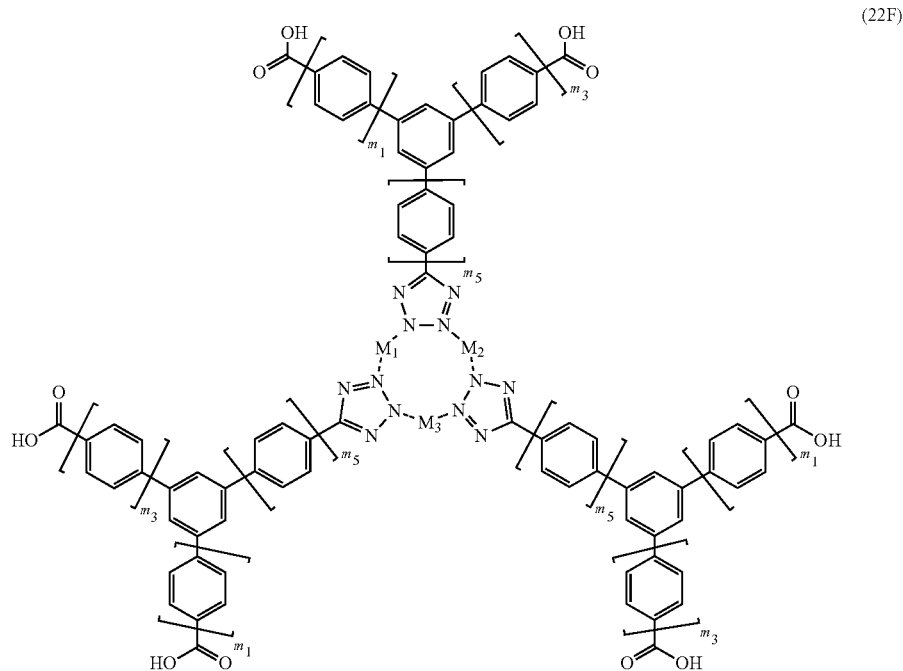

(22F)

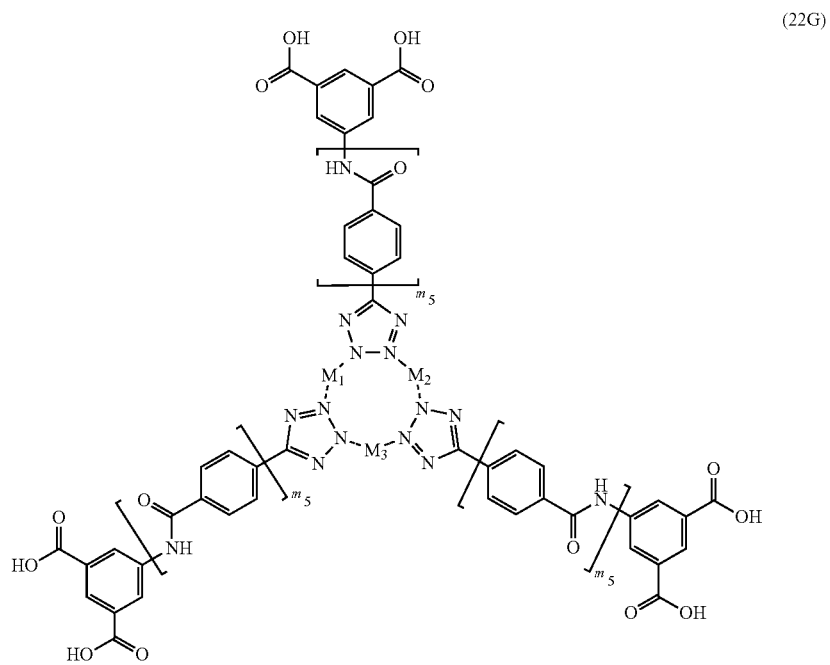

(22G)

wherein in each of Formula (22C), (22D), (22E), (22F), and (22G), each $m_1$ and $m_3$, if present, are 1, 2, or 3, and each $m_5$, if present, is 1, 2, or 3, and $M_1$, $M_2$, and $M_3$ are metal ions. More preferably in these structures, $M_1$, $M_2$ and $M_3$ are copper ions. In the interest of space, the bracketed repeating phenylene moieties are shown as unsubstituted phenylene. It will be appreciated, however, that these phenylene moieties may be substituted with a variety of groups, as discussed in detail above.

Accordingly, in these embodiments the triangular molecular building block is

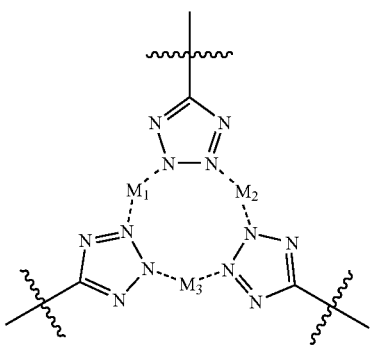

wherein the wavy lines represent the attachment point of the triangular molecular building block to the trimer ligand corresponding to Formula (2) (i.e., at $L_1$, $L_3$, or $L_5$ of each substituent arm) or to the supermolecular building blocks.

As the formulae drawings of the ligand compounds within this specification (e.g., Formulae (1), (2), (22), (222), etc.) (and the supermolecular building blocks including portions of the same) can represent only one of the possible resonance, conformational isomeric, enantiomeric or geometric isomeric forms, it should be understood that the invention encompasses any resonance, conformational isomeric, enantiomeric and/or geometric isomeric forms of the compounds having one or more of the utilities described herein. The present invention contemplates all such compounds, including cis- and trans-isomers, E- and Z-isomers, and other mixtures thereof, falling within the scope of any of the formulae disclosed herein.

Metals

As discussed above, in certain embodiments the nitrogen atoms of the D ring of each monomer coordinate with three metals to form the triangular molecular building blocks. The carboxylate groups at $R_1$ and $R_3$ of the ligand compounds also coordinate with metal ions to form the supermolecular building blocks.

In general, the nitrogen atoms of the D ring of the ligand compound and the nitrogen atoms of the D rings of the trimer ligand can coordinate with metal ions from Groups 1, 2, 3, 4, 5, 6, 7, 8, 9, 10, 11, 12, 13, 14, 15, and 16 (according to the IUPAC Group numbering format) or Groups IA, IIA, IIIB, IVB, VB, VIIB, VIIB, VIII, IB, IIB, IIIA, IVA, VA, and VIA (according to the Chemical Abstracts Service (CAS) numbering format) of the periodic table. This includes, for example, metal ions from the alkali metals, alkaline earth metals, transition metals, Lanthanides, Actinides, and other metals. In order to form building blocks of the desired shape and orientation, a metal ion is selected having the appropriate coordination geometry (e.g., linear, trigonal planar, tetrahedral, square planar, trigonal bipyramidal, square pyramidal, octahedral, trigonal prismatic, pentagonal bipyramidal, cubic, dodecahedral, hexagonal bipyramidal, icosahedron, cuboctahedron, etc.).

The bond angle between the nitrogen chelators of the D ring and the metal generally dictates the topology of the triangular molecular building block, while the $R_1$ and $R_3$ functional groups on each of several (monomer or trimer) ligands coordinate with metal ions to form the rigid supermolecular building block. In a particular embodiment, the supramolecular assemblies of the invention have an rht-topology, based on the triangular orientation of the triangular molecular building block and the rhombicuboctahedral structure of the supermolecular building blocks.

In the triangular molecular building block comprising the metal-organic X ring, the metal ions, $M_1$, $M_2$, and $M_3$, preferably coordinate with two nitrogen atoms of two D rings in a bis-monodentate fashion. Thus, the $M_1$, $M_2$, and $M_3$ metal ions are selected to impart a trigonal geometry to the triangular molecular building block, formed, for example, from an assembled trimer. In one embodiment, the $M_1$, $M_2$, and $M_3$ metal ions are transition metals. In one particular embodiment, the $M_1$, $M_2$, and $M_3$ metal ions are selected from first row transition metals. In another particular embodiment, the $M_1$, $M_2$, and $M_3$ metal ions are selected from second row transition metals. In another particular embodiment, the $M_1$, $M_2$, and $M_3$ metal ions are selected from third row transition metals. In another embodiment, $M_1$, $M_2$, and $M_3$ of the X ring are independently selected from the group consisting of $Ag^+$, $Al^{3+}$, $Au^+$, $Cu^{2+}$, $Cu^+$, $Fe^{2+}$, $Fe^{3+}$, $Hg^{2+}$, $Li^+$, $Mn^{3+}$, $Mn^{2+}$, $Nd^{3+}$, $Ni^{2+}$, $Ni^+$, $Pd^{2+}$, $Pd^+$, $Pt^{2+}$, $Pt^+$, $Tl^{3+}$, $Yb^{2+}$ and $Yb^{3+}$, along with the corresponding metal salt counterion (if present). In one preferred embodiment, $M_1$, $M_2$, and $M_3$ of the X ring are the same and are selected from the group consisting of $Ag^+$, $Au^+$, $Cu^{2+}$, $Cu^+$, $Fe^{2+}$, $Fe^{3+}$, $Hg^{2+}$, $Li^+$, $Mn^{3+}$, $Mn^{2+}$, $Ni^{2+}$, $Ni^+$, $Pd^{2+}$, $Pd^+$, $Pt^{2+}$, and $Pt^+$, along with the corresponding metal salt counterion (if present). In another preferred embodiment, $M_1$, $M_2$, and $M_3$ of the X ring are copper ions along with the corresponding metal salt counterion (if present). Suitable counterions include, for example, $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, and $CO_3^{2-}$.

The functional groups, $R_1$ and $R_3$, of the monomer compound corresponding to Formula (1) and the trimer corresponding to Formula (2) also coordinate to metal ions to form the supermolecular building blocks as discussed elsewhere herein. Preferably, each $R_1$ and $R_3$ functional coordinates to two metals in a square pyramidal geometry. In one embodiment, the metal ions which coordinate to the $R_1$ and $R_3$ functional groups are transition metals. In one particular embodiment, the metal ions which coordinate to the $R_1$ and $R_3$ functional groups are first row transition metals. In another particular embodiment, the metal ions which coordinate to the $R_1$ and $R_3$ functional groups are second row transition metals. In another particular embodiment, the metal ions which coordinate to the $R_1$ and $R_3$ functional groups are third row transition metals. In one embodiment, the metal ions which coordinate to the $R_1$ and $R_3$ functional groups are selected from the group consisting of $Al^{3+}$, $Bi^{5+}$, $Bi^{3+}$, $Bi^+$; $Cd^{2+}$, $Cu^{2+}$, $Cu^+$, $Co^{3+}$, $Co^{2+}$, $Cr^{3+}$, $Eu^{2+}$, $Eu^{3+}$, $Fe^{3+}$, $Fe^{3+}$, $Gd^{3+}$, $Mo^{3+}$, $Ni^{2+}$, $Ni^+$, $Os^{3+}$, $Os^{2+}$, $Pt^{2+}$, $Pt^+$, $Re^{3+}$, $Re^{2+}$, $Rh^{2+}$, $Rh^+$, $Ru^{3+}$, $Ru^{2+}$, $Sm^{2+}$, $Sm^{3+}$, $Tc^{4+}$, $Tc^{6+}$, $Tc^{7+}$, $W^{3+}$, $Y^{3+}$, and $Zn^{2+}$, along with the corresponding metal salt counterion (if present). In one preferred embodiment, the metal ions which coordinate to the $R_1$ and $R_3$ functional groups are the same and are selected from the group consisting of $Bi^{5+}$, $Bi^{3+}$, $Bi^+$; $Cd^{2+}$, $Cu^{2+}$, $Cu^+$, $Co^{3+}$, $Co^{2+}$, $Cr^{3+}$, $Fe^{3+}$, $Fe^{3+}$, $Mo^{3+}$, $Ni^{2+}$, $Ni^+$, $Pt^{2+}$, $Pt^+$, $Re^{3+}$, $Re^{2+}$, $Rh^{2+}$, $Rh^+$, $Ru^{3+}$, $Ru^{2+}$, $W^{3+}$, $Y^{3+}$, and $Zn^{2+}$, along with the corresponding metal salt counterion (if present). In another preferred embodiment, the metal ions which coordinate to the $R_1$ and $R_3$ functional groups are copper ions along with the corresponding metal salt counterion (if present). Suitable counterions include, for example, $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, and $CO_3^{2-}$.

Other suitable coordinating metals include those described in U.S. Pat. No. 5,648,508 (hereby incorporated by reference herein in its entirety). In addition to the metal ions and metal salts described above, other metallic and metal-like compounds may be used, such as sulfates, phosphates, and other complex counterion metal salts of the main- and subgroup metals of the periodic table of the elements. Metal oxides, mixed metal oxides, with or without a defined stoichiometry may also be employed. The metal compounds described herein may be used as a starting material either in the form of a powder or as a shaped body or as any combination thereof.

It will be understood that all metal ions in a given triangular molecular building block or supermolecular building block (or supramolecular assemblies comprising them (e.g., $M_1$, $M_2$, and $M_3$ of the X ring, or coordinated to an $R_1$ and/or $R_3$ functional group), or corresponding metal ions in other building blocks, can be in the same transition state or the trimer or other structure can contain metals in more than one transition state. In some instances, for example, a counterion may be present to balance the charge. The counterions themselves may, or may not, be coordinated to the metal. Suitable counterions are described elsewhere herein.

Supramolecular Building Blocks and Metal-Organic Frameworks

Supramolecular building blocks, and metal-organic frameworks containing them may be synthesized using supermolecular and molecular building blocks comprising metal-containing or organic moieties having different coordination geometries, in combination with a metals and ligands possessing multi- and/or polydentate functional groups. The resulting polyhedra and/or connection networks can occupy a wide variety of one-, two-, and three-dimensional spaces, with multiple, discrete, or infinite layers of polyhedral arrays extending in any of the X, Y, and Z directions of a coordinate reference frame being contemplated. See, for example, Zaworotko et al., U.S. Pat. No. 6,965,026 and Lanahan, U.S. Patent Application Publication No. 2008/0040984 (each of which is hereby incorporated by reference herein in its entirety).

The trimer ligands corresponding to Formula (2) may be combined with other known building units (including monomer ligands corresponding to Formula (1)) to form supermolecular building blocks and triangular molecular building blocks, which may be further combined to form infinite or discrete architectures. For instance, a plurality of metal ions can be used to link a plurality of monomer and trimer ligand compounds corresponding to Formulae (1) or (2), or the plurality of monomer and trimer ligand compounds corresponding to Formulae (1) and (2), metals, and other compounds having multi- and/or polydentate functional groups, to form assemblies.

Another aspect of the present invention, therefore is directed to assemblies, preferably metal-organic assemblies, that can be used in combination with triangular molecular building blocks to construct (24-connected)-based supramolecular assemblies. In certain embodiments, the supermolecular building block includes twelve metal (e.g., copper) paddlewheels joined by twenty four ligand moieties designed to contain three functional groups or substituent arms positioned at 120° bond angles. Preferably, the 5-position of the bent bridging ligand (120° angle) lies on the vertices of a rhombicuboctahedron, the 24-connected vertex figure for the (3,24)-connected rht net. Thus, functionalization at this 5-position with an organic moiety that permits the formation of a rigid triangular building block, leads to the formation of an assembly having an rht-like network topology, since this (3,24)-connected net is the only edge transitive net known for the assembly of 24- and 3-connected vertices. The various supermolecular building blocks and triangular molecular building blocks are linked by covalent, coordinate covalent, noncovalent bonding or a combination thereof.

For example, the trimer corresponding to Formula (2) can be combined with one or more square-shaped building blocks. Certain preferred secondary square-shaped building units are described in Zaworotko et al., U.S. Pat. No. 6,965,026 (hereby incorporated by reference in its entirety). In one embodiment, the square-shaped secondary building unit combined with the ligand corresponding to Formula (1) and/or the trimer corresponding to Formula (2) has the formula: $M_4M_5(-Z)_4$, wherein $M_4$ and $M_5$ are metal ions, and at least one of the four -Z moieties represents one of the —$R_1$ and/or —$R_3$ functional groups of the ligand or trimer corresponding to Formulae (1) or (2). In this embodiment, the square-shaped secondary building unit forms an inorganic paddlewheel geometry. The paddlewheel is dinuclear and comprises two metal ions in the expected square pyramidal geometry, each of the metal ions being coordinated to the functional group of the ligand node (i.e., each —$R_1$ or —$R_3$). The remainder of the square pyramidal coordination geometry is formed by coordination between the two metal ions and other bidentate functional groups, either from the trimer (i.e., at the —$R_1$ and/or —$R_3$ functional groups), or from some other ligand compound having one or more bidentate functional groups. This configuration is generally illustrated as follows:

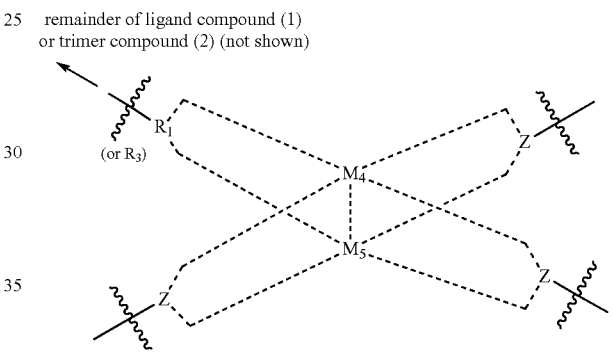

remainder of ligand compound (1) or trimer compound (2) (not shown)

wherein each $R_1$ (or $R_3$) is a bidentate functional group;

$M_4$ and $M_5$ are metal ions;

the dashed lines represent coordination bonds between the bidentate $R_1$ (or $R_3$) functional groups and the metals, $M_4$ and $M_5$, and between the metals themselves; and the wavy lines represent the point of attachment of each $R_1$ (or $R_3$) functional group to the remainder of each of four monomer compounds corresponding to Formula (1) or a trimer corresponding to Formula (2) (not shown in the interest of space).

According to this embodiment, the $M_4$ and $M_5$ metals are selected from the group consisting of $Bi^{5+}$, $Bi^{3+}$, $Bi^+$; $Cd^{2+}$, $Cu^{2+}$, $Cu^+$, $Co^{3+}$, $Co^{2+}$, $Cr^{3+}$, $Eu^{2+}$, $Eu^{3+}$, $Fe^{3+}$, $Fe^{3+}$, $Gd^{3+}$, $Mo^{3+}$, $Ni^{2+}$, $Ni^+$, $Os^{3+}$, $Os^{2+}$, $Pt^{2+}$, $Pt^+$, $Re^{3+}$, $Re^{2+}$, $Rh^{2+}$, $Rh^+$, $Ru^{3+}$, $Ru^{2+}$, $Sm^{2+}$, $Sm^{3+}$, $Tc^{4+}$, $Tc^{6+}$, $Tc^{7+}$, $W^{3+}$, $Y^{3+}$, and $Zn^{2+}$, along with the corresponding metal salt counterion (if present) along with the corresponding metal salt counterion (if present). In a particularly preferred embodiment, $M_4$ and $M_5$ are copper ions.

In other embodiments, each coordinating bifunctional ligand of the paddlewheel is an —$R_1$ or —$R_3$ bifunctional group of the monomer ligand compound corresponding to Formula (1), or the trimer ligand corresponding to Formula (2):

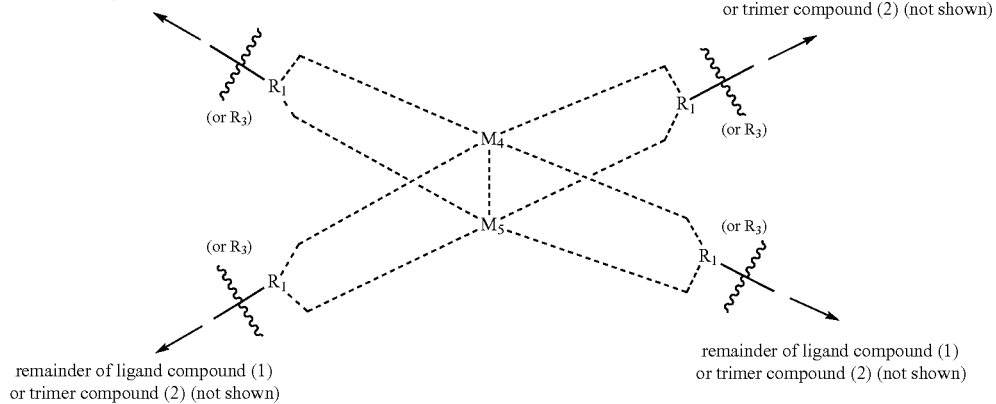

In general, each of the paddlewheel building units are dinuclear, and generally have the configuration illustrated above. The paddlewheel secondary building units comprise two metal ions ($M_4$ and $M_5$) in a square pyramidal geometry, each of which is coordinated to four bidentate functional groups of a monomer or trimer ligand compound (i.e., $R_1$ and $R_3$). Thus, the 12 dimetal secondary building units have the formula:

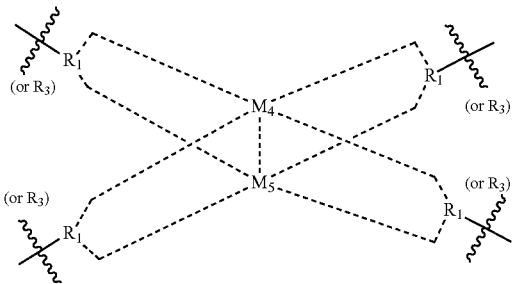

wherein $M_4$ and $M_5$ are metal ions and each —$R_1$ (or —$R_3$) represents the —$R_1$ (or —$R_3$ functional groups of a ligand (e.g., corresponding to Formulae (1) or (2)).

Processes for Preparing Building Units and Building Blocks

One method of forming the supramolecular building blocks described herein comprises the step of dissolving at least one metal salt and at least one ligand compound corresponding to Formula (1), and optionally at least one trimer corresponding to Formula (2) in a solvent to form a solution. The solution is then crystallized to form the supramolecular building block. The crystallizing step may be carried out, for example, by leaving the solution at room temperature, adding a diluted base to the solution to initiate the crystallization, diffusing a diluted base into the solution to initiate the crystallization, and transferring the solution to a closed vessel and heating to a predetermined temperature. The solvent may be any suitable organic solvent. Exemplary organic solvents include, but are not limited to, aprotic dipolar solvents (such as acetone, acetonitrile, dimethylformamide, dimethylacetamide, dimethylsulfoxide, 1-methyl-2-pyrrolidinone, and the like), alcohols (such as methanol, ethanol, tert-butanol, isopropanol, and the like), combinations thereof, and the like. A preferred solvent is dimethylformamide.

Alternatively, the triangular molecular building block can be pre-assembled, e.g., using conventional organic synthesis techniques. The resulting triangular molecular building block may then be combined with at least one metal salt and a ligand corresponding to Formula (1) in a solvent to form a solution. The solution may then be crystallized to form the supramolecular building block.

The metal salt is formed from a metal cation and an anion, the metal being selected from the group of metals discussed above in connection with the ligand compound and the trimer. The anion may be any of a variety of anions, including, for example, $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, $CO_3^{2-}$, and $PF_6^-$, and organic counterions such as acetate ($CH_3CO_2^{2-}$) and triflate ($CF_3SO_3^-$).

In the synthesis of the supermolecular building blocks, triangular molecular building blocks, supramolecular building blocks, and metal-organic frameworks, it will be understood that the moieties possessing bidentate and/or multi- or poly-dentate functional groups may or may not bring with them one or more corresponding counterions, such as, for example, $H^+$, $Li^+$, $Na^+$, $K^+$, $Mg^{2+}$, $Ca^{2+}$, $Sr^{2+}$, ammonia ions, or one or more counterions, such as, for example, $F^-$, $Cl^-$, $Br^-$, $I^-$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, $CO_3^{2-}$, and $PF_6^-$, and organic counterions such as acetate ($CH_3CO_2^{2-}$) and triflate ($CF_3SO_3^-$).

For the most part, the crystalline building blocks, and metal-organic frameworks and assemblies are largely self-assembling, and methods for their preparation will be understood by those of skill in the art using conventional techniques. Examples for the synthesis of metal-organic frameworks and similar materials can be found, for example, in Kim et al., *J. Am. Chem. Soc.* 123, 2001, 8239-8247 or Yaghi et al., *Acc. Chem. Res.* 31, 1998, 474-484.

The separation of the framework materials from the mother liquor of the crystallization may be achieved by procedures known in the art such as solid-liquid separations, centrifugation, extraction, filtration, membrane filtration, cross-flow filtration, flocculation using flocculation adjuvants (nonionic, cationic, and anionic adjuvants), or by the addition of pH shifting additives such as salts, acids, or bases, as well as by evaporation of the mother liquor at elevated temperatures and/or in vacuo and concentration. The desired end use of the resulting framework may dictate which separation method(s) is/are ultimately selected.

Uses of Building Blocks and Metal-Organic Frameworks

Resulting supramolecular building blocks including polyhedra and polymeric structures which may be prepared using the ligand (monomer and trimer) compounds and building blocks including them are useful in numerous applications because of their novel and desirable structures, and properties.

For example, the inherent porosity of the building blocks and assemblies can be exploited in gas storage, separations, chemosensors, biosensors, remediation of environmental pollutants, drug delivery, and other applications. Polyhedra and arrays thereof formed from the building blocks and assemblies of the invention can exhibit high thermal motion, which makes them useful for liquid crystalline, lubricants, and thermoelectric materials. Building blocks and supramolecular assemblies can exhibit magnetic properties, which make them useful for information storage or sensing. Supramolecular assemblies described herein can have the ability to bind to biomolecules, making them useful in the formation of biomaterials, or for therapeutic applications. Metal organic frameworks and assemblies having excited state photochemistry are useful as fluorescent or luminescent probes. The solubility of building blocks and assemblies described herein make them useful as additives to polymers. In addition, their redox properties make the assemblies and building blocks useful for applications which require electron storage and transfer. Moreover, the building blocks, frameworks, and assemblies comprising the ligand compounds, trimers, and metals described herein can be formed as a shaped body containing an active material, such as a catalytic or pharmaceutically active material. Methods for forming a building block, framework, or assembly including an active material can be found, for example, in Mueller et al., U.S. Pat. No. 6,893,564 (hereby incorporated by reference herein in its entirety).

The uniqueness of the rht net described above and illustrated in the Figures is beneficial to the practice of isoreticular chemistry, where higher surface areas and larger free pore volumes can be easily achieved through expansion of the bifunctional organic linker. As illustrated in FIGS. 1A, 1B, and 1C, an approach to construct highly porous MOFs based on the hierarchical bottom up assembly of supermolecular building blocks and triangular building blocks is presented. This represents a new pathway for the assembly of predetermined highly coordinated structures based on supermolecules, as well as an alternate route to construct multinodal nets based on pre-designed heterofunctional ligands and metal clusters. Construction of isoreticular MOFs based on rht topology from various bifunctional ligands, as well as tritopic hexacarboxylate ligands, containing three 1,3-BDC moieties analogous to the trigonal 1,3-BDC units generated from the metal based trimers disclosed herein can serve as platforms for many applications.

The low density of the fully evacuated rht-based MOF compounds, their large accessible windows, open cavities, large surface areas and accessible free volume and charged nature offer great potential for their exploration in energy related application such as, for example, gas storage, namely $H_2$, methane and $CO_2$ sequestration. Metal-organic frameworks with rht topology can also be employed as drug delivery agents. Indeed, the presence of large cages (ranging from 13 Å to >25 Å depending on the framework) and high pore volumes is suitable for the high drug loading capacity. The ability to control the pore size as well as the cavities functionalization using different metal centers and or functionalized linkers will allow the control of the drug release. The large potential repertoire of rht-types of metal-organic frameworks would can serve as platforms for catalysis and separation.

Abbreviations and Definitions

The following definitions and methods are provided to better define the present invention and to guide those of ordinary skill in the art in the practice of the present invention. Unless otherwise noted, terms are to be understood according to conventional usage by those of ordinary skill in the relevant art.

The terms "acetal" and "ketal," as used herein alone or as part of another group, denote the moieties represented by the following formulae, respectively:

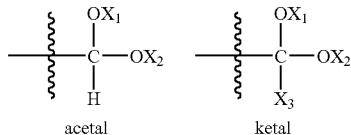

wherein $X_1$ and $X_2$ are independently hydrocarbyl, substituted hydrocarbyl, heterocyclo, or heteroaryl, and $X_3$ is hydrocarbyl or substituted hydrocarbyl, as defined in connection with such terms, and the wavy lines represent the attachment point of the acetal or ketal moiety to another moiety or compound.

The term "acyl," as used herein alone or as part of another group, denotes the moiety formed by removal of the hydroxy group from the group —COOH of an organic carboxylic acid, e.g., $X_4C(O)$—, wherein $X_4$ is $X^1$, $X^1O$—, $X^1X^2N$—, or $X^1S$—, $X^1$ is hydrocarbyl, heterosubstituted hydrocarbyl, or heterocyclo, and $R^2$ is hydrogen, hydrocarbyl or substituted hydrocarbyl. Exemplary acyl moieties include acetyl, propionyl, benzoyl, pyridinylcarbonyl, and the like.

The term "acyloxy," as used herein alone or as part of another group, denotes an acyl group as described above bonded through an oxygen linkage (—O—), e.g., $X_4C(O)O$— wherein $X_4$ is as defined in connection with the term "acyl."

The term "alkoxy," as used herein alone or as part of another group, denotes an —$OX_5$ radical, wherein $X_5$ is as defined in connection with the term "alkyl." Exemplary alkoxy moieties include methoxy, ethoxy, propoxy, or 2-propoxy, n-, iso-, or tert-butoxy, and the like.

The term "alkenoxy," as used herein alone or as part of another group, denotes an —$OX_6$ radical, wherein $X_6$ is as defined in connection with the term "alkenyl." Exemplary alkenoxy moieties include ethenoxy, propenoxy, butenoxy, hexenoxy, and the like.

The term "alkynoxy," as used herein alone or as part of another group, denotes an —$OX_7$ radical, wherein $X_7$ is as defined in connection with the term "alkynyl." Exemplary alkynoxy moieties include ethynoxy, propynoxy, butynoxy, hexynoxy, and the like.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkylene," as used herein alone or as part of another group, denotes a linear saturated divalent hydrocarbon radical of one to eight carbon atoms or a branched saturated divalent hydrocarbon radical of three to six carbon atoms unless otherwise stated. Exemplary alkylene moieties include methylene, ethylene, propylene, 1-methylpropylene, 2-methylpropylene, butylene, pentylene, and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "amine" or "amino," as used herein alone or as part of another group, represents a group of formula —N($X_8$)($X_9$), wherein $X_8$ and $X_9$ are independently hydrogen, hydrocarbyl, substituted hydrocarbyl, heteroaryl, or heterocyclo, or $X_8$ and $X_9$ taken together form a substituted or unsubstituted alicyclic, aryl, or heterocyclic moiety, each as defined in connection with such term, typically having from 3 to 8 atoms in the ring. "Substituted amine," for example, refers to a group of formula —N($X_8$)($X_9$), wherein at least one of $X_8$ and $X_9$ are other than hydrogen. "Unsubstituted amine," for example, refers to a group of formula —N($X_8$)($X_9$), wherein $X_8$ and $X_9$ are both hydrogen.

The terms "amido" or "amide," as used herein alone or as part of another group, represents a group of formula —CON($X_8$)($X_9$), wherein $X_8$ and $X_9$ are as defined in connection with the terms "amine" or "amino." "Substituted amide," for example, refers to a group of formula —CON($X_8$)($X_9$), wherein at least one of $X_8$ and $X_9$ are other than hydrogen. "Unsubstituted amido," for example, refers to a group of formula —CON($X_8$)($X_9$), wherein $X_8$ and $X_9$ are both hydrogen The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "arylene", as used herein alone or part of another group refers to a divalent aryl radical of one to twelve carbon atoms. Non-limiting examples of "arylene" include phenylene, pyridinylene, pyrimidinylene and thiophenylene.

The terms "alkaryl" or "alkylaryl," as used herein alone or as part of another group, denotes an -(arylene)-$X_{11}$ radical, wherein $X_{11}$ is as defined in connection with the term "alkyl."

The term "cyano," as used herein alone or as part of another group, denotes a group of formula —CN.

The term "carbocyclic" as used herein alone or as part of another group refers to a saturated or unsaturated monocyclic or bicyclic ring in which all atoms of all rings are carbon. Thus, the term includes cycloalkyl and aryl rings. The carbocyclic ring(s) may be substituted or unsubstituted. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "cycloalkyl," as used herein alone or as part of another group, denotes a cyclic saturated monovalent bridged or non-bridged hydrocarbon radical of three to ten carbon atoms. Exemplary cycloalkyl moieties include cyclopropyl, cyclobutyl, cyclopentyl, cyclohexyl, or adamantyl. Additionally, one or two ring carbon atoms may optionally be replaced with a —CO— group.

The term "ester," as used herein alone or as part of another group, denotes a group of formula —COO$X_{12}$ wherein $X_{12}$ is alkyl or aryl, each as defined in connection with such term.

The term "ether," as used herein alone or as part of another group, includes compounds or moieties which contain an oxygen atom bonded to two carbon atoms. For example, ether includes "alkoxyalkyl" which refers to an alkyl, alkenyl, or alkynyl group substituted with an alkoxy group.

The terms "halide," "halogen" or "halo" as used herein alone or as part of another group refer to chlorine, bromine, fluorine, and iodine.

The term "heteroatom" shall mean atoms other than carbon and hydrogen.

The term "heteroaromatic" or "heteroaryl" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroarylene" as used herein alone or as part of another group refers to a divalent heteroaryl radical. Non-limiting examples of "heteroarylene" include furylene, thienylene, pyridylene, oxazolylene, pyrrolylene, indolylene, quinolinylene, or isoquinolinylene and the like.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "hydroxy," as used herein alone or as part of another group, denotes a group of formula —OH.

The term "keto," as used herein alone or as part of another group, denotes a double bonded oxygen moiety (i.e., =O).

The term "nitro," as used herein alone or as part of another group, denotes a group of formula —$NO_2$ The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters, ethers, and thioethers.

The term "thioether," as used herein alone or as part of another group, denotes compounds and moieties that contain a sulfur atom bonded to two different carbon or hetero atoms (i.e., —S—), and also includes compounds and moieties containing two sulfur atoms bonded to each other, each of which is also bonded to a carbon or hetero atom (i.e., dithioethers (—S—S—)). Examples of thioethers include, but are not limited to, alkylthioalkyls, alkylthioalkenyls, and alkylthioalkynyls. The term "alkylthioalkyls" includes compounds with an alkyl, alkenyl, or alkynyl group bonded to a sulfur atom that is bonded to an alkyl group. Similarly, the term "alkylthioalkenyls" and alkylthioalkynyls" refer to compounds or moieties where an alkyl, alkenyl, or alkynyl group is bonded to a sulfur atom that is covalently bonded to an alkynyl group.

The term "thiol," as used herein alone or as part of another group, denotes a group of formula —SH.

Having described the invention in detail, it will be apparent that modifications and variations are possible without departing the scope of the invention defined in the appended claims. Furthermore, it should be appreciated that all examples in the present disclosure are provided as non-limiting examples.

Example 1

Preparation of 5-tetrazolylisophthalic acid ($H_3TZI$)

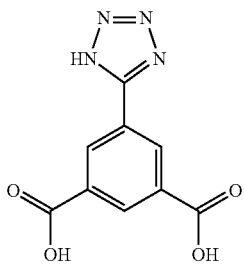

$H_3TZI$ was obtained pure from 5-cyanoisophthalic acid with a 33.3% yield using the Demko-Sharpless method. Demko et al., *J. Org. Chem.* 2001, 66, 7945-7950. The 5-cyanoisophthalic acid was synthesized from 5-aminoisophthalic acid. Ritzén et al., *Eur. J. Org. Chem.* 2000, 3771-3782.

$^1$H NMR ($CDCl_3$, 400 MHz): ppm 8.58 (s, 1H), 8.81 (s, 2H).

Example 2

Preparation of rht-1

A solution of $Cu(NO_3)_2.2.5H_2O$ (0.08 mmol) and $H_3TZI$ (0.056 mmol) in 1.5 mL of DMF and 0.5 mL of ethanol was prepared. The solution was then heated to 85° C. for 12 h, pure blue-green crystals were obtained.

Crystal data: $Cu(C_9H_3N_4O_4)_{0.5}(NO_3)_{0.167}(O^{2-})_{0.167}$: $M_r$=36888.8, cubic, Fm-3m, a=44.358(8) Å, V=87280(27) Å3, Z=192

Example 3

Preparation of 4'-(1H-tetrazol-5yl)biphenyl-3,5-dicarboxylic acid

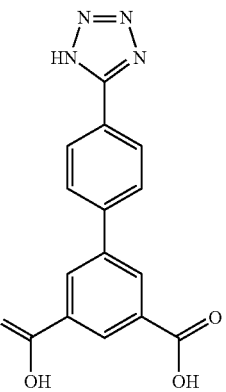

Preparation of Dimethyl 4'-cyanobiphenyl-3,5-dicarboxylate: A solution of dimethyl 5-iodoisophthalate (6 g, 18.75 mmol, 1 eq.), 4-cyanophenylboronic acid (2.95 g, 19.68 mmol, 1.05 eq.) and $Na_2CO_3$ (7.95 g, 74.98 mmol, 4 eq.) in 400 mL of MeOH was degassed by 4 thaw-freeze-pump cycles. Then 1.3 g of 5% Pd/C was added and nitrogen gas was bubbled through the solution for 10 min. The reaction under stirring was carried out at 80° C. for 1 h. Then, the mixture was filtered and washed with EtOH and $CH_2Cl_2$. All organic solvents were removed under vacuum and aqueous layer was extracted 4 times with $CH_2Cl_2$, the recombined organic layer were washed once with $H_2O$, dried over $MgSO_4$, filtered and evaporated under vacuum. An off-white solid was obtained with 85% yield.

Preparation of dimethyl 4'-(1H-tetrazol-5yl)biphenyl-3,5-dicarboxylate: A solution of dimethyl 4-cyano-phenyl-3',5'-dicarboxylate (4.8 g, 17.96 mmol, 1 eq.), sodium azide (2.3 g, 35.92 mmol, 2 eq.), $ZnBr_2$ (2 g, 8.98 mmol, 0.5 eq.) in 75 mL of $H_2O$/iPrOH (2/1) was warmed to 100° C. for 48 h. Then, 200 mL of AcOEt and 150 mL of HCl 3N was added. The aqueous layer was extracted 3 times with 50 mL of AcOEt and the organic layers recombined were dried, filtered and solvent was removed, providing a white solid (99% yield).

A solution of dimethyl 4'-(1H-tetrazol-5yl)biphenyl-3,5-dicarboxylate (10 mmol, 1 eq.) in 50 mL of an 1N aqueous solution of NaOH and 200 mL of ethanol was heated at 80° C. for 2 h. After removing the ethanol under vacuum, the solution was filtered in order to remove the starting material. Then, the solution was acidified with 2N aqueous solution HCl until pH 3. The precipitate formed was collected by filtration, well washed with a 0.5N aqueous solution of HCl, and dried for 2 h in an oven connected to a vacuum at 80° C. A white solid was obtained with 99% yield.

$^1$H NMR (d-DMSO, 400 MHz): ppm 7.91 (d, J=7.8 Hz, 2H), 8.17 (d, J=7.8 Hz, 2H), 8.46 (s, 2H), 8.48 (s, 1H).

Example 4

Preparation of rht-2

A solution of $Cu(NO_3)_2.2.5H_2O$ (0.168 mmol) and 4'-(1H-tetrazol-5yl)biphenyl-3,5-dicarboxylic acid (0.112 mmol) in 1 mL of DMF was prepared. The solution was then heated to 75° C. for 20 h, pure blue-green crystals were obtained.

Crystal data: $Cu(C_{15}H_7N_4O_4)_{0.5}(NO_3)_{0.167}(O^{2-})_{0.167}$: $M_r$=44193.5, cubic, Fm-3m, a=54.722(3) Å, V=163867(57) Å$^3$, Z=192

Example 5

Preparation of 5'-(1H-tetrazol-5yl)-1,1':3',1''-terphenyl-4,4''-dicarboxylic acid

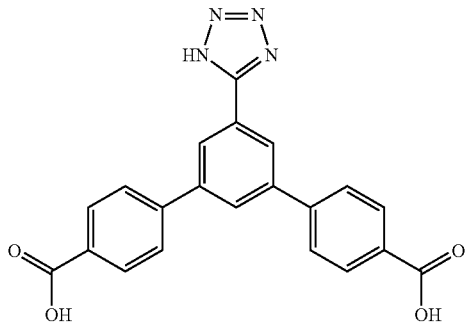

Preparation of 5'-cyano-1,1':3',1''-terphenyl-4,4''-dicarboxylic acid: A solution of 3,5-dibromocyanobenzene (3 g, 11.5 mmol, 1 eq.), 4-carboxyphenyl boronic acid (4 g, 24.1 mmol, 2.1 eq.) and $Na_2CO_3$ (9.8 g, 92 5 mmol, 8 eq.) in 200 mL of EtOH was degassed by 4 thaw-freeze-pump cycles. Then 1.5 g of 5% Pd/C was added and nitrogen gas is bubbled through the solution for 10 min. The reaction under stirring was carried out at 80° C. for 1 h. Then, the mixture was filtered and washed with EtOH and $CH_2Cl_2$. All organic solvents were removed under vacuum and aqueous layer was extracted 4 times with $CH_2Cl_2$, the recombined organic layer were washed once with $H_2O$, dried over $MgSO_4$, filtered and evaporated under vacuum. An off-white solid was obtained with 85% yield.

A solution of 5'-cyano-1,1':3',1''-terphenyl-4,4''-dicarboxylic acid (1 g, 2.86 mmol, 1 eq.), sodium azide (0.378 g, 5.8 mmol, 2.03 eq.), $NH_4Cl$ (0.329 g, 6.2 mmol, 2.15 eq.) in 20 mL of dimethylformamide was warmed to 100° C. for 24 h. Then, after cooling 3N aqueous solution of HCl was added until pH 1-2, the solid remaining was collected by filtration, well washed with $H_2O$ and dried in the oven under vacuum at 80° C. for 2 h. A white solid was obtained quantitatively.

$^1$H NMR (d-DMSO, 400 MHz): ppm 8.03 (d, J=7.9 Hz, 4H), 8.11 (d, J=7.9 Hz, 4H), 8.28 (s, 1H), 8.43 (s, 2H), 13.09 (s, 2H).

Example 6

Preparation of Rht-3

A solution of $Cu(NO_3)_2.2.5H_2O$ (0.168 mmol) and 5'-(1H-tetrazol-5yl)-1,1':3',1''-terphenyl-4,4''-dicarboxylic acid (0.112 mmol) in 1 mL of DMF was prepared. The solution was then heated to 75° C. for 20 h, pure blue-green crystals were obtained.

Crystal data: $Cu(C_{21}H_{11}N_4O_4)_{0.5}(NO_3)_{0.167}(O^{2-})_{0.167}$: $M_r$=51498.4, cubic, Fm-3m, a=63.931 (1) Å, V=261298(27) Å$^3$, Z=192

Example 7

Preparation of 5,5',5''-[1,3,5-phenyltri(methoxy)]triisophthalic acid ($H_6$PTMOI)

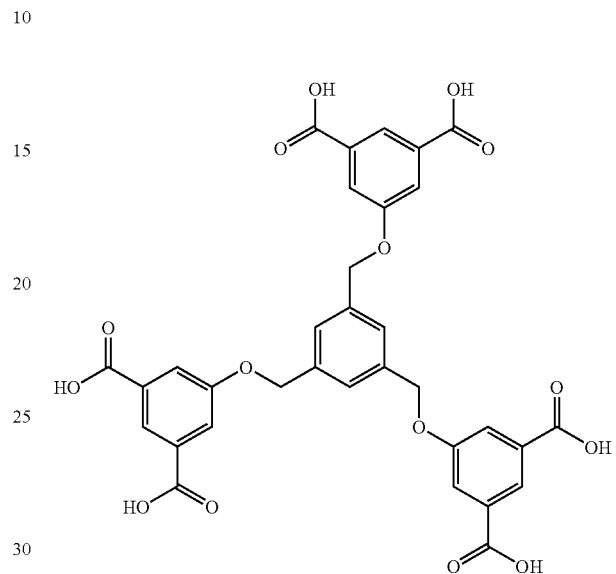

Synthesis of 5,5',5''-[1,3,5-phenyltri(methoxy)]tri-methylisophthalate: A solution of Dimethyl-5-hydroxyisophthalate (2.1 g, 10 mmol, 5 eq.), Potassium carbonate (4.3 g, 31 mmol, 15 eq.) and Potassium iodide (0.125 g, 0.75 mmol, 0.37 eq.) in 50 mL dimethylformamide was heated to 100° C. and stirred for 1H. A solution of 1,3,5-Tris(bromomethyl)benzene (0.71 g, 2 mmol, 1 eq.) in 10 mL of dimethylformamide was then added dropwise to the above heated mixture. The mixture was subsequently stirred and heated at 100° C. for 4H. After cooling to room temperature, 200 mL of distilled water, the precipitate was then collected by filtration after several washes with cold distilled water and air dried. A white solid was obtained with 87% yield.

To the 5,5',5''-[1,3,5-phenyltri(methoxy)]tri-methylisophthalate was added 40 mL of methanol and 1 g of sodium hydroxide in 10 mL of distilled water. The mixture was then stirred for 12 hours at 50° C. After cooling to room temperature, the solution was placed in an ice bath and acidified to pH ~2 with hydrochloric acid 3N. The precipitate was then collected and dried after several washes with cold distilled water. A brownish solid was obtained with 98% yield.

Example 8

Preparation of rht-4

A solution of $Cu(NO_3)_2.2.5H_2O$ (0.084 mmol) and $H_6$PTMOI (0.056 mmol) in 1 mL of DMF and 1 mL of water was prepared. The solution was then heated to 85° C. for 12 h and then 105° C. for 23 h, pure blue-green crystals were obtained.

Crystal data: $Cu_{12}C_{132}H_{72}O_{89}$: $M_r$=30755.1, cubic, Fm-3m, a=41.445(3) Å, V=71189(10) Å$^3$, Z=8

Example 9

Analysis

Figure 4:
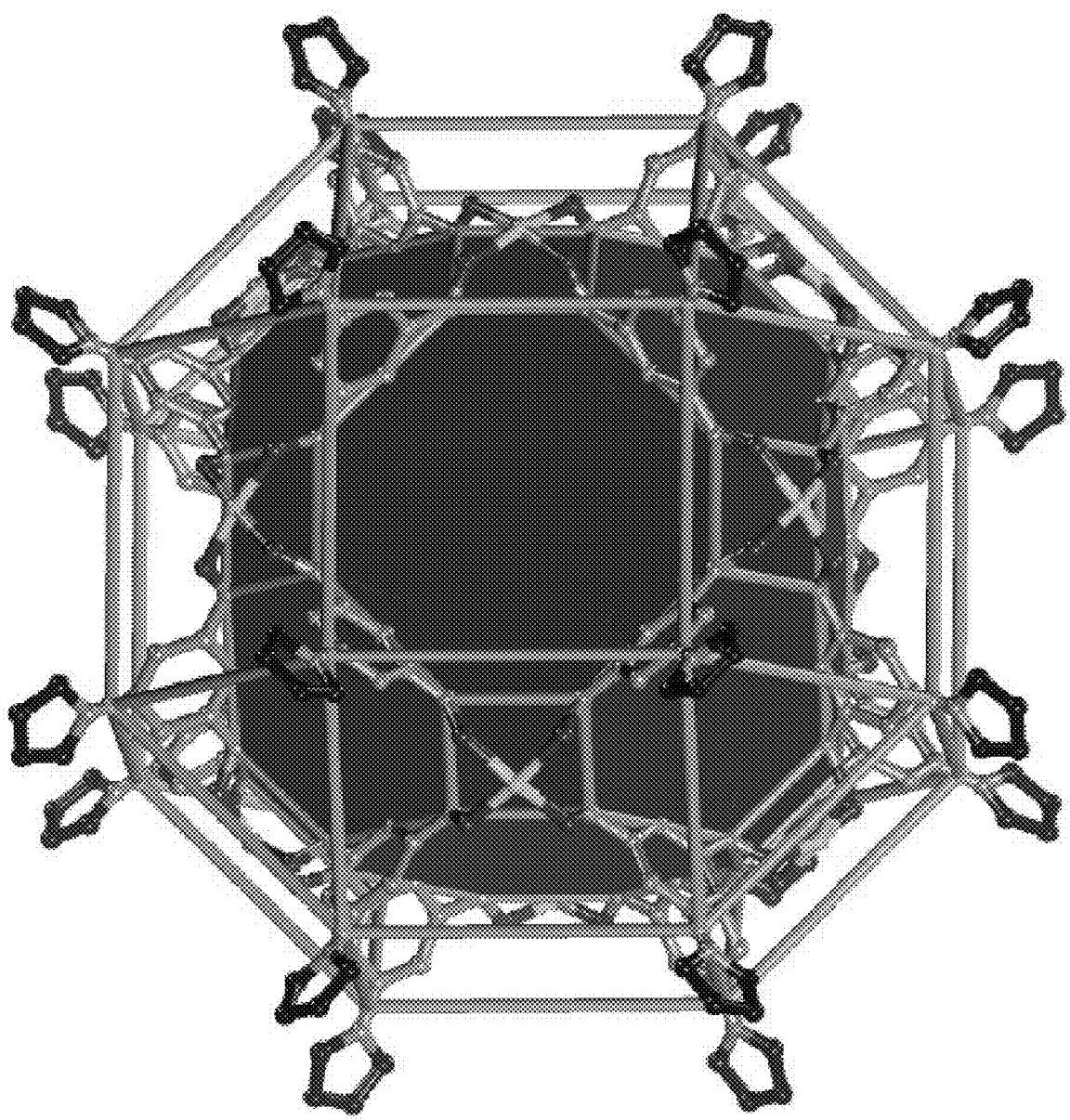
FIG. 4 illustrates a metal-organic truncated cuboctahedral SBB. The 5-position of the isophthalate ligands in the truncated cuboctahedron (purple) SBB sits directly on the vertices of the rhombicuboctahedron (orange frame) serving as the TBU.
Figure 5A:
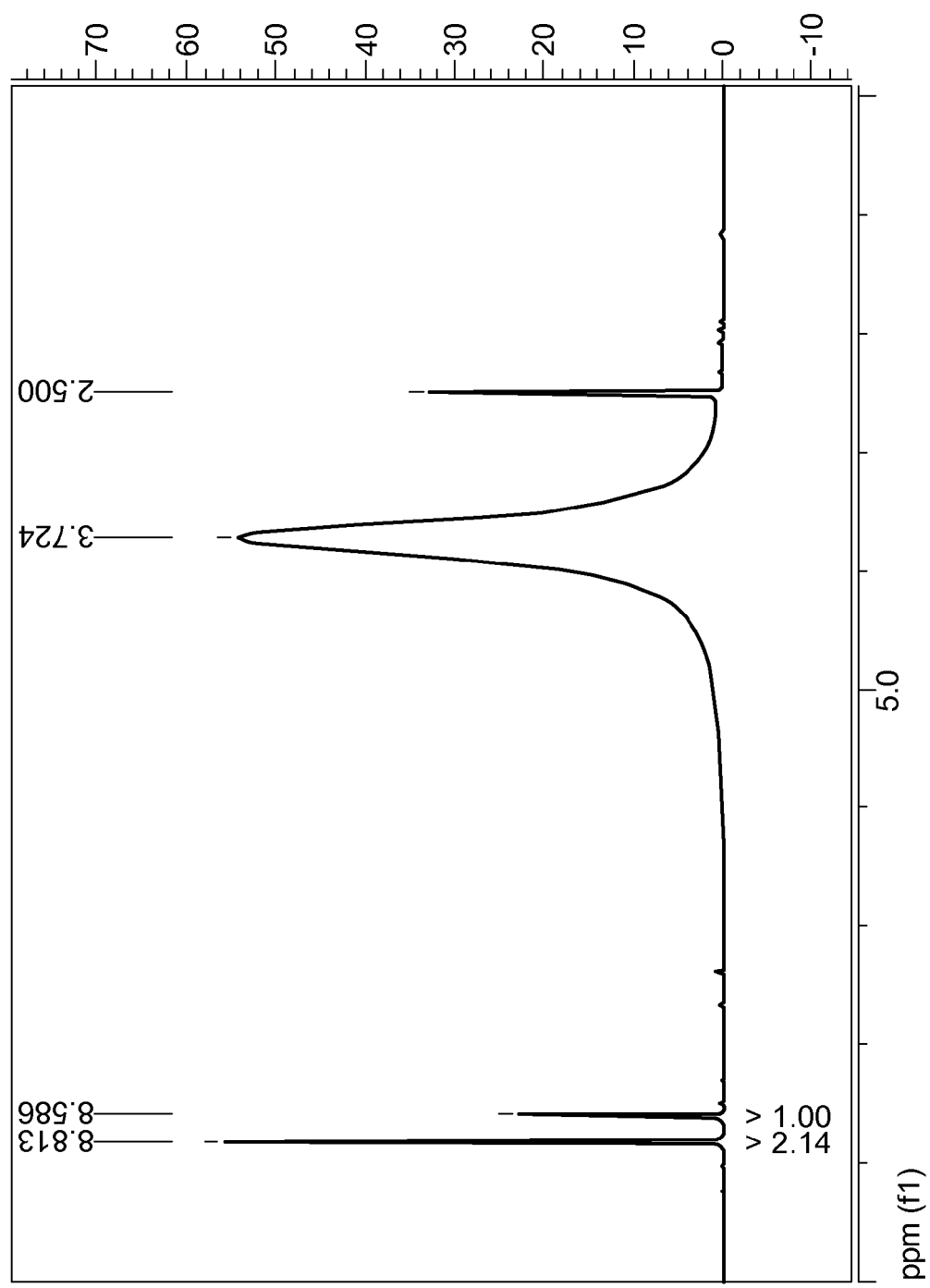
FIG. 5A is a graph depicting the 1H NMR spectrum of 5-tetrazolylisophthalic acid (in DMSO).
Figure 5B:
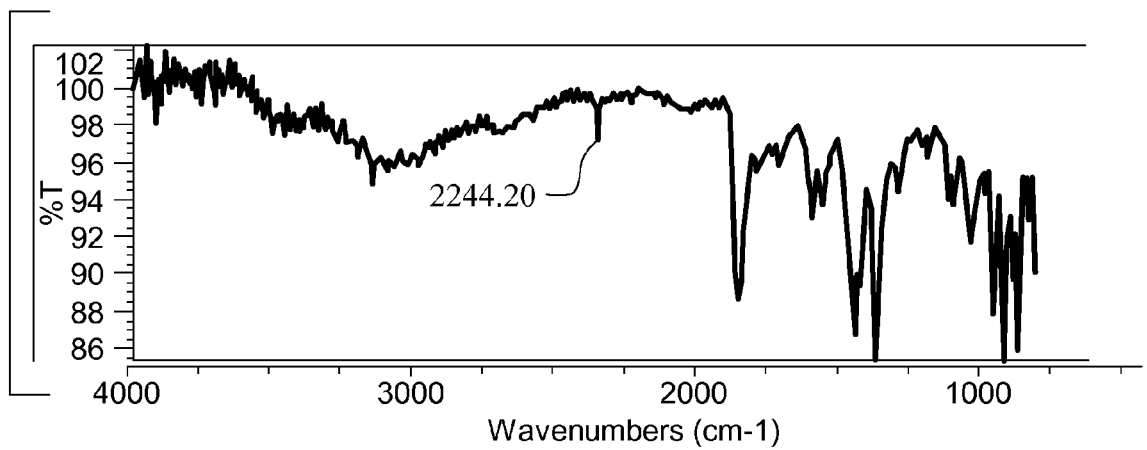
FIGS. 5B and 5C are IR comparisons of 5-cyanoisophthalic acid (FIG. 5B) and 5-tetrazolylisophthalic acid (FIG. 5C) showing loss of the CN stretch at 2244.2 $cm^{-1}$.
Figure 5C:
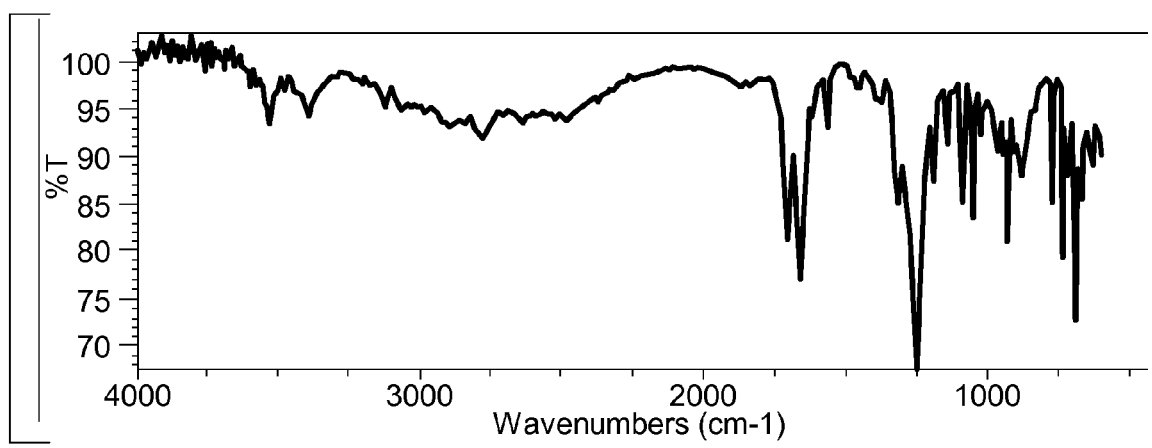
Figure 6:
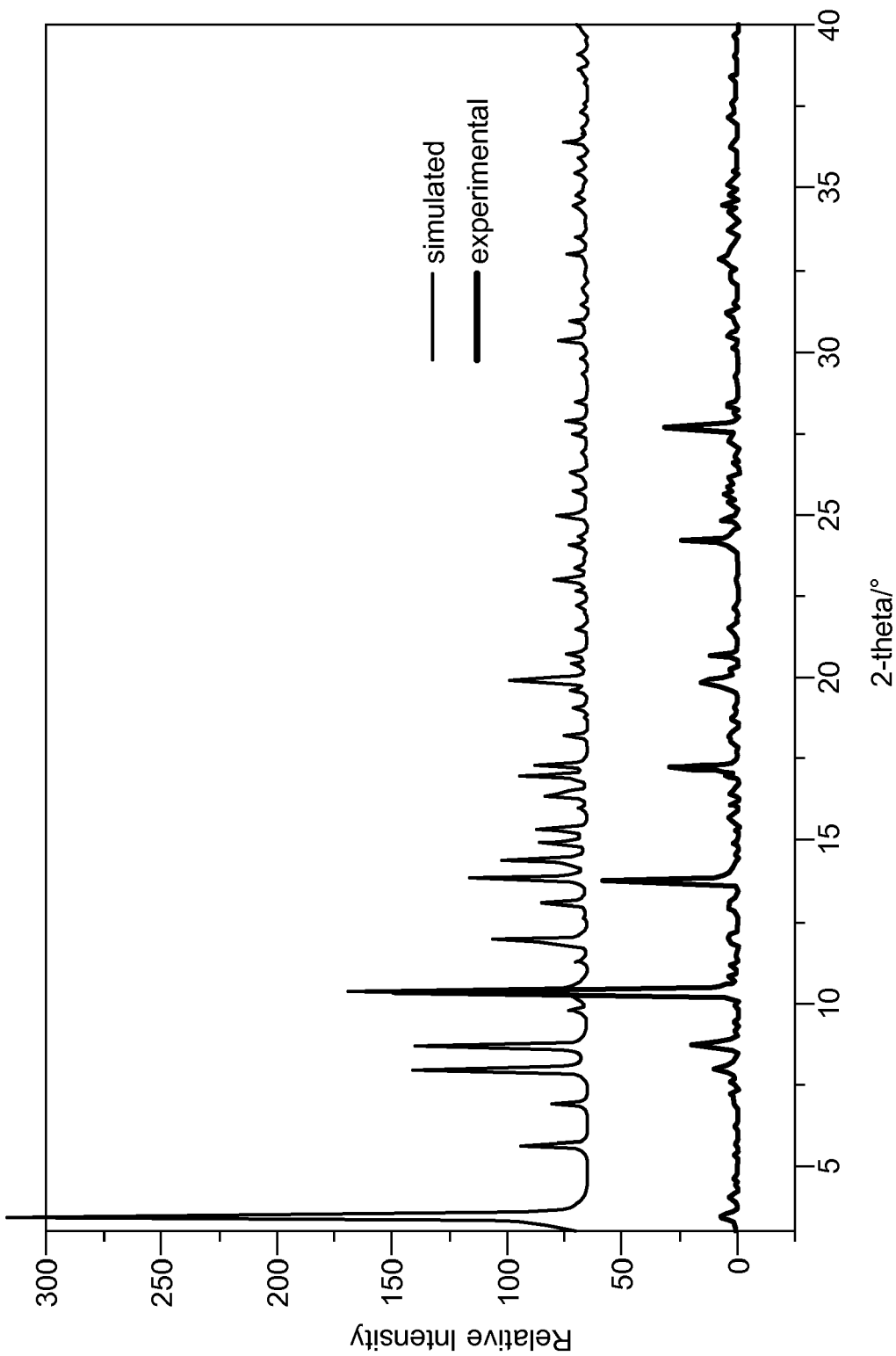
FIG. 6 is a graph depicting experimental and simulated powder X-ray diffraction patters for [1], indicating the phase purity of the as-synthesized product.

Herein, we report the use of metal-organic truncated cuboctahedral SBBs (FIG. 4), generated in situ, as rhombicuboctahedral TBUs to construct a (24-connected)-based MOF (FIG. 1). The SBB consists of 12 copper paddlewheels joined by 24 1,3-benzenedicarboxylate (BDC) linkers so that the 5-position of the bent bridging ligand (120° angle) lies exactly on the vertices of the rhombicuboctahedron, the 24-connected vertex figure for the (3,24)-connected rht net (Delgado-Friedrichs, O. and O'Keeffe *Acta Cryst.* 2007, A63, 344-347).

Indeed, reaction between 5-tetrazolylisophthalic acid $(H_3TZI)^{11}$ and $Cu(NO_3)_2 \cdot 2.5H_2O$ in an N,N-dimethylformamide/ethanol solution yields a homogeneous crystalline material, purity confirmed by similarities between simulated and experimental X-ray powder diffraction (XRPD) patterns, having an rht-like network topology. The as-synthesized compound, characterized by single crystal X-ray diffraction as $[Cu_6O(TZI)_3(H_2O)_9(NO_3)]_n \cdot (H_2O)_{15}$ (1), reveals a crystal structure consisting of truncated cuboctahedra (24 functionalized isophthalate ligands connected by twelve $Cu_2(O_2CR)_4$ paddlewheels) connected to trigonal $Cu_3O(N_4CR)_3$ trimers through each tetrazolate ($N_4CR$) moiety, which is novel for tetrazolate ligands. Each inorganic paddlewheel MBB is dinuclear and consists of two copper ions with the expected square pyramidal geometry, each coordinated to four oxygen atoms of four carboxylates and one water molecule, $CuO_5$. Both carboxylate moieties of the tri ply deprotonated TZI ligand coordinate in a bis-monodentate fashion to two copper atoms to form the $Cu_2(O_2CR)_4$ MBBs, which combine in a cis fashion to form the finite truncated cuboctahedron. Each tetrazolate moiety also coordinates in a bis-monodentate fashion to two copper atoms of the $Cu_3O(N_4CR)_3$ trimer. Each copper atom of the trimer is coordinated to two nitrogen atoms of the tetrazolate, an oxygen core, and one oxygen atom of a terminal water molecule in one plane and one oxygen atom of a disordered water molecule to give square pyramidal geometry, $CuN_2O_3$. The formation of the oxo trimer with the tetrazolate portion of the TZI ligands results in a 24-connected SBB, formed via the isophthalate portion, linked to 12 neighboring SBBs through 24 trigonal metal-tetrazole trimers. This results in a (3,24)-connected MOF that has only recently been depicted by Delgado-Friedrichs and O'Keeffe as having rht-like topology. Delgado-Friedrichs, O. and O'Keeffe *Acta Cryst.* 2007, A63, 344-347.

Figure 7:
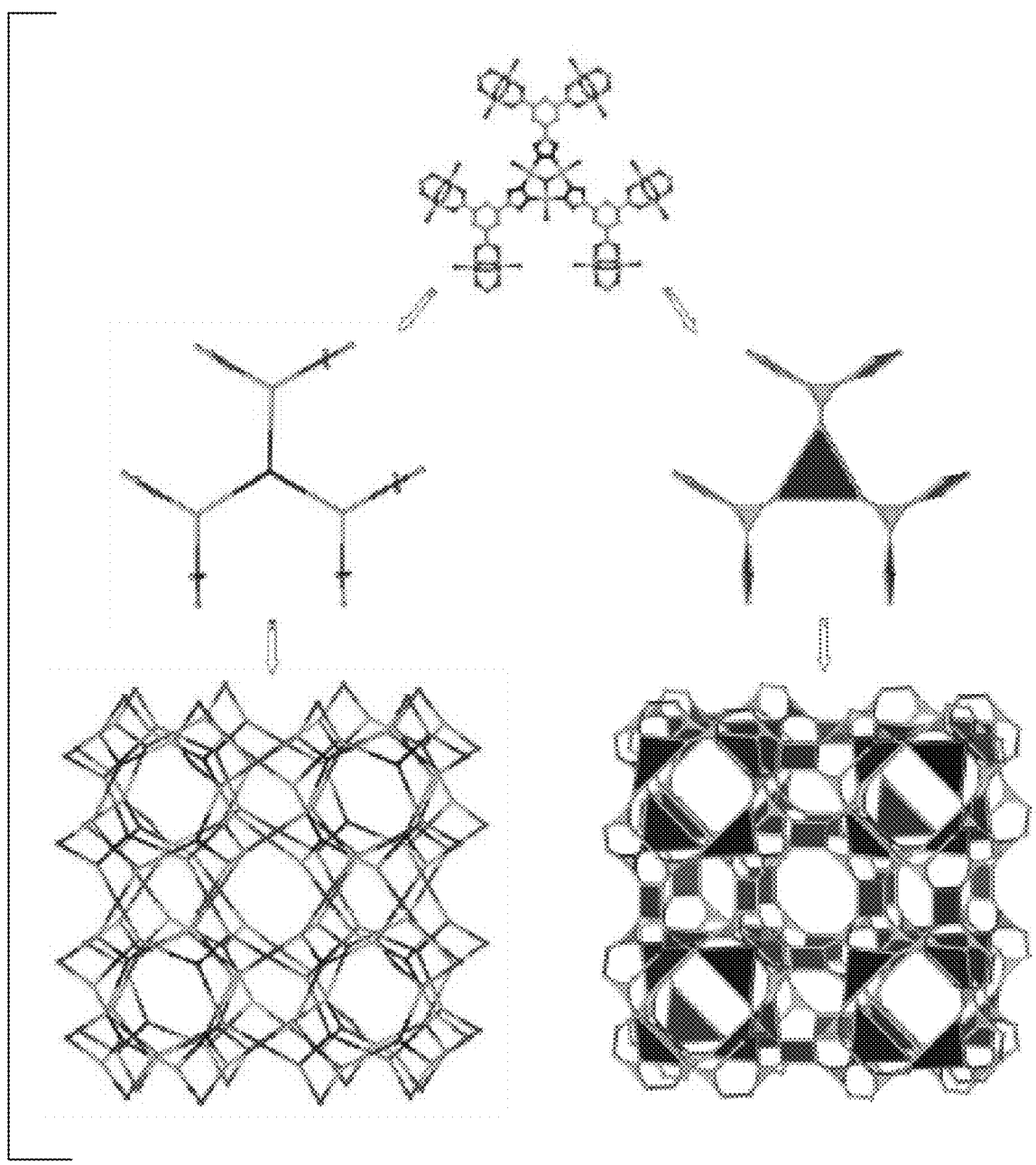
FIG. 7 illustrates the structure of [1] with its ternary topology. On the left is the ternary net, and on the right is the augmented ternary net. Topical terms for each node: (a) 6.6.8.8.8(2).8(2), Coordination Sequence: 4, 8, 18, 29, 52, 61, 106, 120, 170, 187 $TD_{10}$ 755(0.654); (b) 6.8 (2).8(3), Coordination Sequence: 3, 8, 15, 29, 40, 69, 81, 131, 146, 206 $TD_{10}$ 728(0.630); (c) 8(3).8(3).8(3), Coordination Sequence: 3, 6, 18, 24, 42, 63, 84, 93, 183, 175; $TD_{10}$ 691(0.598).
Figure 8:
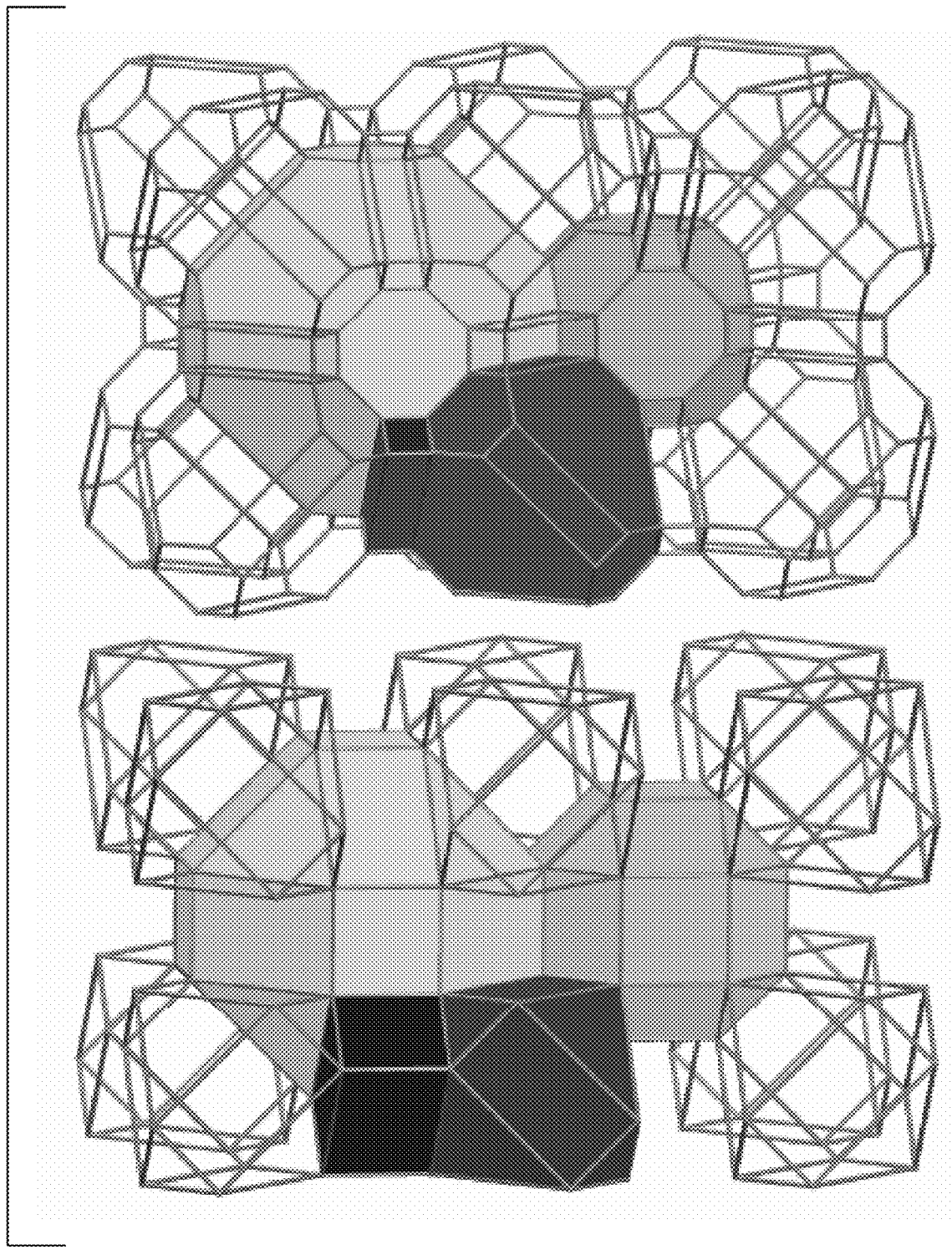
FIG. 8 illustrates that the structure of [1] with rht-like topology can be interpreted in several ways: Ita (α cage—yellow, green; β cage—red; and d4r—blue) and reo-e (rhombicuboctahedron—yellow, green; cuboctahedron—red; and d4r—blue). Here, the cage is formed by the 1,3-BDC linker is in green, and the yellow cage represents the largest cavity in [1].

It should be noted that the present framework can also be topologically interpreted as a novel 3D (3,3,4)-connected ternary net, (i.e., trinodal), based on the assembly of three different basic SBUs (FIG. 7) (O'Keeffe, M. Reticular Chemistry Structure Resource). The first MBB, copper paddlewheel $Cu_2(CO_2)_4$, augments the 4-connected vertex; the second is the trigonal $Cu_3O(N_4CR)_3$ trimer that augments the first 3-connected vertex; and the third is the tritopic ligand, which was designed to be bifunctional to accommodate two types of metal clusters at each of the two types of coordination functionalities (tetrazolate and carboxylate), augments the second 3-connected vertex. The SBB approach involving multifunctional ligands is a novel pathway to design and construct ternary nets in MOFs (Wang et al., *Angew. Chem. Int. Ed.* 2005, 44, 2877-2880). In fact, the trinodal topology of 1 has never been observed experimentally or theoretically. It is also to mention that the connectivity in 1 can be interpreted to be related to inorganic zeolite A with Ita topology (FIG. 8).

Figure 3:
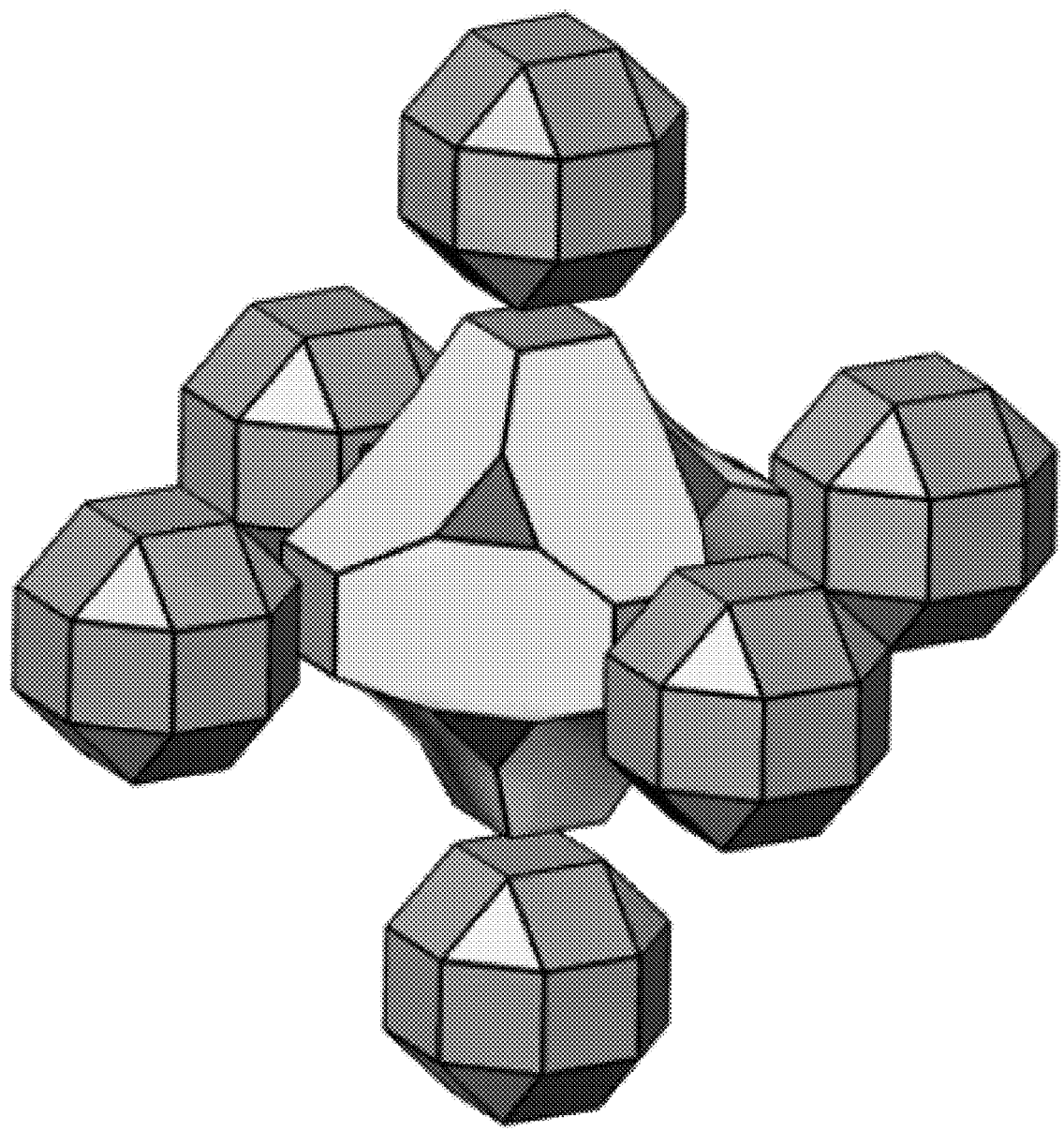
FIG. 3 is an illustration of the rht framework using tile presentation. The largest cage (yellow) is surrounded by six rhombicuboctahedral TBUs (green). The blue triangles delimiting the yellow cage represent trigonal $Cu_3O(N_4CR)_3$ trimers, and the green squares represent the quandrangular $Cu_2(O_2CR)_4$ paddlewheel MBBs.
Figure 9:
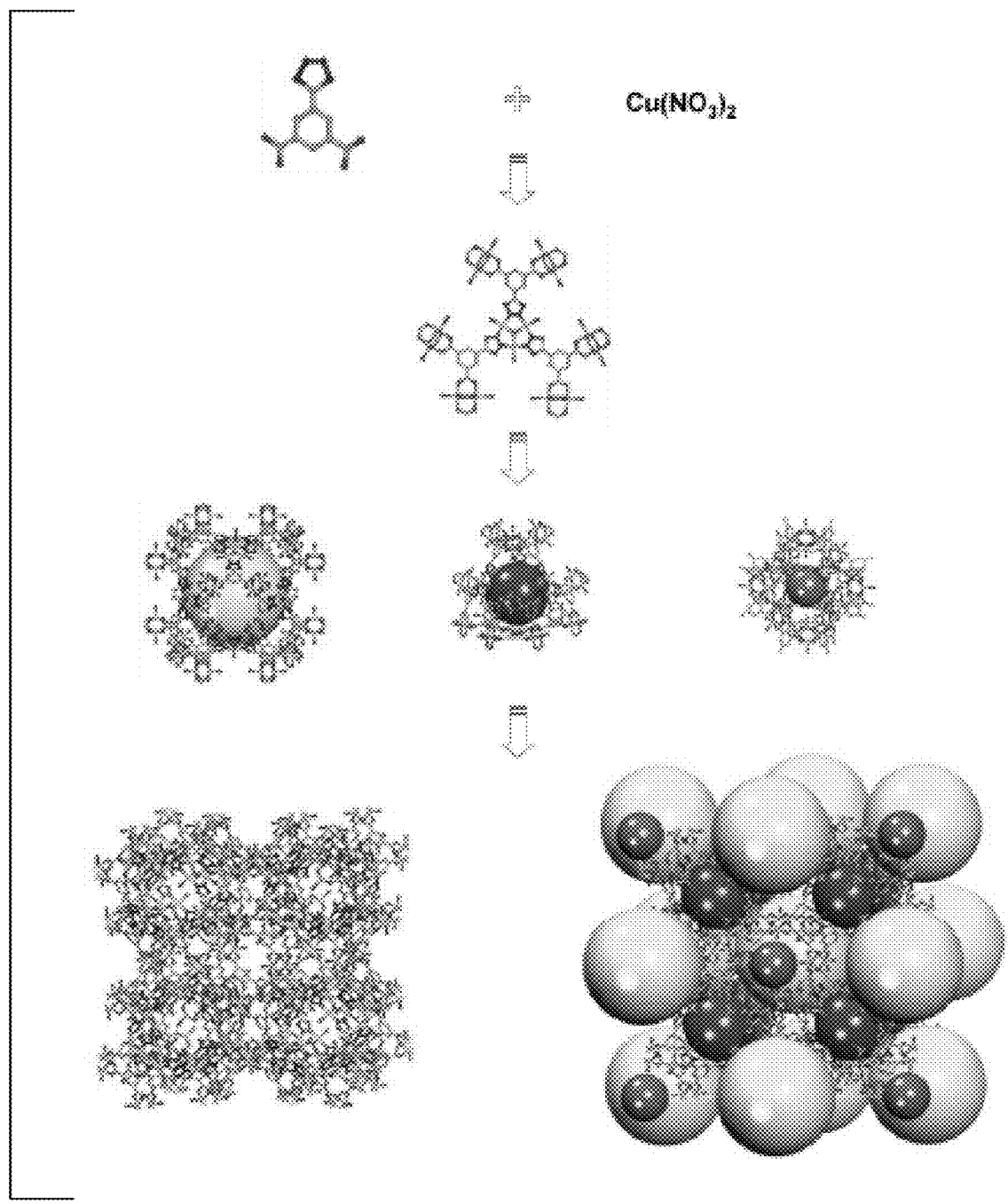
FIG. 9 illustrates the synthesis of [1] from TZI ligands and copper nitrate. These two components coordinate to give the assembly of the simple MBBs (shown centered around the oxo-trimer). In the crystal structure of [1] there are three different cages, which are represented with colored spheres (yellow for the first cage: 23.287 Å and 20.247 Å vdw sphere; fuchsia for the second cage (tetrahedron-like): 22.013 Å (height)×22.624 Å (edge) and 12.088 Å vdw sphere; turquoise for the third cage (truncated cuboctahedron): 15.877 Å and 13.077 Å vdw sphere (without terminal water).

The 5-position of the bridging ligand (isophthalate, 120° angle) lies exactly on the vertices of the rhombicuboctahedron. Delgado-Friedrichs, O. and O'Keeffe, supra. Thus, functionalization at this position with an organic moiety that permits the formation of a rigid triangular MBB will lead to the assembly of a MOF having the rht-like network topology, since this (3,24)-connected net is, to the best of our knowledge, the only edge transitive net known for the assembly of 24- and 3-connected vertices. (O'Keeffe, M. Reticular Chemistry Structure Resource) The overall cationic framework, where one $NO_3^-$ per three Cu cations balances the charge, consists of three different types of open cages (FIG. 9) with the largest having a 23.287 Å spherical diameter (20.247 Å including van der Waals (vdw) radii), delimited by 8 $Cu_3O(N_4CR)_3$ trimers and 24 $Cu_2(O_2CR)_4$ paddlewheel MBBs, and therefore surrounded by 6 truncated cuboctahedra (FIG. 3) and 8 tetrahedral-like cages. The tetrahedral-like cage, with a diameter of 22.013 Å (height)×22.624 Å (edge) (12.088 Å vdw sphere), is delimited by 4 $Cu_3O(N_4CR)_3$ trimers and 12 $Cu_2(O_2CR)_4$ paddlewheel MBBs, each is, as a result, surrounded by four truncated cuboctahedra and four of the largest cages; the truncated cuboctahedra with a diameter of 15.877 Å (13.077 Å vdw sphere) are delimited by 12 $Cu_2(O_2CR)_4$ paddlewheel MBBs, surrounded by 6 of the largest cages and 8 of the tetrahedral-like cages. The total solvent-accessible volume for 1 was estimated to be ~75% by summing voxels more than 1.2 Å away from the framework using PLATON software. Spek, A. L. *Acta Cryst.* 1990, A46, c34. Combined with a low calculated density (0.702 g/cm$^3$), the large windows, open cavities, and charged nature make this framework seemingly prospective for gas storage, specifically $H_2$.

Figure 2A:
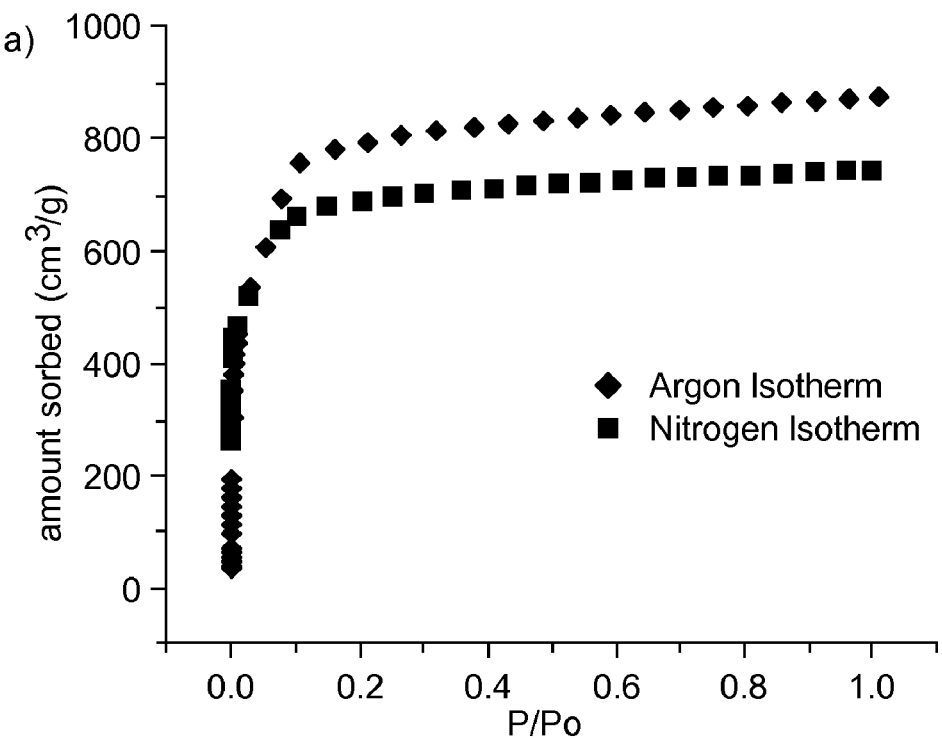
FIG. 2A is a graph depicting nitrogen and argon sorption isotherms at 78K and 87K, respectively.
Figure 10A:
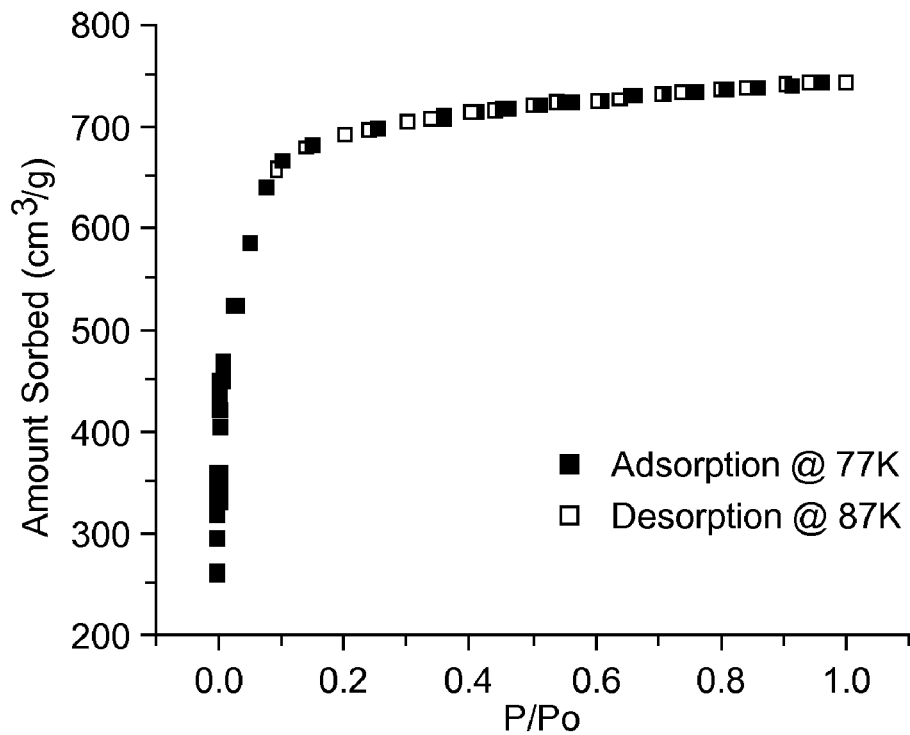
FIG. 10A is a graph depicting a nitrogen isotherm showing adsorption and desorption on [1].
Figure 10B:
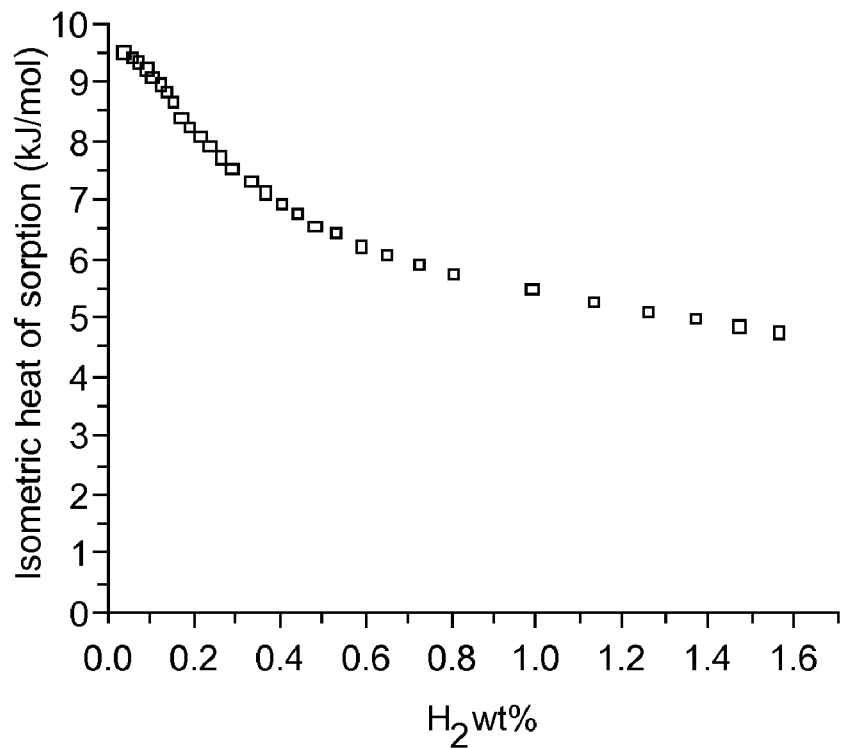
FIG. 10B is a graph depicting the isosteric heat of sorption for hydrogen on [1].
Figure 11:
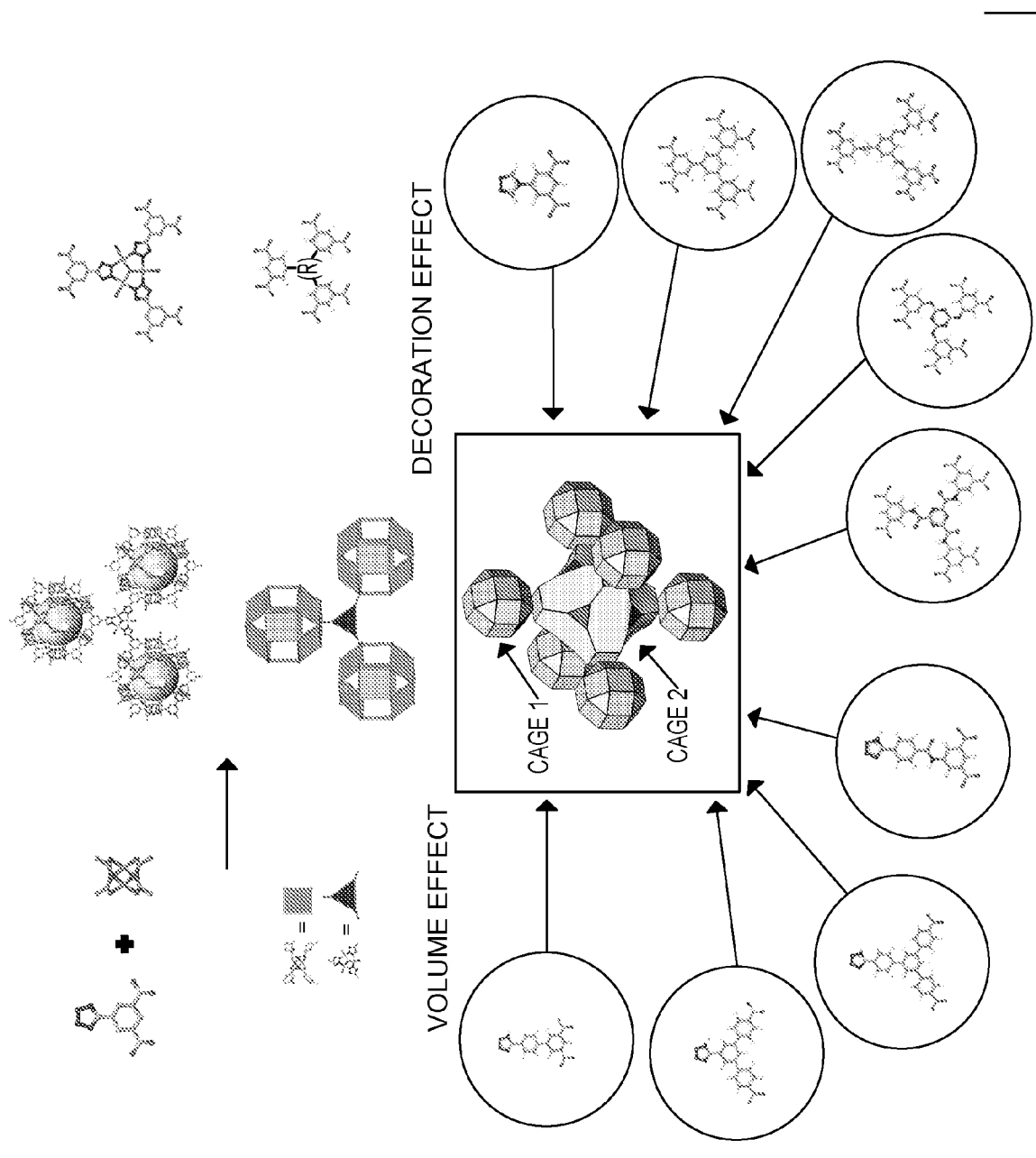
FIGS. 11 and 12 illustrate different ligand compounds, trimers, building units, and building blocks that can be used to form different (3,24)-connected rht nets.
Figure 12:
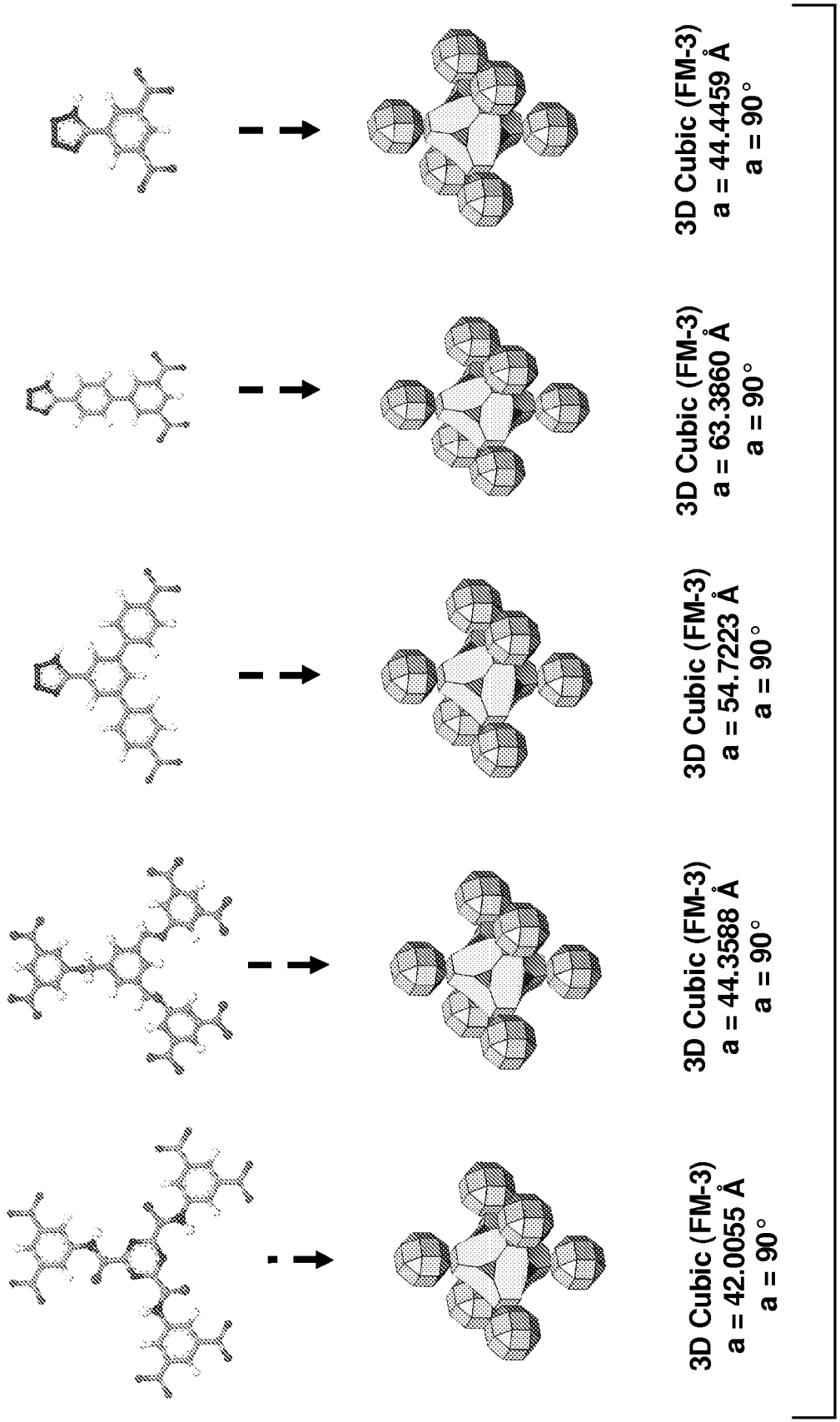
Figure 13:
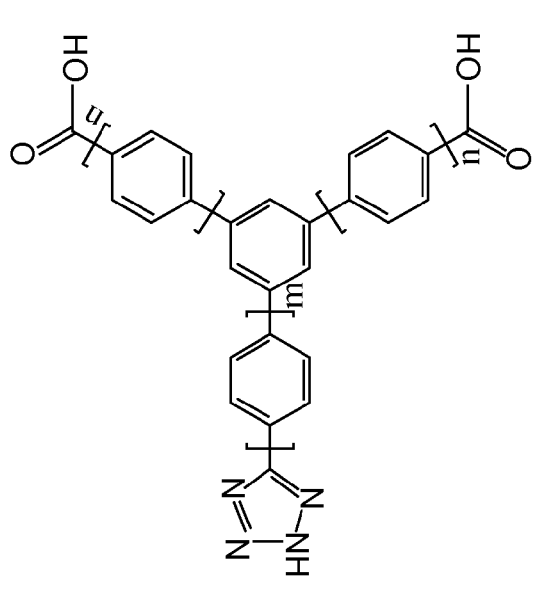
FIG. 13 illustrates different 5-tetraisophthalic acid derivatives.
Figure 13:
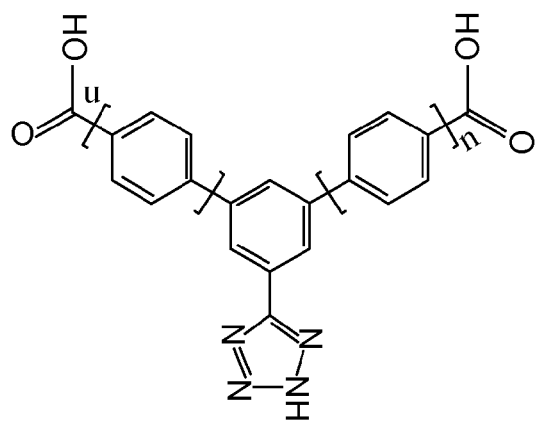
Figure 13:
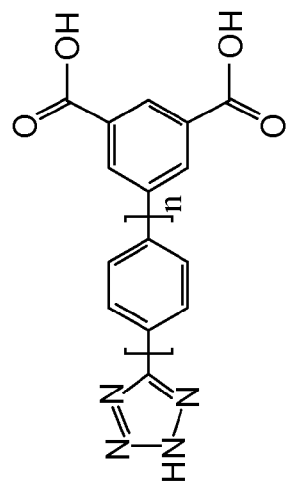
Figure 14:
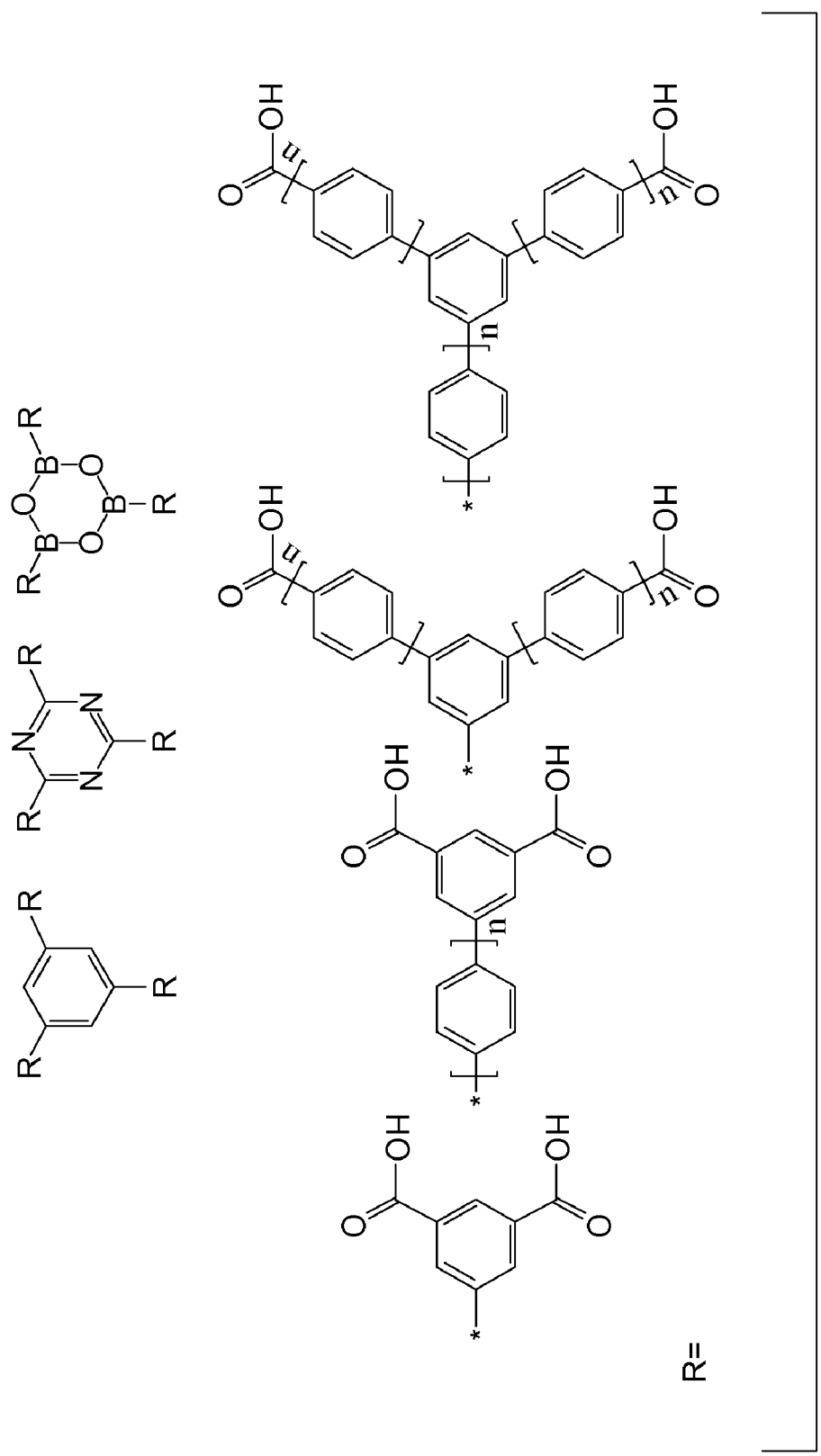
FIG. 14 illustrates different hexakis-isophthalic acid derivatives, where the organic core (e.g., benzene, triazine, or boroxine) mimics the metal tetrazolate trimer.
Figure 15:
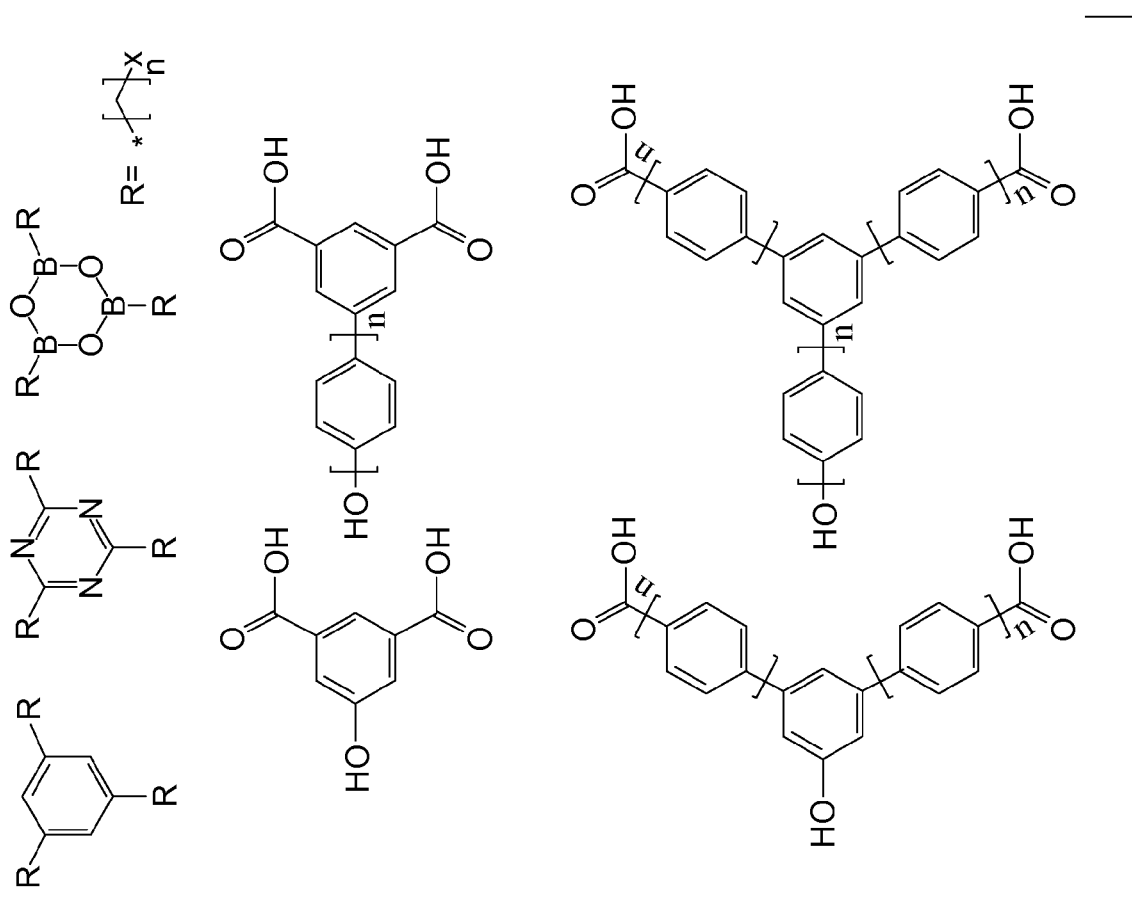
FIG. 15 illustrates different tris-halomethyl derivatives of the organic cores (e.g., benzene, triazine, or boroxine) that can be reacted with the 5-hydroxyisophthalic acid derivatives to give additional ligands.

In order to assess the sorption properties of 1, the guests were exchanged with ethanol. The crystalline material was allowed to air dry before being loaded into the sample cell, where it was outgassed first at room temperature and then 85° C. for 6 hours. Argon and nitrogen isotherms can be regarded as pseudo-type I isotherms (FIG. 2A) and the apparent surface area was estimated using Langmuir and BET methods ($N_2$: 3223 m$^2$/g and 2847 m$^2$/g, respectively); the total pore volume was found to be 1.01 cm$^3$/g ($N_2$). An interesting feature of the isotherms can be observed for pressures between 0.01 atm to 0.1 atm, where a second slope appears. This phenomenon is attributed to the three different cage diameters, where the largest cages approach mesoporous range; the smallest cages are the first to be covered and the largest are subsequently covered at higher pressure (FIGS. 10A and 10B).

Figure 2B:
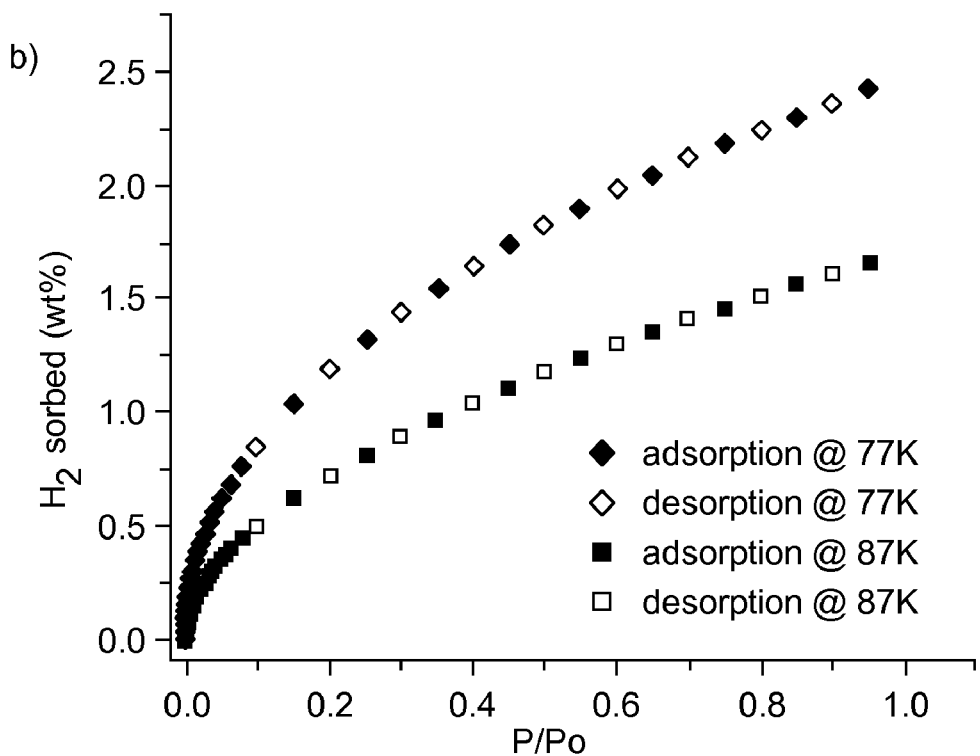
FIG. 2B is a graph depicting hydrogen sorption isotherms at 77K and 87K.

Hydrogen capacity was assessed for 1, measured at 77K and 87K at atmospheric pressures (FIG. 2B). The $H_2$ capacity is 2.4 wt % at 77K. The isosteric heat of sorption has an estimated value of 9.5 kJ/mol at the lowest coverage. This indicates the higher strength of $H_2$ interactions compared to previous MOFs. See, e.g., Rowsell et al., *J. Am. Chem. Soc.* 2006, 128, 1304-1315; Dinca et al., *Angew. Chem. Int. Ed.* 2007, 46, 1419-1422; Dinca et al., *J. Am. Chem. Soc.* 2007, 129, 11172-11176; Mulfort et al., *J. Am. Chem. Soc.* 2007, 129, 9604-9605; Liu et al., *Angew. Chem. Int. Ed.* 2007, 46, 3278-3283; Hayashi et al., *Nat. Mater.* 2007, 6, 501-506. Nevertheless, the isosteric heat falls to 4.7 kJ/mol at higher loadings, which is in accordance with the large size of the cavities filled at higher loading (FIGS. 10A and 10B). With a combined large surface area and accessible free volume, 1 offers great potential for higher $H_2$ uptake at 77K and higher pressures (estimated up to 6%).

The uniqueness of the rht net is beneficial to the practice of isoreticular chemistry, where higher surface areas and larger free pore volumes are easily achieved through expansion of the bifunctional organic linker or the use of hexakis-isophthalic acid derivatives synthesized to contain metal-tetrazolate trimer mimics (benzene, triazine, or boroxine). Other ligands based on the same strategy are the tris-halomethyl derivatives of the organic cores (i.e. benzene, triazine, or boroxine) that react with the 5-hydroxyisophthalic acid derivatives to give more potential ligands.

X-ray crystallography for [1]: The X-ray intensities were measured using Bruker-AXS SMART APEX/CCD diffractometer (MoKα, λ=0.71073 Å). Indexing was performed using SMART v5.625. Frames were integrated with SaintPlus 6.01 software package. Absorption correction was performed by multi-scan method implemented in SADABS. The structure was solved using SHELXS-97 and refined using SHELXL-97 contained in SHELXTL v6.10 and WinGX v1.70.01 programs packages. The non-hydrogen atoms of anions were refined anisotropically, hydrogen atoms were placed in geometrically calculated positions and included in the refinement process using riding model. Disordered solvent atoms were refined isotropically. Because of disorder, hydrogen atoms of solvent molecules were not localized. Large anisotropic displacement parameters (ADP's) for N(1), N(2), Cu(3) and O(13) atoms can be explained by vibration perpendicular to plane formed by these atoms. Because the geometry of this fragment is similar to the geometry of analogical fragments in the CSD database, a more complicated model of disorder was not used. Nitrogen and oxygen atoms of nitrate anions were found in the Fourier map and refined using constraints. Due to disorder, diffraction was visible up to 19.23°Θ. Crystal data and refinement conditions are shown in Table 1.

TABLE 1

Crystal data and structure refinement for compound 1.

| | |
|---|---|
| Empirical formula | $Cu(C_9H_3N_4O_4)_{0.5}(NO_3)_{0.167}(O^{2-})_{0.167}(H_2O)_{3.9}$ |
| Formula weight | 258.5 |
| Temperature | 100(2) K |
| Wavelength | 0.71073 A |
| Crystal system, space group | c. F m-3 m |
| Unit cell dimensions | a = b = c = 44.358(8) A |
| Volume | 87280(27) $A^3$ |
| Z, Calculated density | 192. 0.93 $Mg/m^3$ |
| Absorption coefficient | 1.207 $mm^{-1}$ |
| F(000) | 24046 |
| Crystal size | 0.20 × 0.20 × 0.20 mm |
| Theta range for data collection | 2.05 to 19.23 deg. |
| Limiting indices | $-5 <= h <= 41, -31 <= k <= 40, -38 <= l <= 37$ |
| Reflections collected/unique/observed | 9092/1702/1265 [R(int) = 0.1309] |
| Completeness to theta = 19.98 | 92.0% |
| Max. and min. transmission | 0.7942 and 0.7942 |
| Refinement method | Full-matrix least-squares on $F^2$ |
| Data/restraints/parameters | 1702/0/197 |
| Goodness-of-fit on $F^2$ | 1.084 |
| Final R indices [I > 2sigma(I)] | R1 = 0.0787, wR2 = 0.1781 |
| R indices (all data) | R1 = 0.1085, wR2 = 0.1933 |
| Largest diff. peak and hole | 0.754 and −0.552 $e.A^{-3}$ |

What is claimed is:

1. A supramolecular assembly comprising a 1:8 ratio of a supermolecular polyhedral building block and a triangular molecular building block, the supermolecular polyhedral building block having points of extension corresponding to the vertices of a rhombicuboctahedron for linking the supermolecular polyhedral building block to the triangular building blocks wherein an individual supramolecular polyhedral building block is linked to twenty-four different triangular building blocks and an individual triangular building block is linked to three different supermolecular polyhedral building blocks, the linkages comprising covalent bonds, coordinate covalent bonds, noncovalent bonds, or a combination thereof.

2. The supramolecular assembly of claim 1 wherein the supramolecular assembly is a metal-organic framework.

3. The supramolecular assembly of claim 2 wherein the metal-organic supermolecular polyhedral building block and the triangular molecular building block comprise copper.

4. The supramolecular assembly of claim 2 wherein the supramolecular building block and the triangular building block are derived from the assembly of a metal and a ligand corresponding to Formula (2):

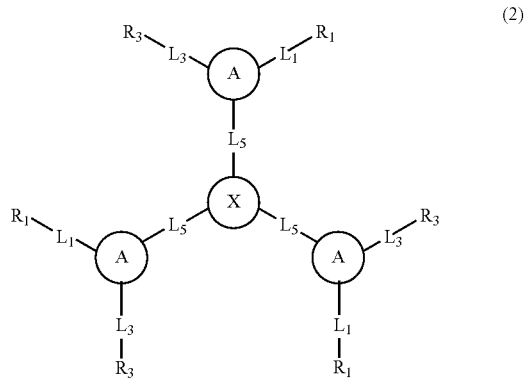

wherein
the X ring comprises a monocyclic ring or polycyclic fused ring system, or has the formula:

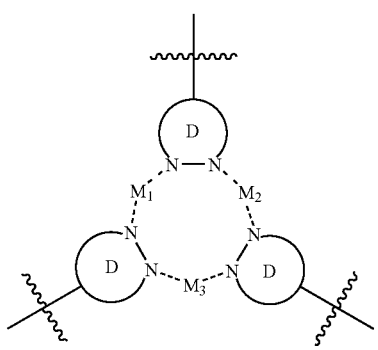

each A ring is a monocyclic ring or polycyclic fused ring system;

each $L_1$ and $L_3$ is a linker moiety;
each $L_5$ is a linker moiety;
each $R_1$ and $R_3$ is a functional group capable of coordinately bonding to at least one metal;
each D ring is a monocyclic ring or a polycyclic fused ring system;
$M_1$, $M_2$, and $M_3$ are independently metal ions; and
the dashed lines represent coordination between the nitrogen atom of a D ring and a metal.

5. The supramolecular assembly of claim 4 wherein the A rings are a benzene, boroxine, or triazine ring.

6. The supramolecular assembly of claim 4 wherein the X ring is a benzene ring.

7. The supramolecular assembly of claim 4 wherein $L_1$ is a bond or $-(L_{11})_m-$, wherein $L_{11}$ is hydrocarbylene or substituted hydrocarbylene and m is a positive integer, and $L_3$ is a bond or $-(L_{33})_m-$, wherein $L_{33}$ is hydrocarbylene or substituted hydrocarbylene and n is a positive integer, with $L_1$ and $L_3$ being the same.

8. The supramolecular assembly of claim 4 wherein the metal is a transition metal.

9. The supramolecular assembly of claim 4 wherein $L_1$ and $L_3$ is a bond.

10. The supramolecular assembly of claim 4 wherein the metal is $L_1$ and $L_3$ are the same and are substituted or unsubstituted phenylene.

11. The supramolecular assembly of claim 4 wherein $L_5$ is a bond or $-(L_{555})_m-$, wherein $L_{555}$ has the formula: —NH—, —C(=O)—NH—, —C(=O)—O—, —$R_y$—O—, —O—C(=O)—NH—, —SO$_2$—NH—, or —NH—C(=O)—NH—, wherein $R_y$ is alkylene, and m is a positive integer.

12. The supramolecular assembly of claim 4 wherein $R_1$ and $R_3$ are bidentate functional groups.

13. The supramolecular assembly of claim 4 wherein $R_1$ and $R_3$ are carboxylic acid (—CO$_2$H) groups.

14. The supramolecular assembly of claim 1 wherein the supramolecular building block and the triangular building block are derived from the assembly of a metal and a ligand having the formula:

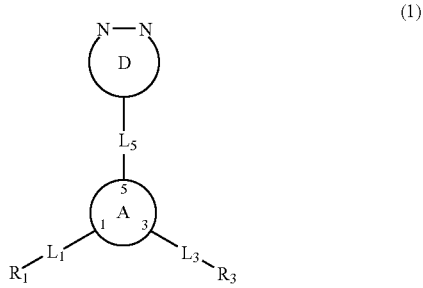

(1)

wherein
the A ring is a monocyclic ring or polycyclic fused ring system;
each $L_1$ and $L_3$ is a linker moiety;
$L_5$ is a linker moiety;
each $R_1$ and $R_3$ is a functional group capable of coordinately bonding to at least one metal;
the D ring is a monocyclic ring or a polycyclic fused ring system; and
the -$L_1$-$R_1$, -$L_3$-$R_3$, and -$L_5$-D ring moieties are positioned about 120° from each other.

15. The supramolecular assembly of claim 14 wherein the A ring is a benzene, boroxine, or triazine ring.

16. The supramolecular assembly of claim 14 wherein the A ring is a benzene ring.

17. The supramolecular assembly of claim 14 wherein the ligand has the formula:

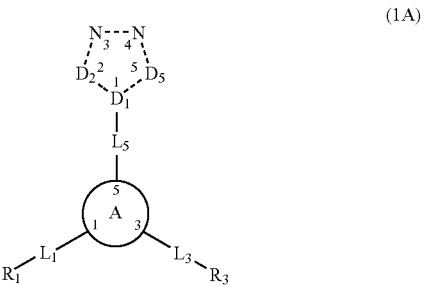

(1A)

wherein the D ring and the $D_1$, $D_2$, and $D_5$ ring atoms define a pyrazolyl, triazolyl, or tetrazolyl ring, provided that at least one of $D_1$, $D_2$, and $D_5$ is a carbon atom.

18. The supramolecular assembly of claim 14 wherein the ligand corresponds to Formula (1B):

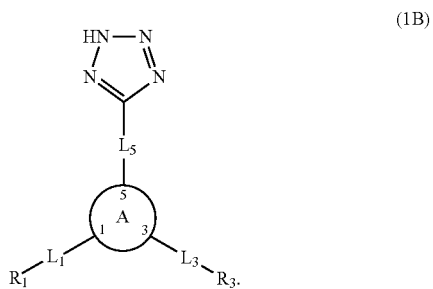

(1B)

19. The supramolecular assembly of claim 18 wherein $L_1$ is a bond or $-(L_{11})_m-$, wherein $L_{11}$ is hydrocarbylene or substituted hydrocarbylene and m is a positive integer, and $L_3$ is a bond or $-(L_{33})_m-$, wherein $L_{33}$ is hydrocarbylene or substituted hydrocarbylene and n is a positive integer, with $L_1$ and $L_3$ being the same.

20. The supramolecular assembly of claim 18 wherein $L_1$ and $L_3$ are each a bond or $-(L_{111})_m-$ and $-(L_{333})_m-$, respectively, wherein $L_{111}$ and $L_{333}$ have the formula: —NH—, —C(=O)—NH—, —C(=O)—O—, —$R_y$—O—, —O—C(=O)—NH—, —SO$_2$—NH—, or —NH—C(=O)—NH—, wherein $R_y$ is alkylene, and m is a positive integer.

21. The supramolecular assembly of claim 18 wherein $L_1$ and $L_3$ is a bond.

22. The supramolecular assembly of claim 18 wherein $L_1$ and $L_3$ are the same and are substituted or unsubstituted alkylene, or substituted or unsubstituted arylene.

23. The supramolecular assembly of claim 18 wherein $L_1$ and $L_3$ are the same and are substituted or unsubstituted phenylene.

24. The supramolecular assembly of claim 18 wherein $L_5$ is a bond or $-(L_{55})_m-$, wherein $L_{55}$ is hydrocarbylene or substituted hydrocarbylene and m is a positive integer.

25. The supramolecular assembly of claim 18 wherein $L_5$ is a bond or $-(L_{555})_m-$, wherein $L_{555}$ has the formula: —NH—, —C(=O)—NH—, —C(=O)—O—, —$R_y$—O—, —O—C(=O)—NH—, —SO$_2$—NH—, or —NH—C(=O)—NH—, wherein $R_y$ is alkylene, and m is a positive integer.

26. The supramolecular assembly of claim 18 wherein $L_5$ is a bond.

27. The supramolecular assembly of claim 18 wherein $L_5$ is substituted or unsubstituted phenylene.

28. The supramolecular assembly of claim 18 wherein $R_1$ and $R_3$ are bidentate functional groups.

29. The supramolecular assembly of claim 18 wherein $R_1$ and $R_3$ are carboxylic acid ($-CO_2H$) groups.

30. The supramolecular assembly of claim 18 wherein the metal is a transition metal.

31. A process for the preparation of a supramolecular assembly, the process comprising combining a metal source and a ligand to generate a composition comprising a 1:8 ratio of a supermolecular polyhedral building block and a triangular molecular building block, the supermolecular polyhedral building block having points of extension corresponding to the vertices of a rhombicuboctahedron for linking the supermolecular polyhedral building block to the triangular building blocks wherein an individual supermolecular polyhedral building block is linked to twenty-four different triangular building blocks and an individual triangular building block is linked to three different supermolecular polyhedral building blocks, the linkages comprising covalent bonds, coordinate covalent bonds, noncovalent bonds, or a combination thereof.

* * * * *